(12) United States Patent
Ito

(10) Patent No.: US 9,309,174 B2
(45) Date of Patent: *Apr. 12, 2016

(54) POLYCYCLIC RING ASSEMBLY COMPOUND AND ORGANIC ELECTROLUMINESCENT DEVICE EMPLOYING THE SAME

(75) Inventor: Mitsunori Ito, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 590 days.

This patent is subject to a terminal disclaimer.

(21) Appl. No.: 12/665,074

(22) PCT Filed: Jun. 16, 2008

(86) PCT No.: PCT/JP2008/060973
§ 371 (c)(1),
(2), (4) Date: Dec. 17, 2009

(87) PCT Pub. No.: WO2008/156052
PCT Pub. Date: Dec. 24, 2008

(65) Prior Publication Data
US 2010/0187512 A1  Jul. 29, 2010

(30) Foreign Application Priority Data

Jun. 20, 2007  (JP) .............................. 2007-162666

(51) Int. Cl.
| H01L 51/50 | (2006.01) |
|---|---|
| C07C 15/28 | (2006.01) |
| C07C 13/48 | (2006.01) |
| C07C 13/567 | (2006.01) |
| C07C 13/60 | (2006.01) |
| C07C 15/38 | (2006.01) |
| C07C 17/263 | (2006.01) |
| C07C 25/22 | (2006.01) |
| C07C 43/20 | (2006.01) |
| C07C 211/54 | (2006.01) |
| C07D 307/91 | (2006.01) |
| C07D 333/54 | (2006.01) |
| C07D 333/76 | (2006.01) |
| C07F 7/08 | (2006.01) |
| C09K 11/06 | (2006.01) |
| H05B 33/14 | (2006.01) |
| C09B 6/00 | (2006.01) |

(Continued)

(52) U.S. Cl.
CPC ............... *C07C 15/28* (2013.01); *C07C 13/48* (2013.01); *C07C 13/567* (2013.01); *C07C 13/60* (2013.01); *C07C 15/38* (2013.01); *C07C 17/263* (2013.01); *C07C 25/22* (2013.01); *C07C 43/202* (2013.01); *C07C 211/54* (2013.01); *C07D 307/91* (2013.01); *C07D 333/54* (2013.01); *C07D 333/76* (2013.01); *C07F 7/0809* (2013.01); *C09B 1/00* (2013.01); *C09B 6/00* (2013.01); *C09B 57/001* (2013.01); *C09K 11/06* (2013.01); *H01L 51/006* (2013.01); *H01L 51/0058* (2013.01); *H05B 33/14* (2013.01); *C07C 2101/08* (2013.01); *C07C 2101/14* (2013.01); *C07C 2102/08* (2013.01); *C07C 2102/10* (2013.01); *C07C 2103/18* (2013.01); *C07C 2103/24* (2013.01); *C07C 2103/26* (2013.01); *C07C 2103/50* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/007* (2013.01); *H01L 51/0054* (2013.01); *H01L 51/0059* (2013.01); *H01L 51/0081* (2013.01); *H01L 51/5012* (2013.01)

(58) Field of Classification Search
USPC .................. 428/690, 917; 313/504, 505, 506; 257/40, E51.05, E51.026, E51.032; 585/27
See application file for complete search history.

(56) References Cited

U.S. PATENT DOCUMENTS

2004/0209118 A1 * 10/2004 Seo et al. ...................... 428/690
2004/0253389 A1    12/2004 Suzuki et al.
(Continued)

FOREIGN PATENT DOCUMENTS

| JP | 3 200889 | 9/1991 |
|---|---|---|
| JP | 7 138561 | 5/1995 |
| JP | 8 239655 | 9/1996 |
| JP | 2004 43349 | 2/2004 |

(Continued)

OTHER PUBLICATIONS

Baldo M.A. et al., "Highly efficient phosphorescent emission from organic electroluminescent devices", Letters to Nature, vol. 395, pp. 151-155, Sep. 10, 1998.

(Continued)

*Primary Examiner* — Gregory Clark
(74) *Attorney, Agent, or Firm* — Oblon, McClelland, Maier & Neustadt, L.L.P

(57) ABSTRACT

Polycyclic ring assembly compound which has a specific flexible partial structure, i.e., a structure containing an aromatic ring in which adjacent carbon atoms have, bonded thereto, an aromatic ring group of another kind and an aliphatic group or aromatic ring group. Also provided are: a polymer constituted of repeating units at least part of which are structures derived from the polycyclic ring assembly compound; a solution of an organic EL material containing the polycyclic ring assembly compound or the polymer; and an organic electroluminescence device. The organic electroluminescence device has excellent heat resistance, high color purity, and a long lifetime and can emit a blue light or green light at a high luminescent efficiency. The polycyclic ring assembly compound realizes the device.

17 Claims, No Drawings

(51) Int. Cl.
*C09B 57/00* (2006.01)
*C09B 1/00* (2006.01)
*H01L 51/00* (2006.01)

(56) References Cited

U.S. PATENT DOCUMENTS

| | | |
|---|---|---|
| 2005/0089715 A1 | 4/2005 | Cosimbescu et al. |
| 2005/0123787 A1* | 6/2005 | Robello et al. ............... 428/690 |
| 2006/0043858 A1* | 3/2006 | Ikeda et al. .................. 313/250 |

FOREIGN PATENT DOCUMENTS

| | | | | |
|---|---|---|---|---|
| JP | 2004-043349 | * | 2/2004 | ............ C07C 13/547 |
| JP | 2004 83481 | | 3/2004 | |
| JP | 2007-084485 | * | 4/2007 | ............. C07C 15/24 |
| WO | 2007 105884 | | 9/2007 | |
| WO | 2007 108666 | | 9/2007 | |

OTHER PUBLICATIONS

Burroughes J.H. et al., "Light-emitting diodes based on conjugated polymers", Letters to Nature, vol. 347, pp. 539-541, Oct. 11, 1990.

* cited by examiner

POLYCYCLIC RING ASSEMBLY COMPOUND AND ORGANIC ELECTROLUMINESCENT DEVICE EMPLOYING THE SAME

TECHNICAL FIELD

The present invention relates to a polycyclic ring assembly compound; a polymer constituted of repeating units at least part of which are structures derived from the polycyclic ring assembly compound; a solution containing an organic electroluminescent material containing the polycyclic ring assembly compound; and an organic electroluminescence (hereinafter, which may sometimes be abbreviated as EL) device. Especially, the present invention relates to the organic EL device having excellent heat resistance, a high color purity, and a long lifetime and can emit a blue light or green light at a high luminescent efficiency, and to the polycyclic ring assembly compound realizing the device.

BACKGROUND ART

An organic electroluminescence device is a spontaneous light emitting device which utilizes the phenomenon that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Page 913, 1987), many studies have been conducted on organic EL devices using organic materials as the constituting materials. Tang et al. used tris(8-quinolinolato) aluminum for the light emitting layer and a triphenyldiamine derivative for the hole transporting layer. Advantages of the laminate structure are that the efficiency of hole injection into the light emitting layer can be increased, that the efficiency of forming excitons which are formed by blocking and recombining electrons injected from the cathode can be increased, and that the excitons formed in the light emitting layer can be confined. As described above, for the structure of the organic EL device, a two-layered structure having a hole transporting (injecting) layer and an electron-transporting light emitting layer and a three-layered structure having a hole transporting (injecting) layer, a light emitting layer, and an electron-transporting (injecting) layer are well known. In order to increase the efficiency of recombination of injected holes and electrons in the devices of the laminate type, the structure of the device and the process for forming the device have been studied.

As the light emitting material, chelate complexes such as tris(8-quinolinolato)aluminum, coumarin derivatives, tetraphenylbutadiene derivatives, bis-styrylarylene derivatives and oxadiazole derivatives are known. It is reported that light in the visible region ranging from blue light to red light can be obtained by using these light emitting materials, and development of a device exhibiting color images is expected (For example, Patent Documents 1 to 3).

In recent years, a large number of investigations have been conducted on the use of a phosphorescent compound as a light emitting material and the use of energy in a triplet state in EL light emission. A group of Princeton University has reported that an organic light emitting device using an iridium complex as a light emitting material shows high luminous efficiency (Non-patent Document 1). In addition to the organic electroluminescence device using a low molecular weight material as described above, an organic electroluminescence device using a conjugated polymer has been reported by a group of Cambridge University (Non-patent Document 2). In this report, light emission has been confirmed from a monolayer of polyphenylene vinylene (PPV) formed in a coating system.

Recent advances in organic electroluminescence device are remarkable, and characteristics of the organic electroluminescence device allow formation of a thin and lightweight light-emitting device with high luminance under application of a low voltage, wide range of emission wavelengths, and high-speed response, thereby suggesting the possibility of extensive uses.

In association with the significant progress of an organic light emitting device, performance requested of a light emitting material has been growing, and Patent Documents 4 and 5 each disclose a compound with a specific structure as a material achieving high luminous emission under application of a low voltage and being excellent in durability.

Further, Patent Document 6 discloses a material to which a specific flexible partial structure such as an ortho bond is introduced and organic EL device with the use of it. However, regarding with a device performance, despite the improvement of the color purity, the lifetime is too short to achieve the practical use.

In the present state of affairs, however, an optical output of further high luminance or high conversion efficiency is necessary. Moreover, there are many problems of durability such as change with the passage of time due to a long time usage and degradation or so caused by an atmospheric gas including oxygen or a moisture. Furthermore, although light emission of blue, green and red with excellent color purity becomes necessary considering about application to full color display, countermeasures about these problems are not sufficient yet.

Patent Document 1: JP 08-239655A
Patent Document 2: JP 07-183561A
Patent Document 3: JP 3-200889A
Patent Document 4: JP 2004-83481
Patent Document 5: JP 2004-43349
Patent Document 6: US 2005/0089715 A1
Non-patent Document 1: Nature, 395,151 (1998)
Non-patent Document 2: Nature, 347,539 (1990)

DISCLOSURE OF THE INVENTION

Problems to be Solved by the Invention

The present invention has been made to overcome the above problems and has an object of providing a polycyclic ring assembly compound employable for the light emitting material for an organic EL device with capability of improving both color purity and lifetime, a polymer constituted of repeating units at least part of which are structures derived from the polycyclic ring assembly compound, and a solution containing an organic EL material containing the polycyclic ring assembly compound. Further, the present invention has an object of providing an organic EL device, using the polycyclic ring assembly compound or the polymer compound, being excellent in heat resistance, with a high color purity, and with a long lifetime and being capable of emitting blue light or green light at a high luminescent efficiency. Still further, the present invention also has an object of enabling to produce the organic EL device easily and with relatively reasonable expense.

Means for Solving the Problem

As a result of intensive researches and studies to achieve the above object by the present inventors, it was found that an employment of a polycyclic ring assembly compound represented by the following general formula (1) or a polymer constituted of repeating units at least part of which are structures derived from the polycyclic ring assembly compound as a material for the organic EL device achieves enabling to produce the organic EL device with high color purity and long lifetime, resultantly completing the present invention.

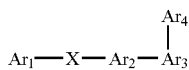
(1)

where: $A_1$ represents a hydrogen atom, a substituted or unsubstituted aromatic ring group having 6 to 50 ring carbon atoms, or a substituted or unsubstituted aromatic heterocyclic ring group having 5 to 50 ring atoms;
X represents a substituted or unsubstituted divalent aromatic fused ring group having 10 to 50 ring carbon atoms;
$Ar_2$ represents a single bond, a substituted or unsubstituted divalent aromatic ring group having 6 to 50 ring carbon atoms, or a substituted or unsubstituted divalent heterocyclic ring group having 5 to 50 ring atoms;
$Ar_3$ represents a substituted or unsubstituted divalent aromatic fused ring group having 10 to 50 ring carbon atoms, or a substituted or unsubstituted divalent heterocyclic ring group having 5 to 50 ring atoms
$Ar_4$ represents a substituted or unsubstituted aromatic ring group having 6 to 50 ring carbon atoms, a substituted or unsubstituted heterocyclic ring group having 5 to 50 ring atoms, a substituted or unsubstituted alkyl group having 1 to 50 carbon atoms, a substituted or unsubstituted cycloalkyl group having 3 to 20 carbon atoms, or a substituted or unsubstituted alkoxy group having 1 to 50 carbon atoms;
with the proviso that $Ar_2$ and $Ar_4$ bond with an adjacent carbon atom to $Ar_3$.

Further, the present invention provides an organic EL device being composed of one or more organic thin film layers including at least one light emitting layer interposed between a cathode and an anode, wherein at least one of the organic thin film layers contains the polycyclic ring assembly compound represented by the general formula (1) or the polymer compound constituted of repeating units at least part of which are structures derived from the polycyclic ring assembly compound as the light emitting layer. Furthermore, the present invention provides a solution of an organic EL material containing the polycyclic ring assembly compound or the polymer compound.

Effect of the Invention

An employment of a light emitting material containing the polycyclic ring assembly compound represented by the general formula (1) or the polymer compound constituted of repeating units at least part of which are structures derived from the polycyclic ring assembly compound enabled an improvement of color purity and longer lifetimes to be compatible altogether.

PREFERRED EMBODIMENT TO CARRY OUT THE INVENTION

A light emitting material for organic EL device of the present invention contains the polycyclic ring assembly compound represented by the general formula (1):

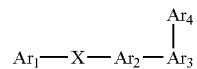
(2)

where: $Ar_1$ represents a hydrogen atom, a substituted or unsubstituted aromatic ring group having 6 to 50 ring carbon atoms, or a substituted or unsubstituted aromatic heterocyclic ring group having 5 to 50 ring atoms; X represents a substituted or unsubstituted divalent aromatic fused ring group having 10 to 50 ring carbon atoms; $Ar_2$ represents a single bond, a substituted or unsubstituted divalent aromatic fused ring group having 6 to 50 ring carbon atoms, or a substituted or unsubstituted divalent heterocyclic ring group having 5 to 50 ring atoms; $Ar_3$ represents a substituted or unsubstituted divalent aromatic fused ring group having 10 to 50 ring carbon atoms, or a substituted or unsubstituted divalent heterocyclic ring group having 5 to 50 ring atoms; $Ar_4$ represents a substituted or unsubstituted aromatic ring group having 6 to 50 ring carbon atoms, a substituted or unsubstituted heterocyclic ring group having 5 to 50 ring atoms, a substituted or unsubstituted alkyl group having 1 to 50 carbon atoms, a substituted or unsubstituted cycloalkyl group having 3 to 20 carbon atoms, or a substituted or unsubstituted alkoxy group having 1 to 50 carbon atoms; with the proviso that $Ar_2$ and $Ar_4$ bond with an adjacent carbon atom to $Ar_3$.

The polycyclic ring assembly compound of the present invention has preferably a partial structure represented by the following general formula (2) or (3):

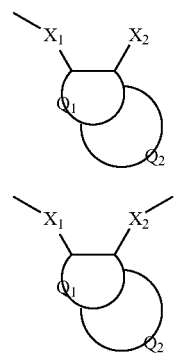

(2)

(3)

where: $X_1$ and $X_2$ each independently represents a substituted or unsubstituted aromatic hydrocarbon group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 5 to 50 ring atoms, a substituted or unsubstituted arylthio group having 5 to 50 ring atoms, or a substituted or unsubstituted alkoxycarbonyl group having 1 to 50 carbon atoms; or a divalent group derived from those; $Q_1$ and $Q_2$ each independently represents a group forming a ring structure; and the ring formed by $Q_1$ or $Q_2$ is a cycloalkane residue which may be substituted and having 3 to 20 ring carbon atoms whose carbon atoms may be substituted with a nitrogen atom, an aromatic hydrocarbon group having 6 to 50 carbon atoms which may be substituted or a heterocyclic group having 3 to 20 ring carbon atoms which may be substituted.

In the polycyclic ring assembly compound of the present invention, X in the general formula (1) is preferably a substituted or unsubstituted anthracene or a substituted or unsubstituted divalent aromatic fused ring group derived from pyrene.

In the polycyclic ring assembly compound of the present invention, a partial structure: —Ar$_2$—Ar$_3$—Ar$_4$ in the general formula (1) is preferably represented by the following general formulae (4) to (13):

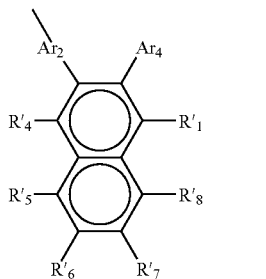

(4)

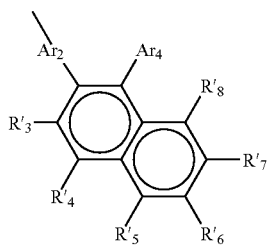

(5)

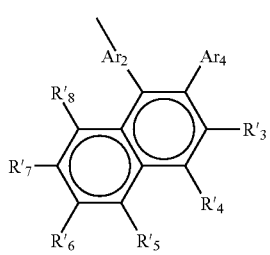

(6)

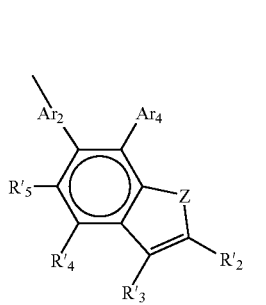

(7)

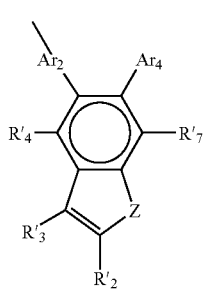

(8)

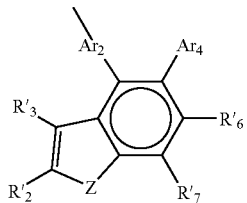

(9)

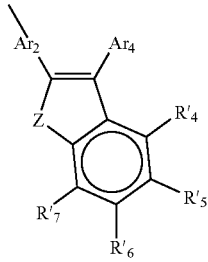

(10)

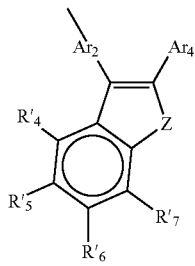

(11)

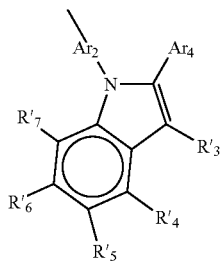

(12)

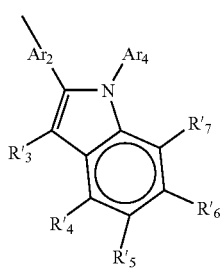

(13)

where: Ar$_2$ and Ar$_4$ represent the same as those in the general formula (1); Z in the general formulae (7) to (11) represents a sulfur atom or a nitrogen atom which may be substituted (>N—R'$_9$; R'$_9$ is a hydrogen atom, an alkyl group or an aromatic ring group). R'$_1$ to R'$_8$ each independently represents a hydrogen atom or a substituent; and neighboring couples of R'$_1$ to R'$_8$ may be bonded with each other to form a ring structure of an aliphatic group or an aromatic group.

The polycyclic ring assembly compound of the present invention is preferably represented by the following general formula (14) or (15):

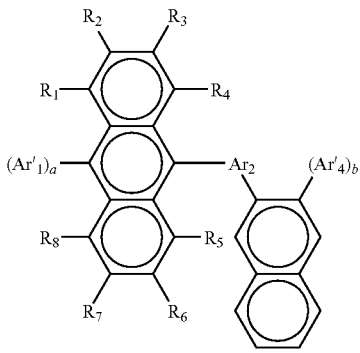

(14)

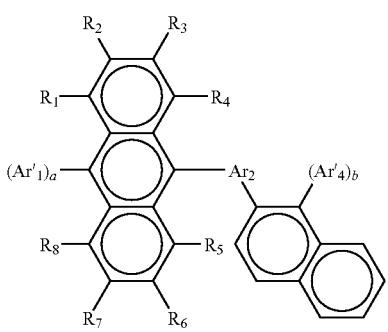

(15)

where: $(Ar'_1)_a$ entirely corresponds to $Ar_1$ in the general formula (1), and means that it consists of one monovalent aromatic ring group $Ar'_1$ and (a-1) pieces of a divalent aromatic ring group $Ar'_1$; $(Ar'_4)_b$ also has the same meaning, entirely corresponds to $Ar_4$ in the general formula (1), and means that it consists of one monovalent aromatic ring group $Ar'_4$ and (b-1) pieces of a divalent aromatic ring group $Ar'_4$; $Ar_2$ represents the same as $Ar_2$ in the general formula (1); a and b each independently represents an integer of 1 to 3, and when a is 2 or more, plurality of $Ar'_1$s may be identical to or different from each other; and when b is 2 or more, plurality of $Ar'_4$s may be identical to or different from each other; and $R_1$ to $R_8$ each independently represents a hydrogen atom or a substituent.

The polycyclic ring assembly compound of the present invention is preferably represented by the following general formula (16) or (17):

(16)

(17)

where: Py represents a substituted or unsubstituted monovalent group derived from pyrene, and plurality of Pys may be identical to or different from each other; Ar represents a constitutional unit of $Ar_2$ or $Ar_4$ in the general formula (1), being a divalent aromatic ring group or a divalent heterocyclic group: c, d, and e in the general formula (16) each independently represents an integer of 0 to 3; f and g each independently represents 0 or 1, and f+g=1; when f is 0 or when g is 0, a hydrogen atom or a substituent exists at these position; h, i, and j in the general formula (17) each independently represents an integer of 0 to 3, and plurality of Ar's may be identical to or different from each other; k and m each independently represents an integer of 0 or 1, and k+m=1.

In the polycyclic ring assembly compound of the present invention, Ar in the general formula (16) or (17) is preferably a substituted or unsubstituted naphthyl group or a substituted or unsubstituted phenyl group.

The polycyclic ring assembly compound of the present invention is preferably represented by the following general formula (18):

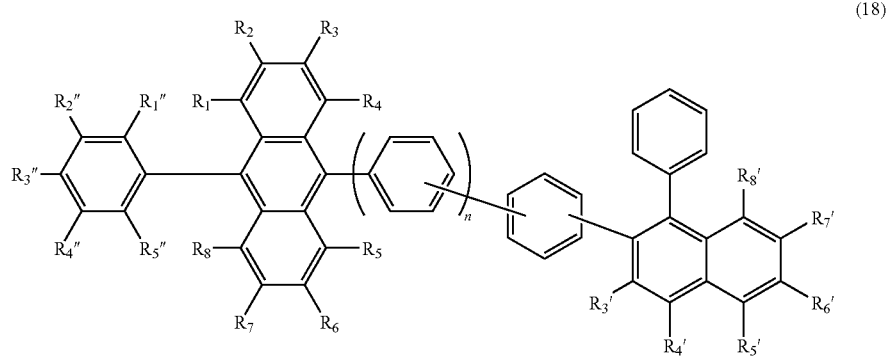

(18)

where: $R_1$ to $R_8$, $R_3'$ to $R_8'$ and $R_1''$ to $R_5''$ each independently represents a hydrogen atom or a substituent which may be identical to or different from each other; neighboring couples of $R_1$ to $R_8$, $R_3'$ to $R_8'$ and $R_1''$ to $R_5''$ may be bonded with each other to form a cyclic structure of an aliphatic group or an aromatic group; and n represents 0 or 1.

The polycyclic ring assembly compound of the present invention is preferably represented by the following general formula (19):

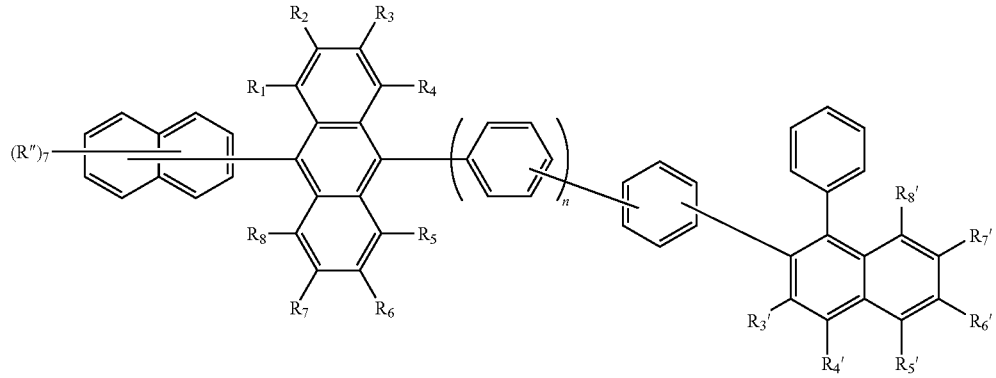

(19)

where: $R_1$ to $R_8$, and $R_3'$ to $R_8'$ each independently represents a hydrogen atom or a substituent which may be identical to or different from each other; seven R''s each independently represents a hydrogen atom or a substituent which may be identical to or different from each other; neighboring couples of $R_1$ to $R_8$, $R_3'$ to $R_8'$ and R''s may be bonded with each other to form a cyclic structure of an aliphatic group or an aromatic group; and n represents 0 or 1.

The polycyclic ring assembly compound of the present invention is preferably represented by the following general formula (20):

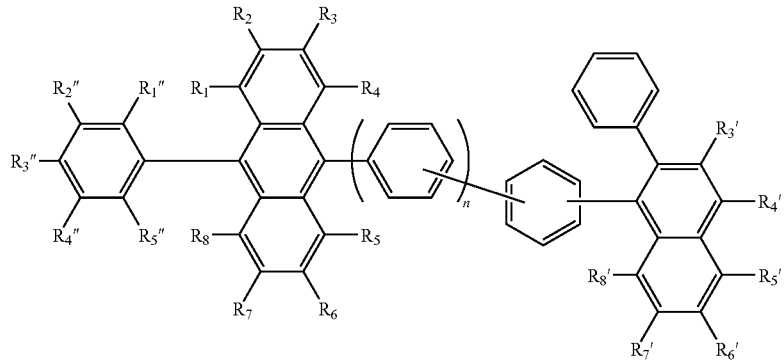

(20)

where: $R_1$ to $R_8$, $R_3'$ to $R_8'$ and $R_1''$ to $R_5''$ each independently represents a hydrogen atom or a substituent which may be identical to or different from each other; neighboring couples of $R_1$ to $R_8$, $R_3'$ to $R_8'$ and $R_1''$ to $R_5''$ may be bonded with each other to form a cyclic structure of an aliphatic group or an aromatic group; and n represents 0 or 1.

The polycyclic ring assembly compound of the present invention is preferably represented by the following general formula (21):

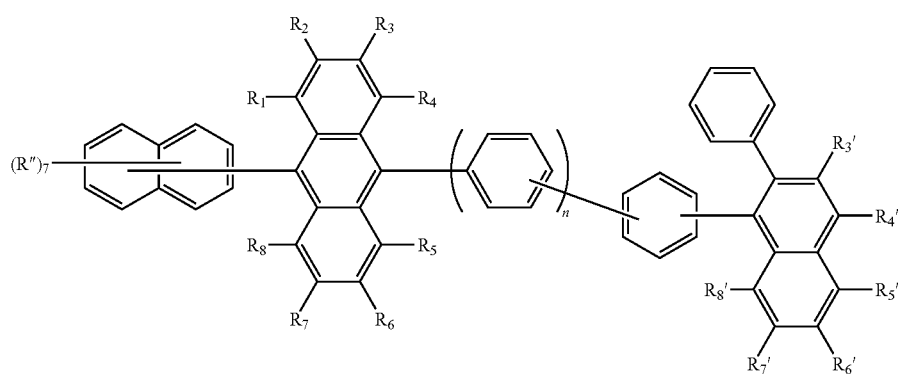

(21)

where: $R_1$ to $R_8$, and $R_3'$ to $R_8'$ each independently represents a hydrogen atom or a substituent which may be identical to or different from each other; seven R"s each independently represents a hydrogen atom or a substituent which may be identical to or different from each other; neighboring couples of $R_1$ to $R_8$, $R_3'$ to $R_8'$ and R"s may be bonded with each other to form a cyclic structure of an aliphatic group or an aromatic group; and n represents 0 or 1.

The polycyclic ring assembly compound of the present invention is preferably represented by the following general formula (22):

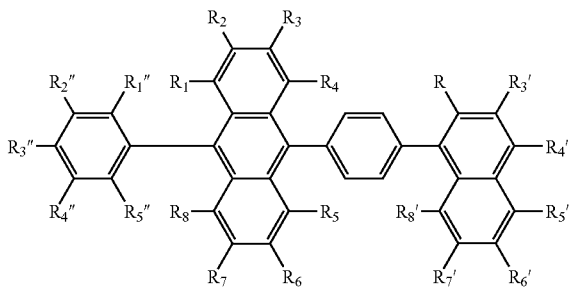

(22)

where: R represents a straight chain or branched alkyl group having 1 to 30 carbon atoms or a cycloalkyl group having 3 to 10 carbon atoms; $R_1$ to $R_8$, $R_3'$ to $R_8'$ and $R_1''$ to $R_5''$ each independently represents a hydrogen atom or a substituent which may be identical to or different from each other; neighboring couples of $R_1$ to $R_8$, $R_3'$ to $R_8'$ and $R_1''$ to $R_5''$ may be bonded with each other to form a cyclic structure of an aliphatic group or an aromatic group.

The polycyclic ring assembly compound of the present invention is preferably represented by the following general formula (23):

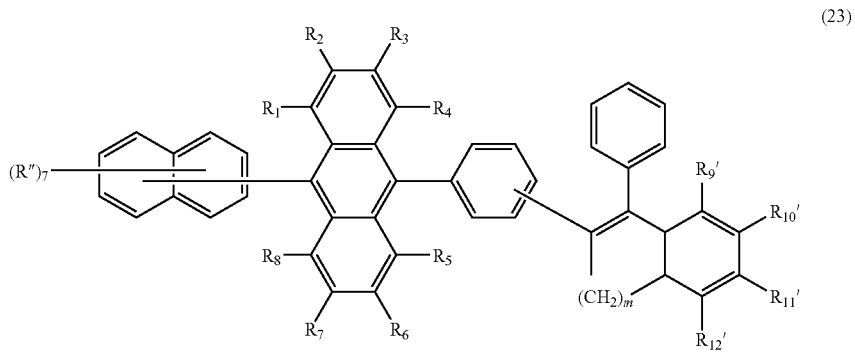

(23)

where: $R_1$ to $R_8$, and $R_9'$ to $R_{12}'$ each independently represents a hydrogen atom or a substituent which may be identical to or different from each other; seven R"s each independently represents a hydrogen atom or a substituent which may be identical to or different from each other; neighboring couples of $R_1$ to $R_8$, $R_9'$ to $R_{12}'$ and R"s may be bonded with each other to form a cyclic structure of an aliphatic group or an aromatic group; and m represents an integer of 1 to 3.

Examples of the aromatic ring group having 6 to 50 ring carbon atoms include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenyl-yl group, 4''-t-butyl-p-terphenyl-4-yl group, etc., and divalent groups of these.

Examples of the aromatic heterocyclic ring group having 5 to 50 ring atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1 isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1 isoquinolyl group, 3-isoquinolyl group, 4-isoquinolyl group, 5-isoquinolyl group, 6-isoquinolyl group, 7-isoquinolyl group, 8 isoquinolyl group, 2-quinoxalinyl group, 5-quinoxalinyl group, 6-quinoxalinyl group, 1-carbazoryl group, 2-carbazoryl group, 3-carbazoryl group, 4-carbazoryl group, 9-carbazoryl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl 1-indolyl group, 4-t-butyl 1-indolyl group, 2-t-butyl 3-indolyl group, 4-t-butyl 3-indolyl group, etc., and divalent groups of these.

Examples of a divalent aromatic fused ring group having 10 to 50 ring carbon atoms include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group, 4-methyl-1-naphthyl group, and a divalent group obtained by further removing a hydrogen atom from 4-methyl-1-anthryl group.

Preferable divalent aromatic fused ring group having 10 to 50 ring carbon atoms is a divalent group derived from anthracene or pyrene.

Examples of alkyl group having 1 to 50 carbon atoms include a methyl group, an ethyl group, a propyl group, an isopyl group, n-butyl group, s-butyl group, an isobutyl group, a dimethylmethyl group, n-pentyl group, n-hexyl group, n-heptyl group, n-octyl group, a chloromethyl group, 1-chloroethyl group, 2-chloroethyl group, 2-chloroisobutyl group, 1,2-dichloroethyl group, 1,3-dichloro isopropyl group, 1,2,3-trichloro propyl group, a bromomethyl group, 1-bromoethyl group, 2-bromoethyl group, 2-bromoisobutyl group, 1,2-dibromo ethyl group, 1,3-dibromo isopropyl group, 1,2,3-tribromo propyl group, iodomethyl group, 1-iodo ethyl group, 2-iodo ethyl group, 2-iodo isobutyl group, 1,2-diiodo ethyl group, 1,3-diiodo isopropyl group, 1,2,3-triiodo propyl group, etc. Further, examples of alkylene group include divalent groups of those.

Examples of cycloalkyl group having 3 to 50 carbon atoms include a cyclopropyl group, a cyclobutyl group, a cyclopentyl group, a cyclohexyl group, 4-methylcyclohexyl group, an adamantane-1,1-diyl group, an adamantane-1,3-diyl group, etc.

The alkoxy group having 1 to 50 carbon atoms is a group expressed by $-OY_1$, and examples of $Y_1$ are the same as those explained about the above alkyl group.

Examples of substituents include, an alkyl group (alkyl group preferably having 1 to 20 carbon atoms, more preferably having 1 to 12 carbon atoms and particularly preferably having 1 to 8 carbon atoms; examples include methyl, ethyl, iso-propyl, tert-butyl, n-octyl, n-decyl, n-hexadecyl, cyclopropyl, cyclopentyl, cyclohexyl, etc.); an alkenyl group (alkenyl group preferably having 2 to 20 carbon atoms, more preferably having 2 to 12 carbon atoms and particularly preferably having 2 to 8 carbon atoms; examples include vinyl, allyl, 2-butenyl, 3-pentenyl, etc.); an alkynyl group (alkynyl group preferably having 2 to 20 carbon atoms, more preferably having 2 to 12 carbon atoms and particularly preferably having 2 to 8 carbon atoms; examples include propargyl, 3-pentynyl, etc.); an amino group (amino group preferably having 0 to 20 carbon atoms, more preferably having 0 to 12 carbon atoms and particularly preferably having 0 to 6 carbon atoms; examples include amino, methylamino, dimethylamino, diethylamino, diphenylamino, dibenzylamino, etc.); an alkoxy group (alkoxy group preferably having 1 to 20 carbon atoms, more preferably having 1 to 12 carbon atoms and particularly preferably having 1 to 8 carbon atoms; examples include methoxy, ethoxy, butoxy, etc.); an aryloxy group (aryloxy group preferably having 6 to 20 carbon atoms, more preferably having 6 to 16 carbon atoms and particularly preferably having 6 to 12 carbon atoms; examples include phenyloxy, 2-naphthyloxy, etc.); an acyl group (acyl group preferably having 1 to 20 carbon atoms, more preferably having 1 to 16 carbon atoms and particularly preferably having 1 to 12 carbon atoms; examples include acetyl, benzoyl, formyl, pivaloyl, etc.); an alkoxycarbonyl group (alkoxycarbonyl group preferably having 2 to 20 carbon atoms, more preferably having 2 to 16 carbon atoms and particularly preferably having 2 to 12 carbon atoms; examples include methoxycarbonyl, ethoxycarbonyl, etc.); an aryloxycarbonyl group (aryloxycarbonyl group preferably having 7 to 20 carbon atoms, more preferably having 7 to 16 carbon atoms and particularly preferably having 7 to 10 carbon atoms; examples include phenyloxycarbonyl, etc.); an acyloxy group (acyloxy group preferably having 2 to 20 carbon atoms, more preferably having 2 to 16 carbon atoms and particularly preferably having 2 to 10 carbon atoms; examples include acetoxy, benzoyloxy, etc.); an acylamino group (acylamino group preferably having 2 to 20 carbon atoms, more preferably having 2 to 16 carbon atoms and particularly preferably having 2 to 10 carbon atoms; examples include acetylamino, benzoylamino, etc.); an alkoxycarbonylamino group (alkoxycarbonylamino group preferably having 2 to 20 carbon atoms, more preferably having 2 to 16 carbon atoms and particularly preferably having 2 to 12 carbon atoms; examples include methoxycarbonylamino, etc.); an aryloxycarbonylamino group (aryloxycarbonylamino group preferably having 7 to 20 carbon atoms, more preferably having 7 to 16 carbon atoms and particularly preferably having 7 to 12 carbon atoms; examples include phenyloxycarbonylamino, etc.); a sulfonylamino group (sulfonylamino group preferably having 1 to 20 carbon atoms, more preferably having 1 to 16 carbon atoms and particularly preferably having 1 to 12 carbon atoms; examples include methanesulfonylamino, benzenesulfonylamino, etc.); a sulfamoyl group (sulfamoyl group preferably having 0 to 20 carbon atoms, more preferably having 0 to 16 carbon atoms and particularly preferably having 0 to 12 carbon atoms; examples include sulfamoyl, methylsulfamoyl, dimethylsulfamoyl, phenylsulfamoyl, etc.); a carbamoyl group (carbamoyl group preferably having 1 to 20 carbon atoms, more preferably having 1 to 16 carbon atoms and particularly preferably having 1 to 12 carbon atoms; examples include carbamoyl, methylcarbamoyl, diethylcarbamoyl, phenylcarbamoyl, etc.); an alkylthio group (alkylthio group preferably having 1 to 20 carbon atoms, more preferably having 1 to 16 carbon atoms and particularly preferably having 1 to 12 carbon atoms; examples include methylthio, ethylthio, etc.); an arylthio group (arylthio group preferably having 6 to 20 carbon atoms, more preferably having 6 to 16 carbon atoms and particularly preferably having 6 to 12 carbon atoms; examples include phenylthio, etc.); a sulfonyl group (sulfonyl group preferably having 1 to 20 carbon atoms, more preferably having 1 to 16 carbon atoms and particularly preferably having 1 to 12 carbon atoms; examples include mesyl, tosyl, etc.); a sulfinyl group (sulfinyl group preferably having 1 to 20 carbon atoms, more preferably having 1 to 16 carbon atoms and particularly preferably having 1 to 12 carbon atoms; examples include methanesulfinyl, benzenesulfinyl, etc.); an ureide group (ureide group preferably having 1 to 20 carbon atoms, more preferably having 1 to 16 carbon atoms and particularly preferably having 1 to 12 carbon atoms; examples include ureide, methylureide, phenylureide, etc.); a phosphoricamide group (phosphoricamide group preferably having 1 to 20 carbon atoms, more preferably having 1 to 16 carbon atoms and particularly preferably having 1 to 12 carbon atoms; examples include diethylphosphoricamide, phenylphosphateamide, etc.); a hydroxy group; a mercapto group; a halogen atom (for example, fluorine atom, chlorine atom, bromine atom and iodine atom); a cyano group; a sulfo group; a carboxyl group; a nitro group; a hydroxamic acid group; a sulfino group; a hydrazino group; an imino group; a heterocyclic group (heterocyclic group preferably having 1 to 30 carbon atoms, more preferably having 1 to 12 carbon atoms; examples of the hetero atom include nitrogen atom, oxygen atom, sulfur atom; specific examples of the heterocyclic group include imidazolyl, pyridyl, quinolyl, furyl, thienyl, piperidyl, morpholino, benzoxazolyl, benzimidazolyl, benzothiazolyl, carbazolyl, etc.); a silyl group (silyl group preferably having 3 to 40 carbon atoms, more preferably having 3 to 30 carbon atoms and particularly preferably having 3 to 24 carbon atoms; examples include trimethylsilyl, triphenylsilyl, etc.); etc. Those substituents may be further substituted. Furthermore, when there are two or more substituents, the substituents may be identical to or different from each other. Also, in a case where it is possible, they may be bonded with each other to form a ring.

Moreover, examples of the substituent in "substituted or unsubstituted" among each of the above general formulae include the same substituents as those above description.

Typical examples of the polycyclic ring assembly compound represented by the general formula (1) of the present invention are shown below, though not particularly limited thereto.

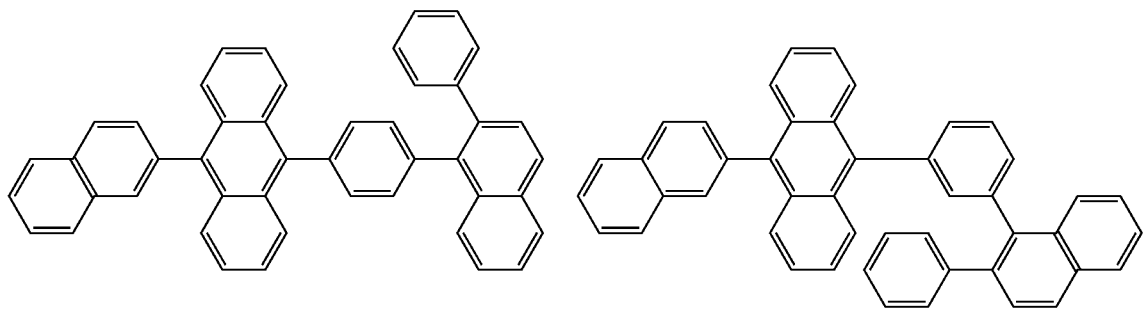

-continued
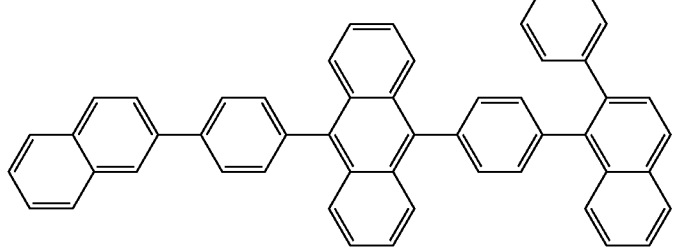
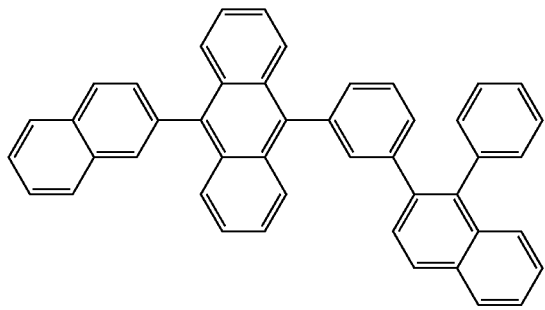
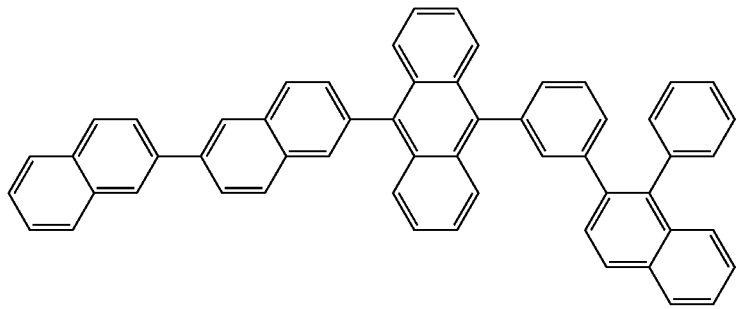
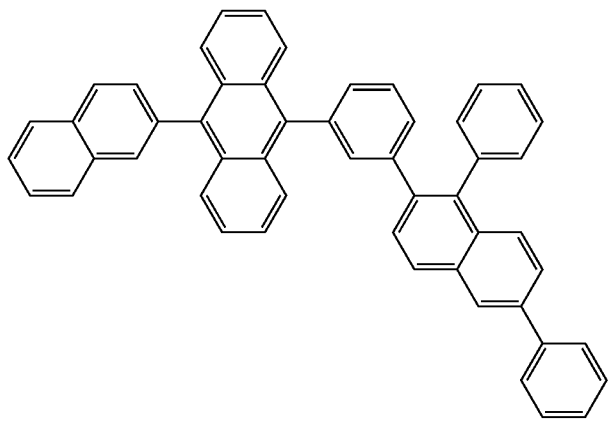
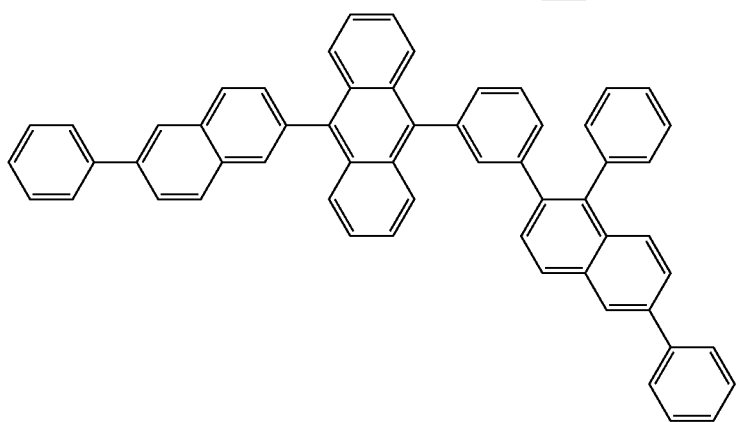

-continued
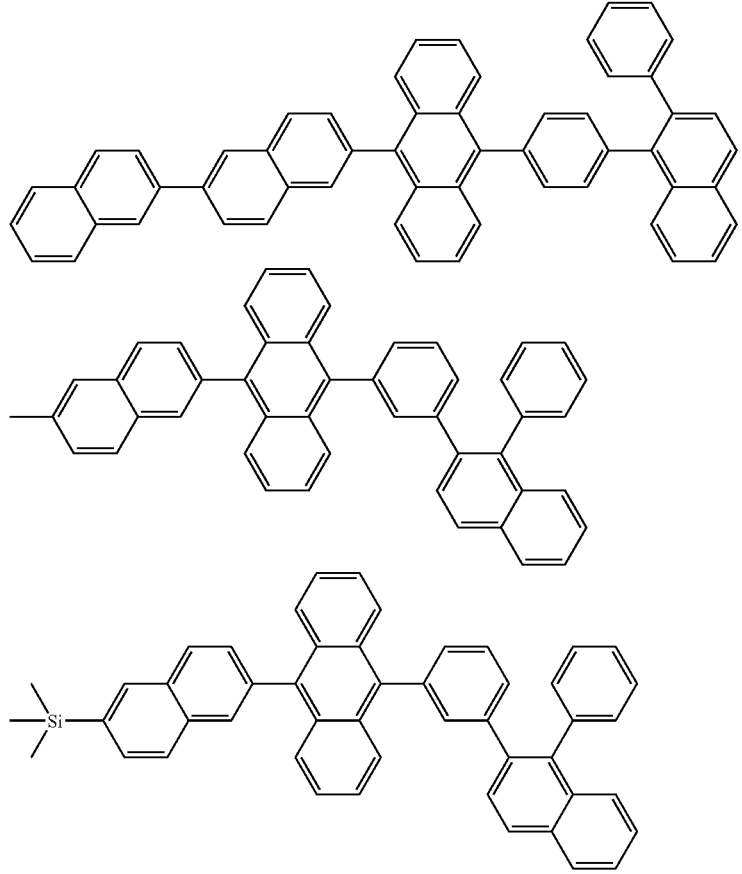
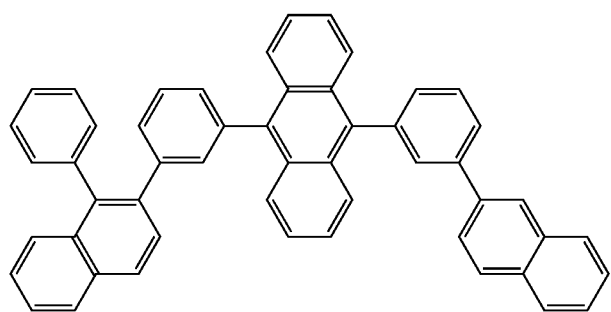
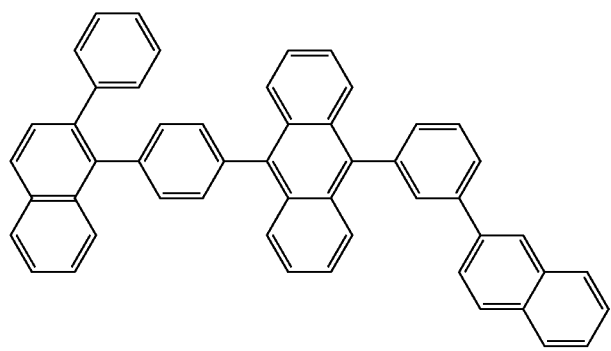

-continued
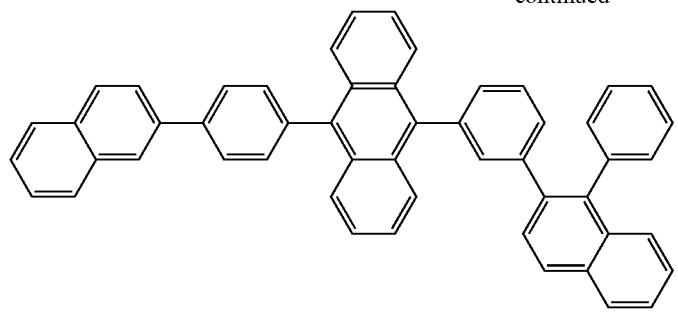
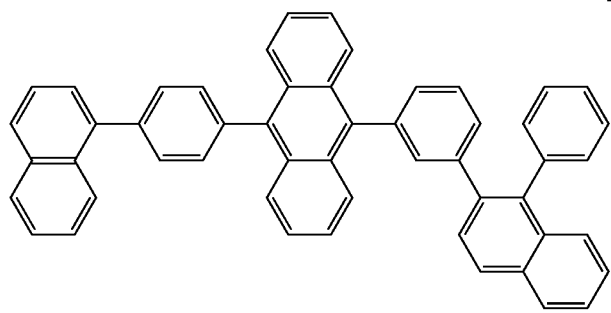
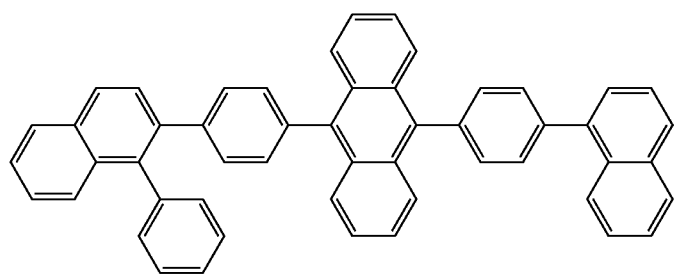
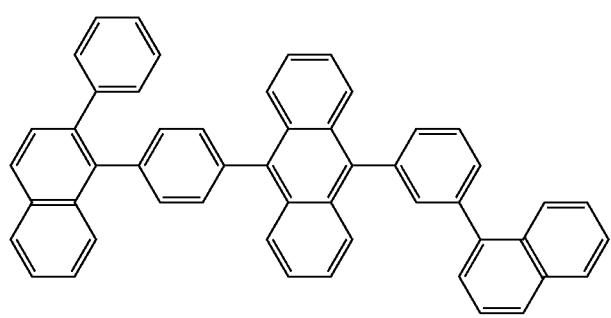
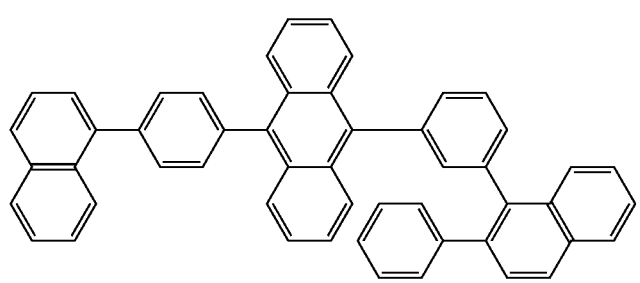

-continued
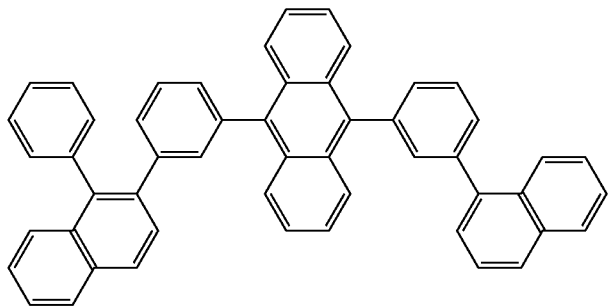
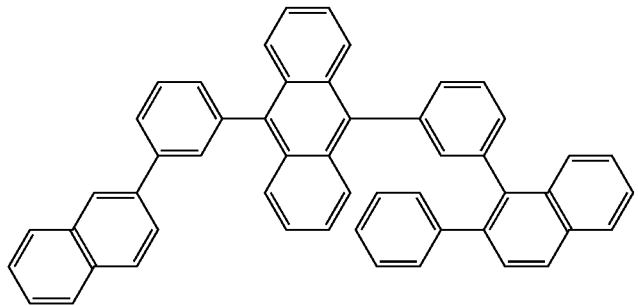
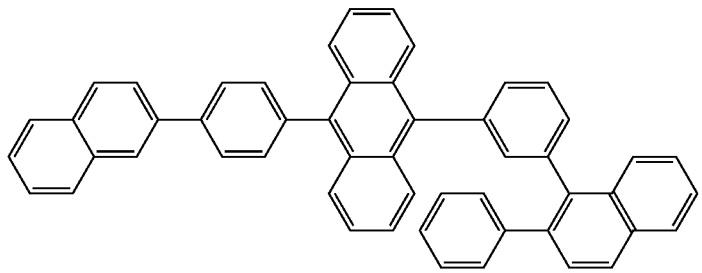
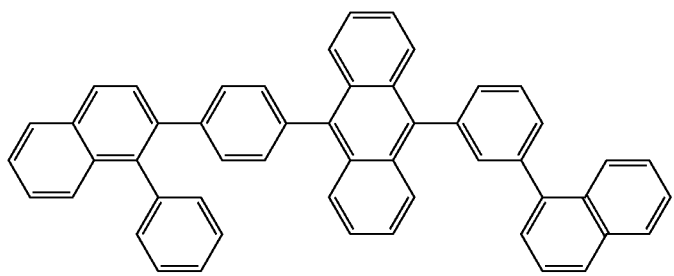
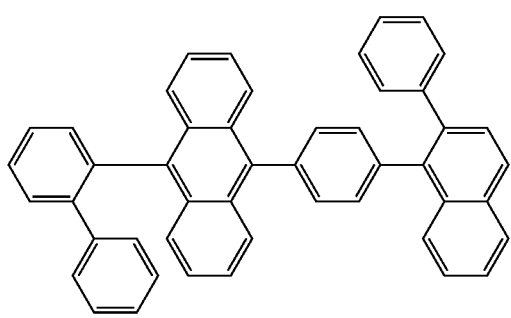

-continued
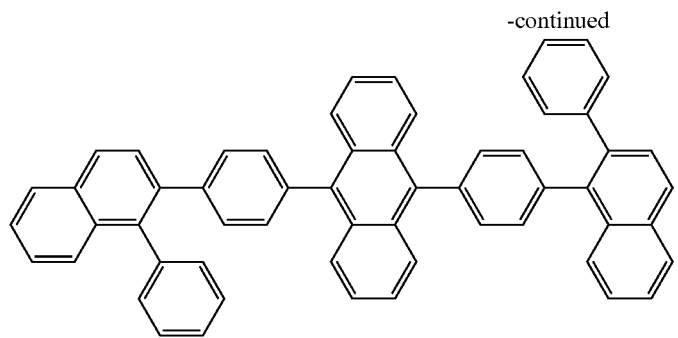
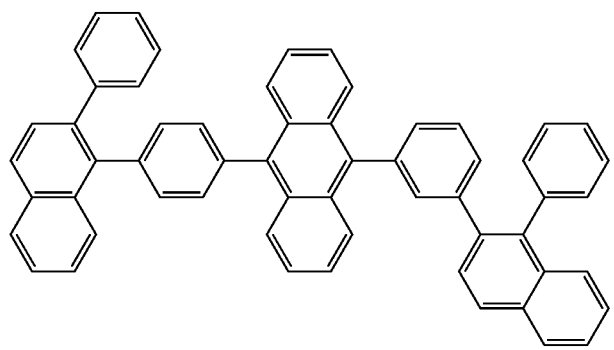
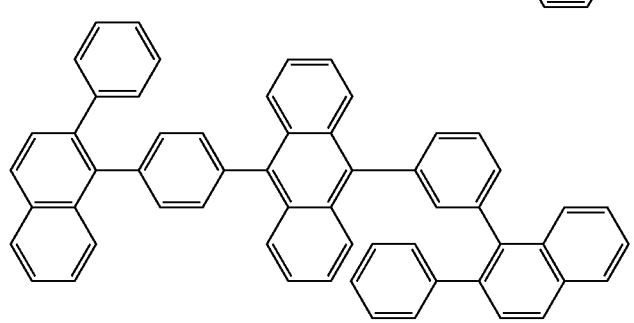
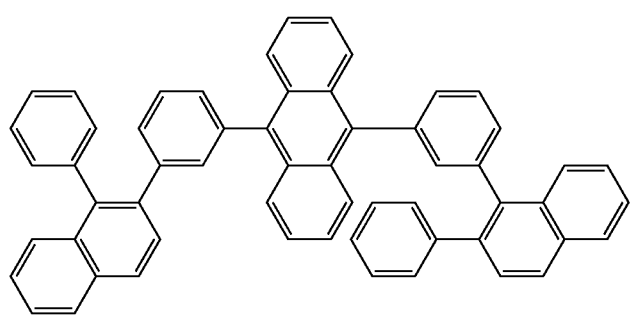
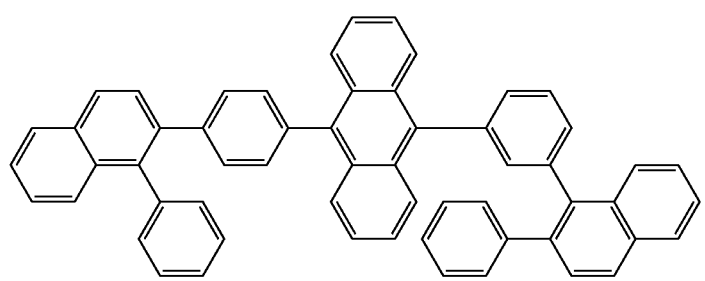

-continued
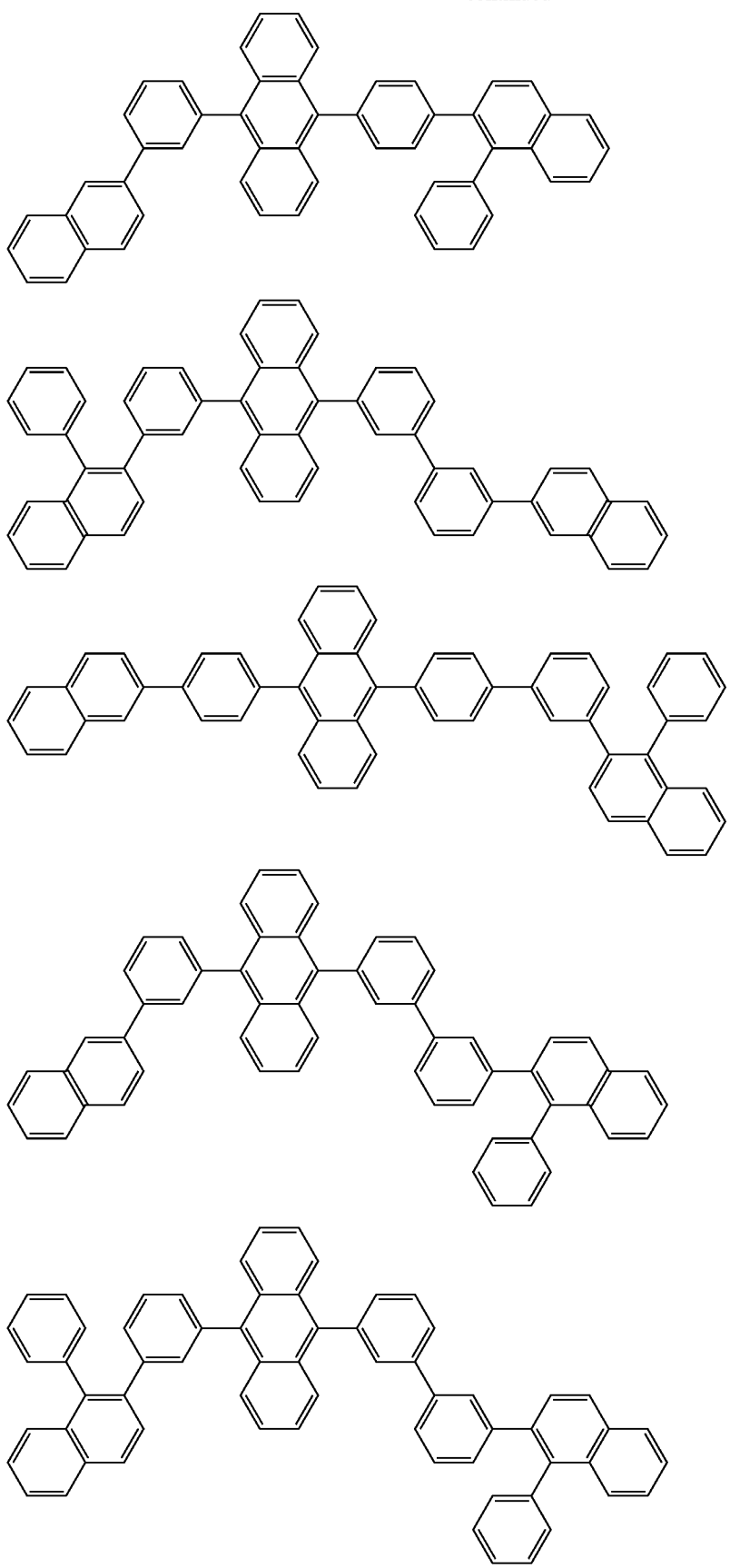

-continued
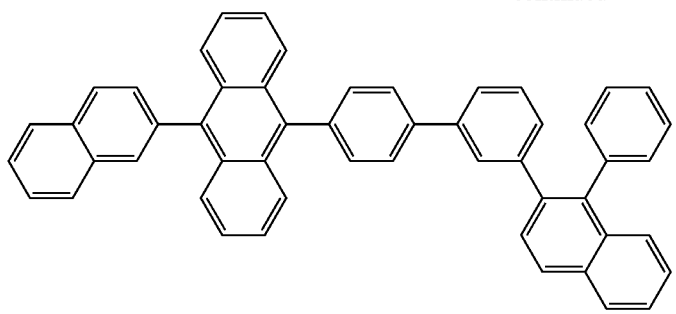
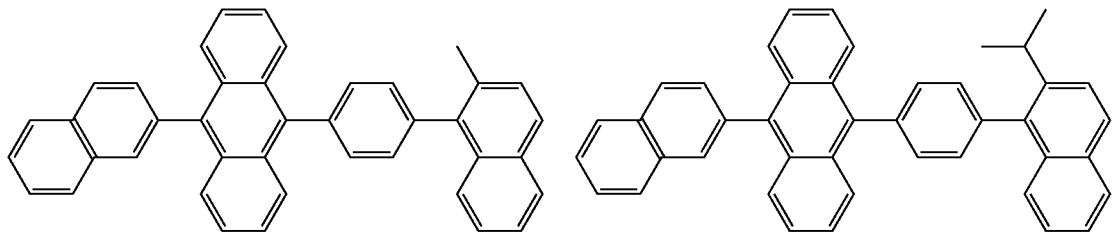
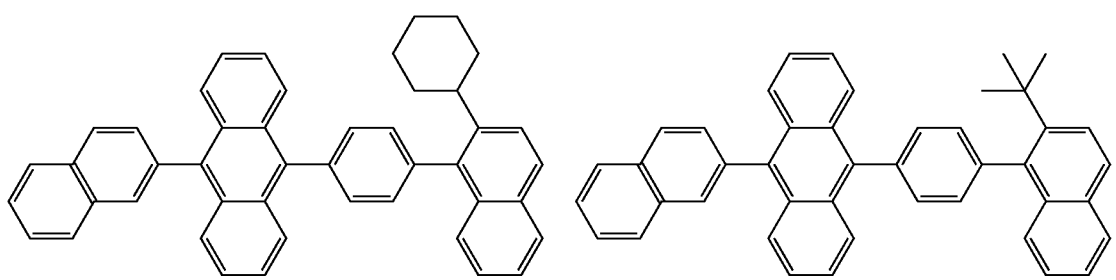
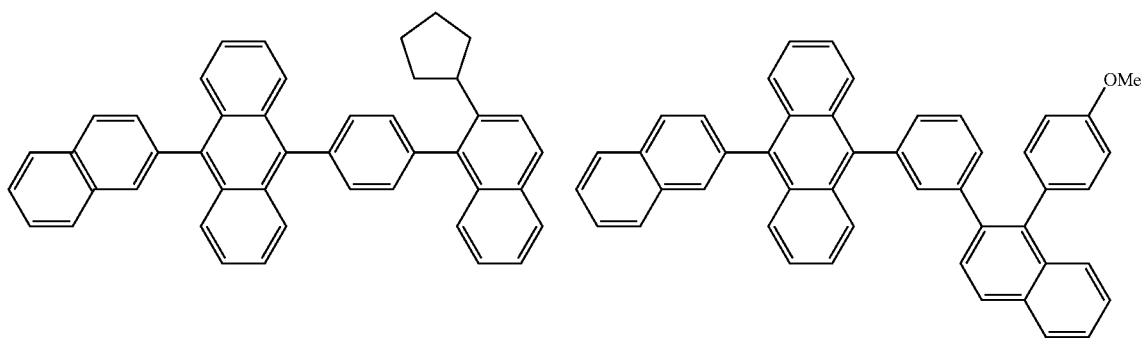
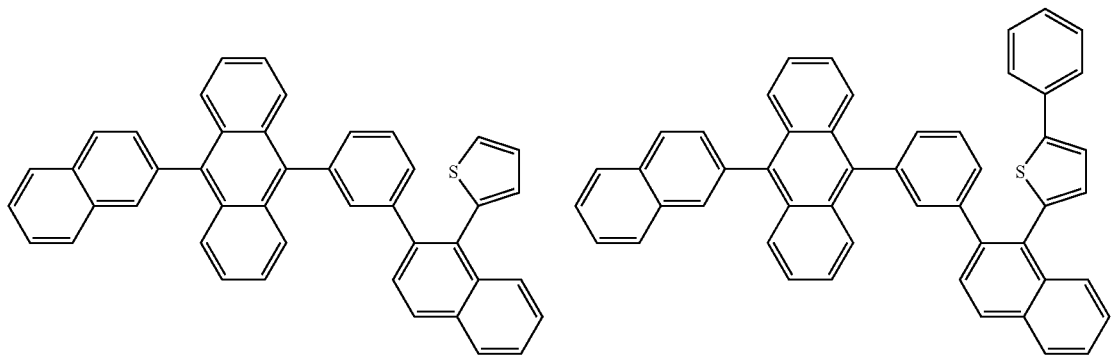

-continued
| 31 | 32 |
|---|---|
| 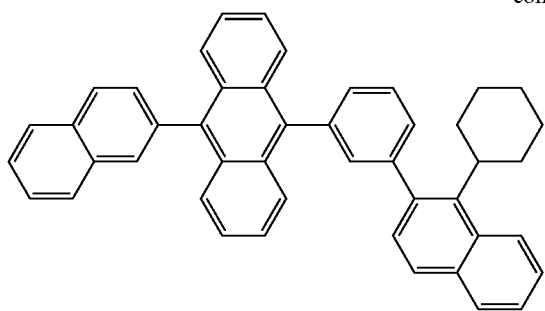 | 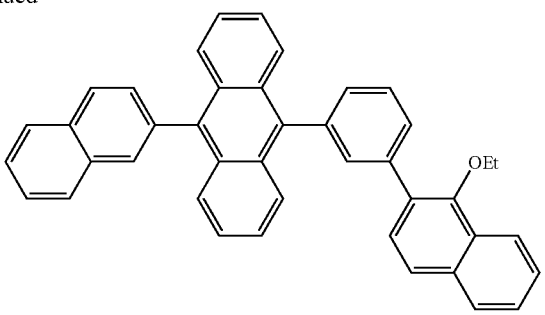 |
| 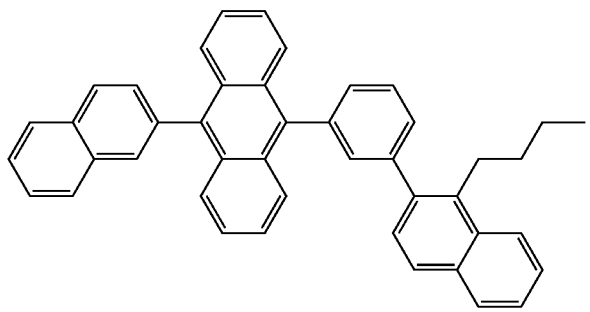 | 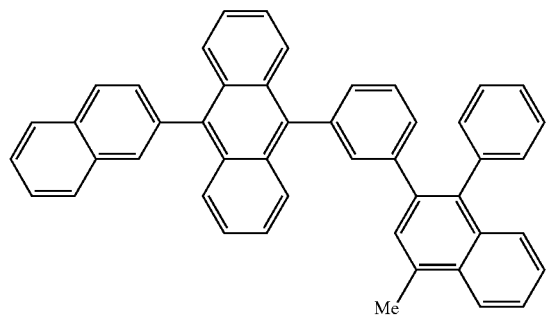 |
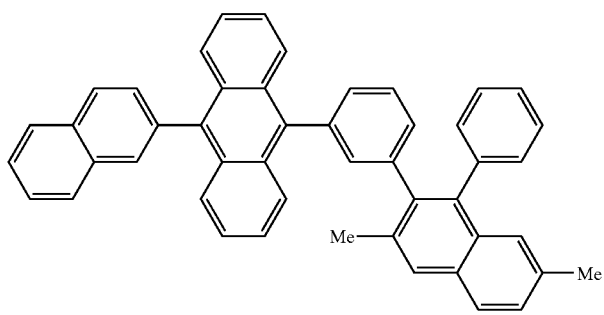
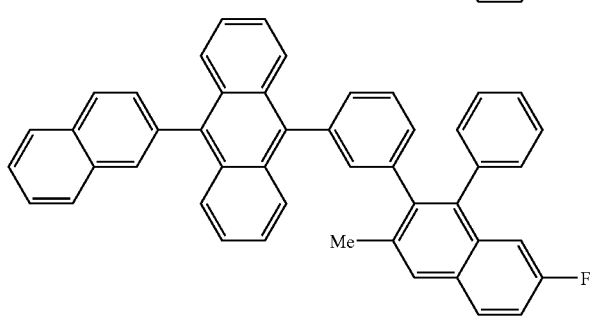
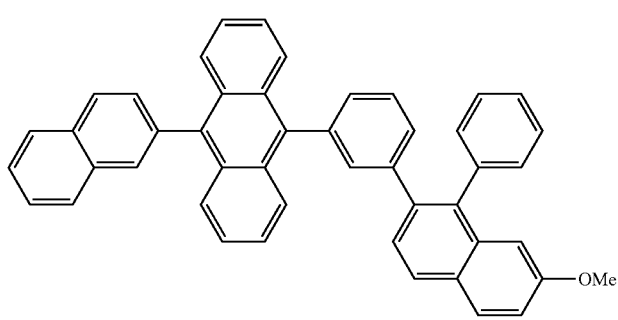

-continued
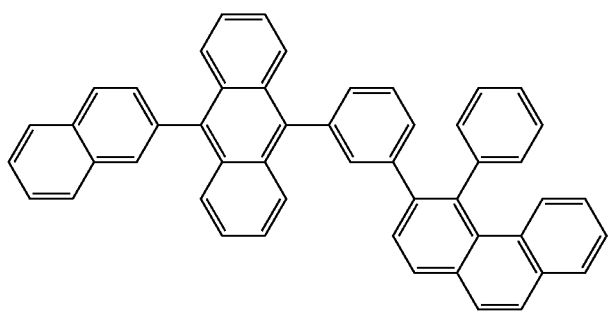
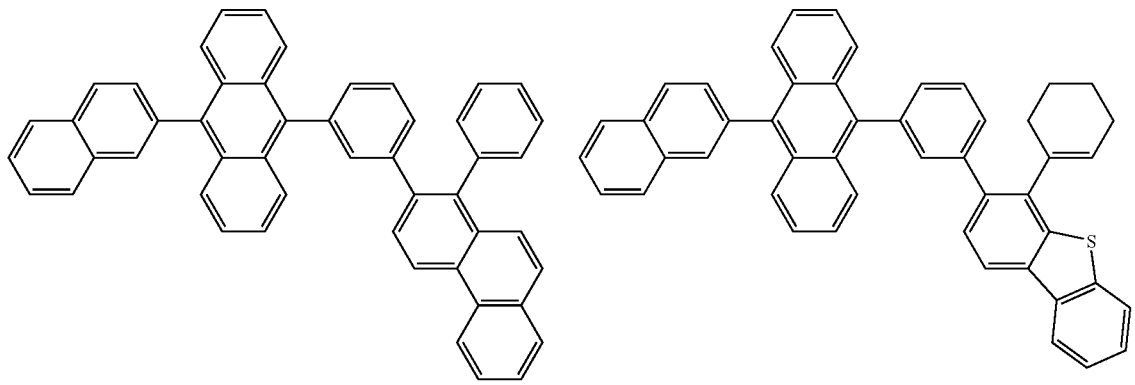
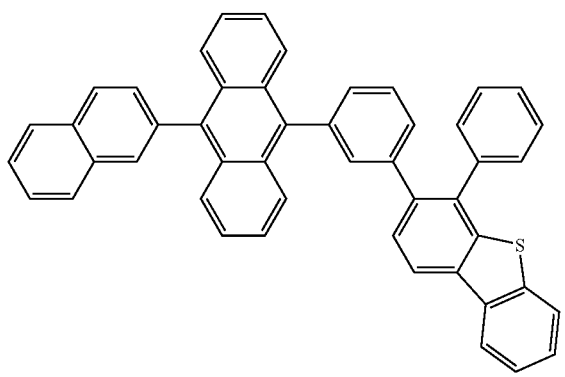
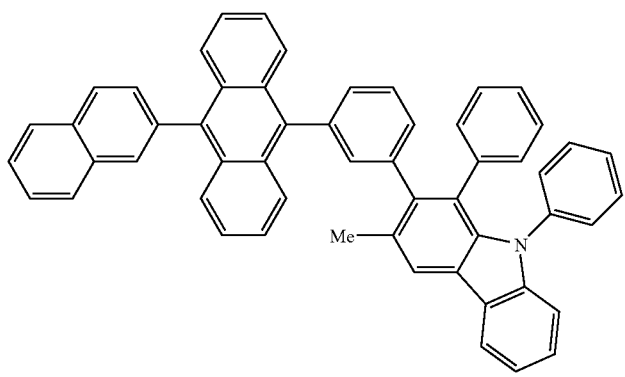

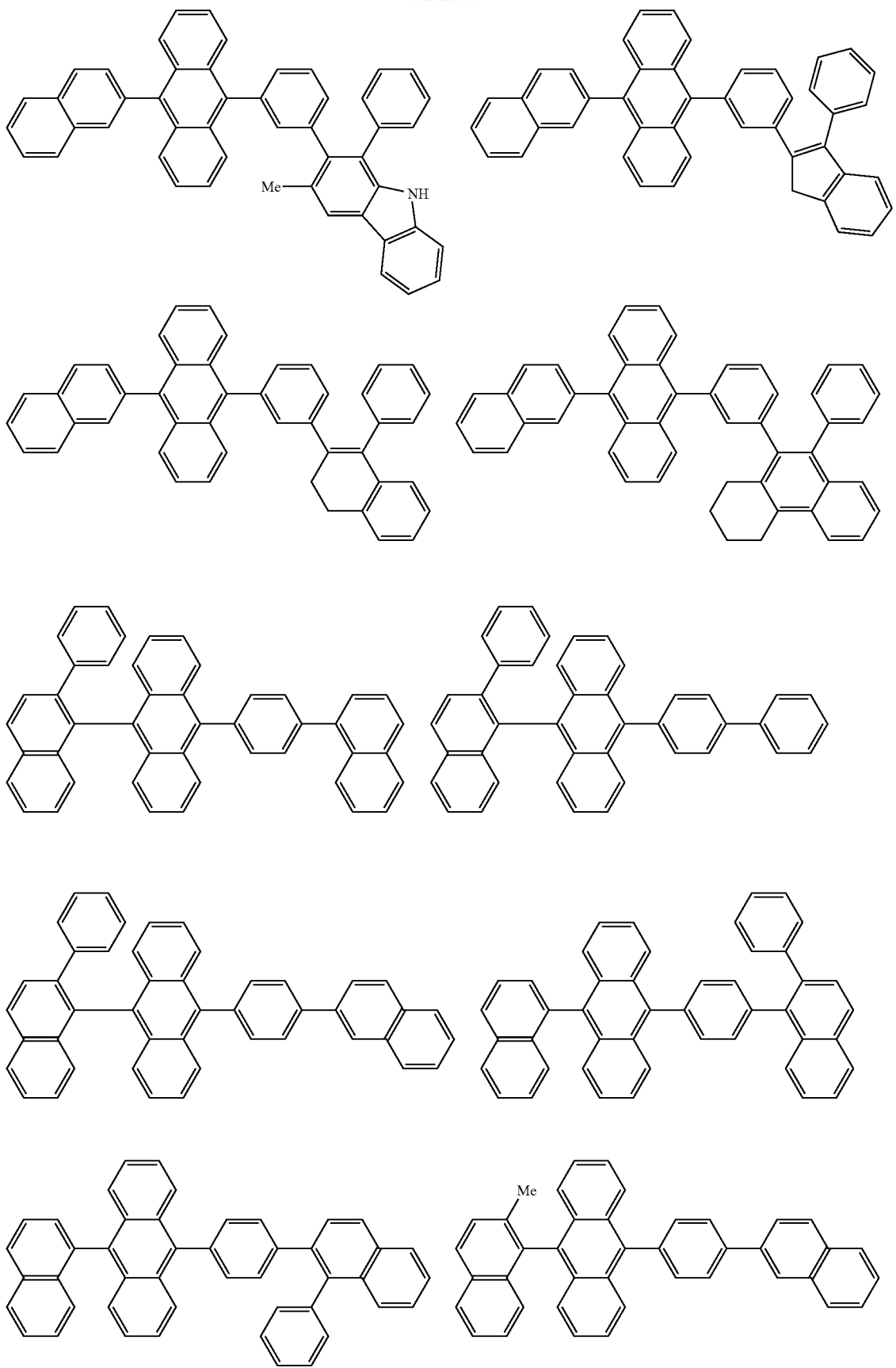

-continued
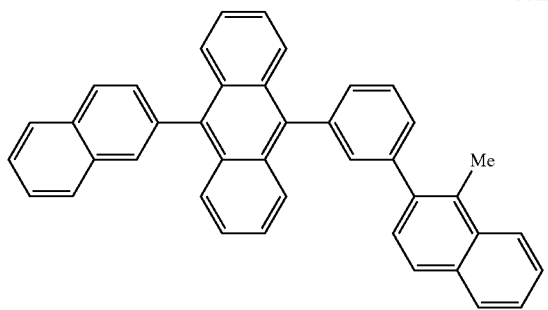
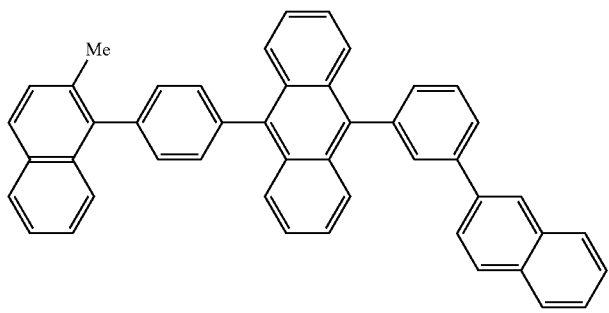
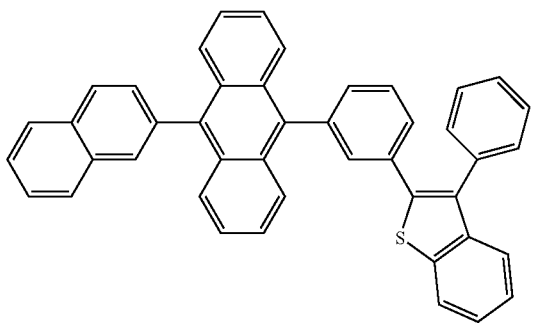
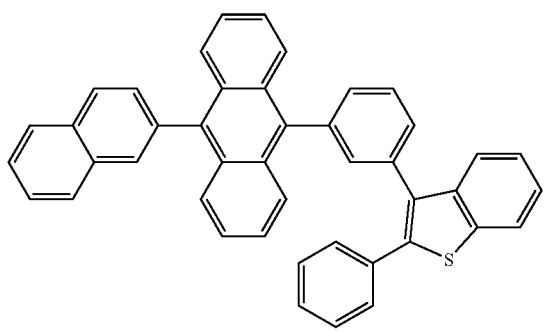
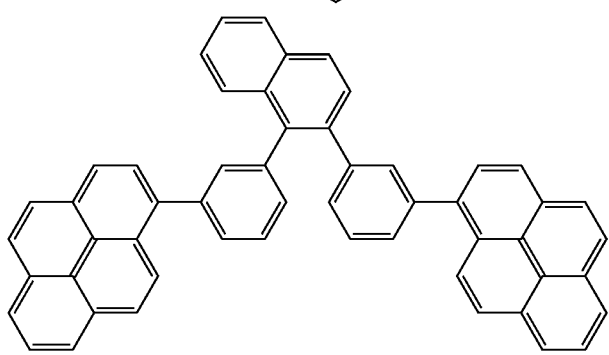
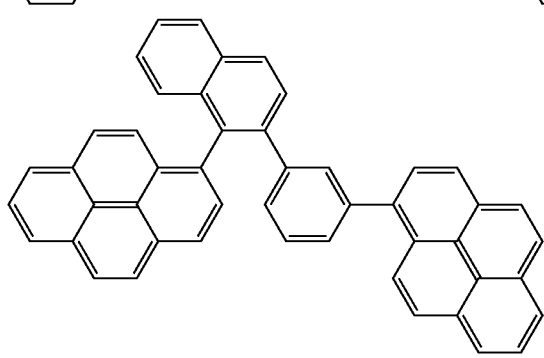

-continued
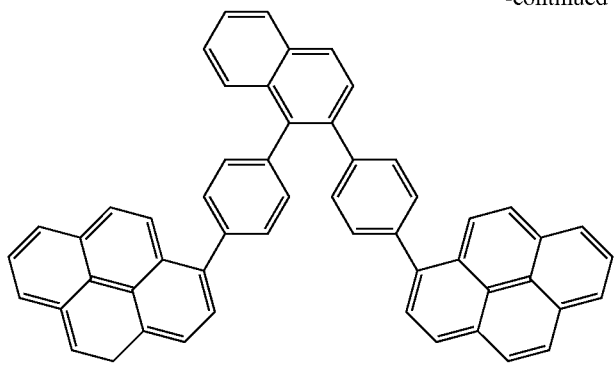
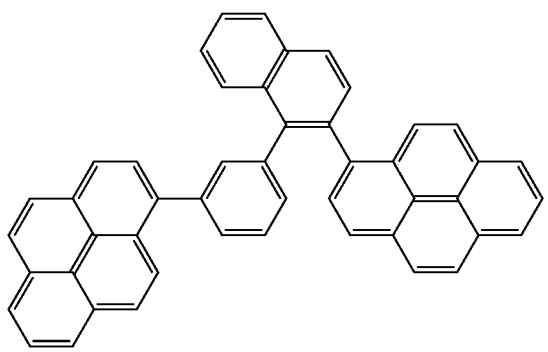
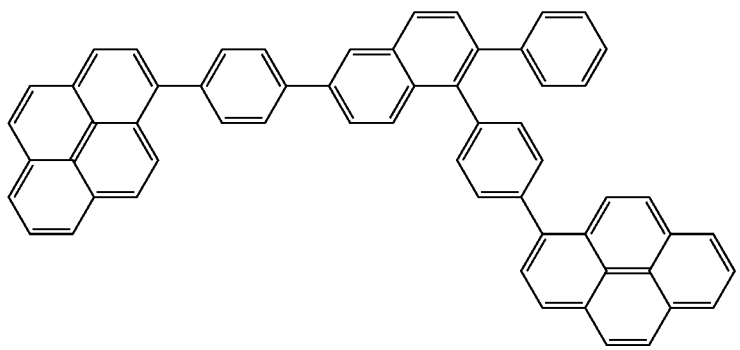
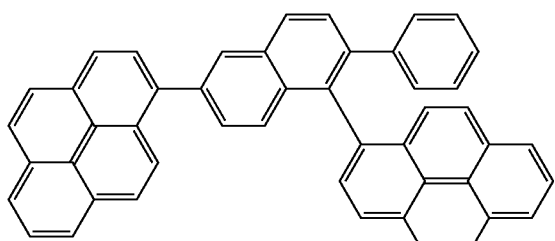
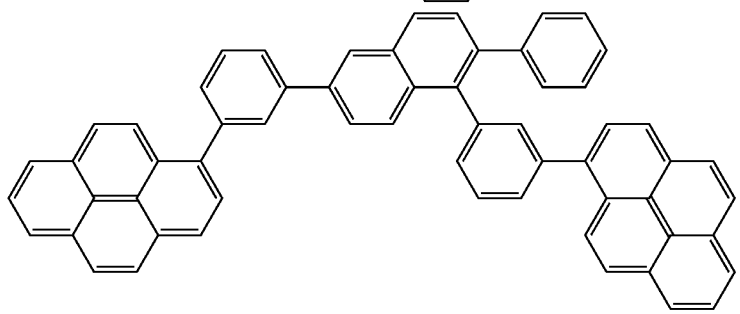

-continued
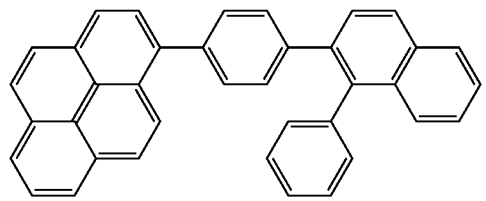
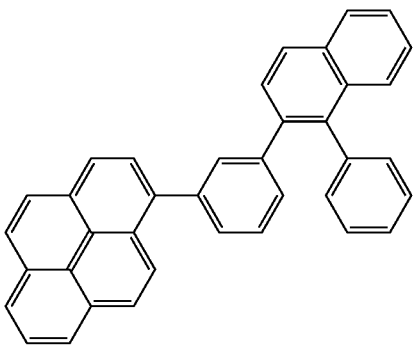
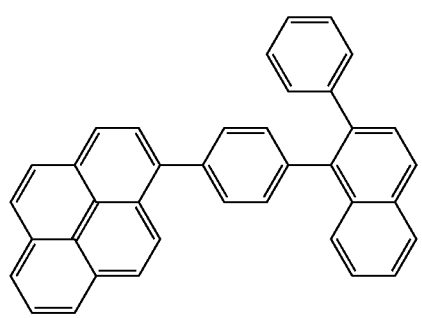
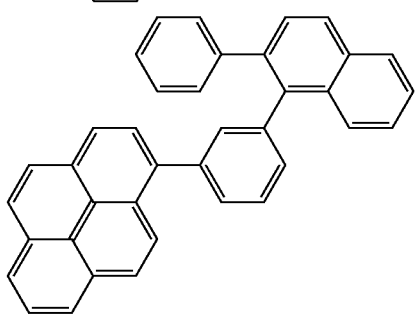
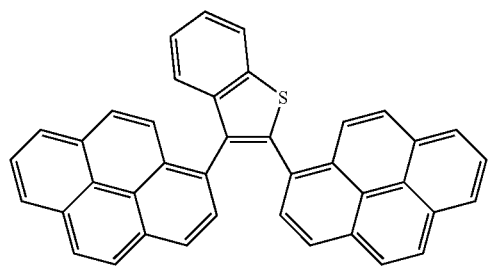
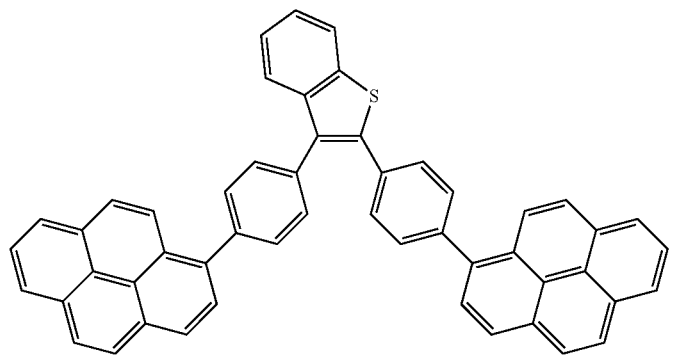
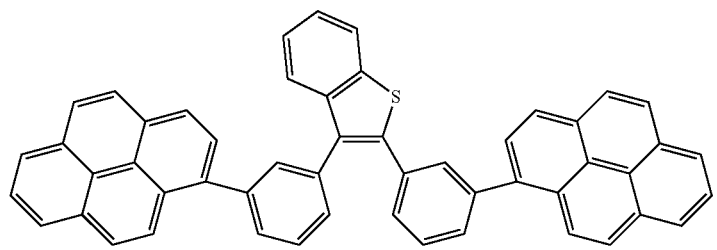

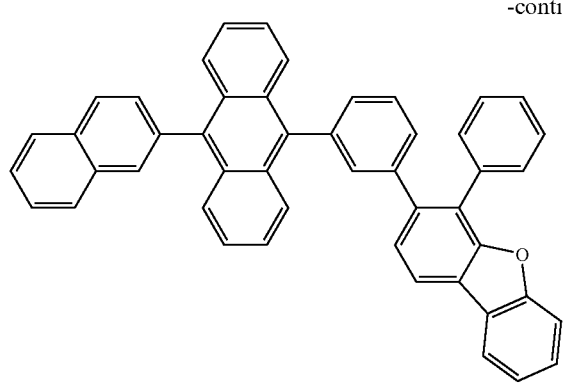
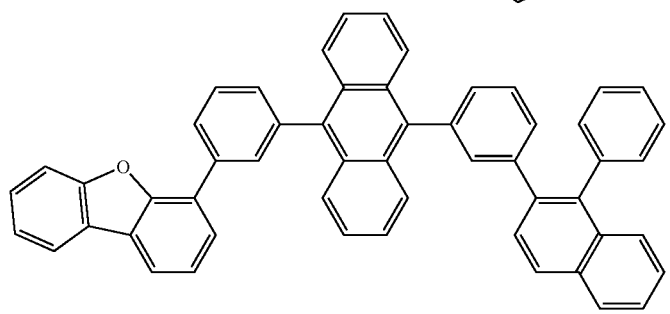
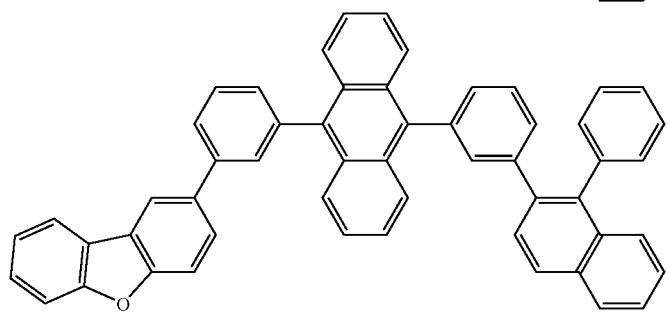
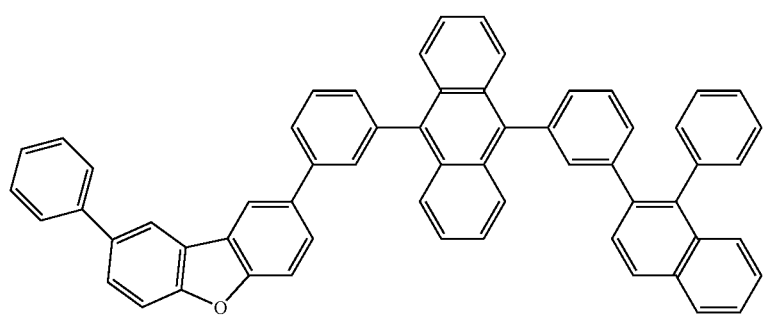
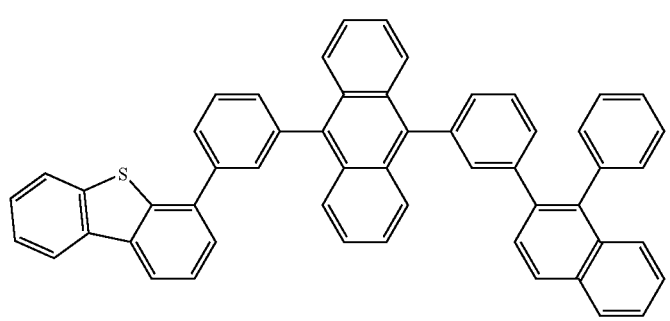

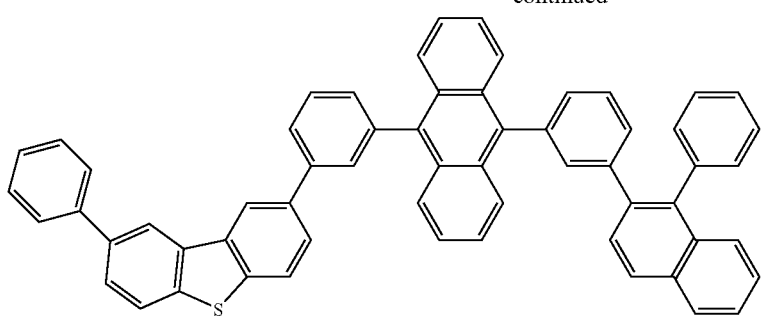
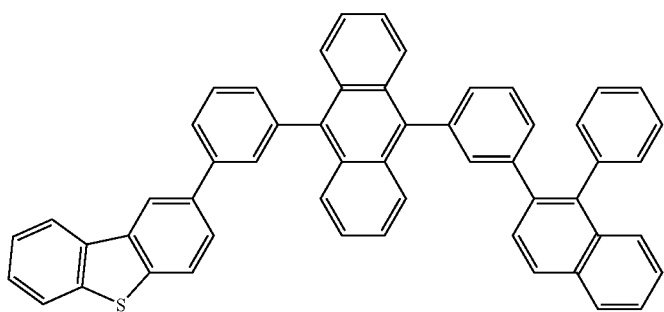
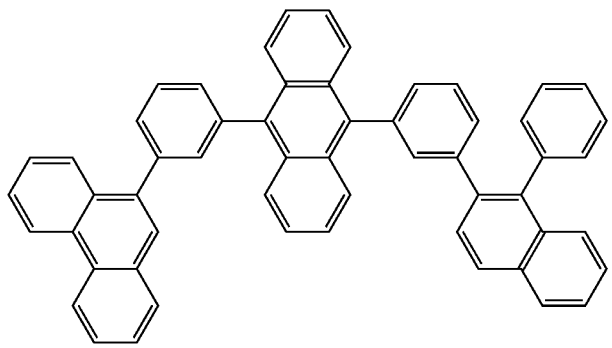
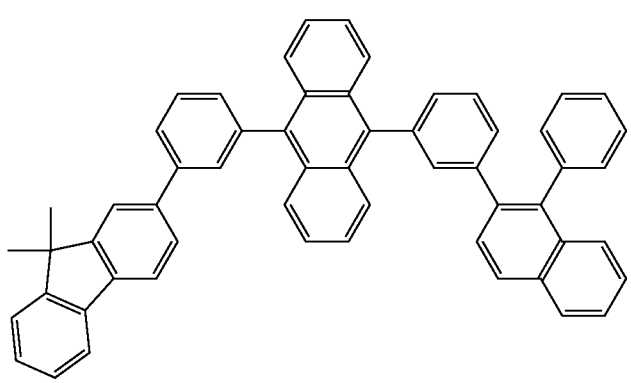

-continued
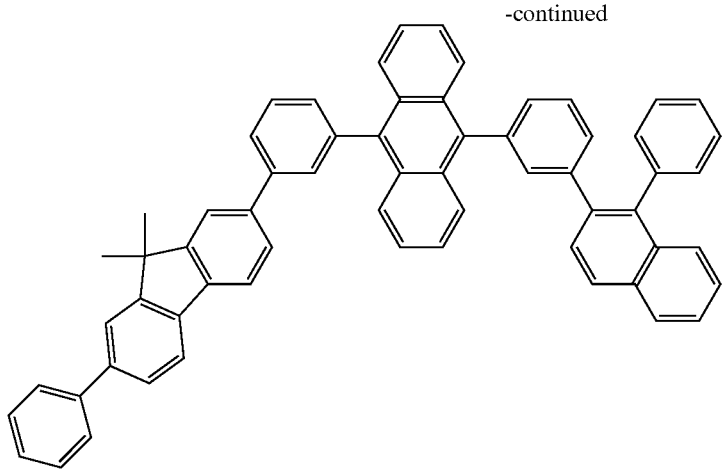
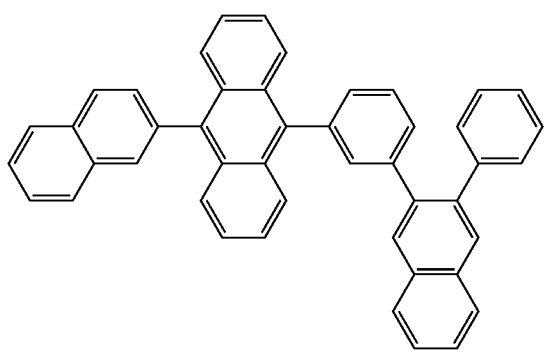
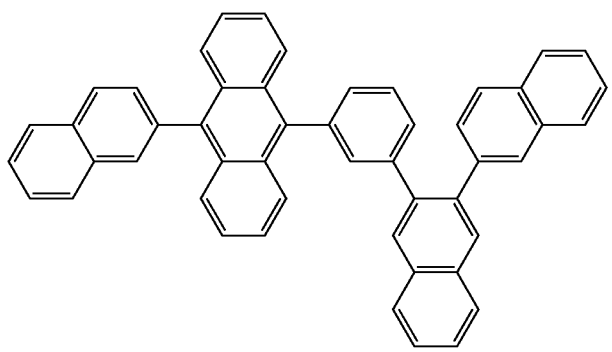
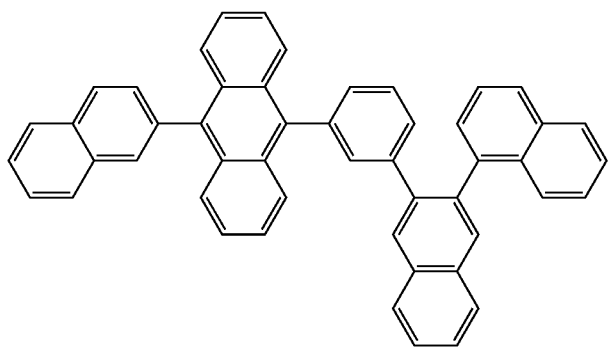

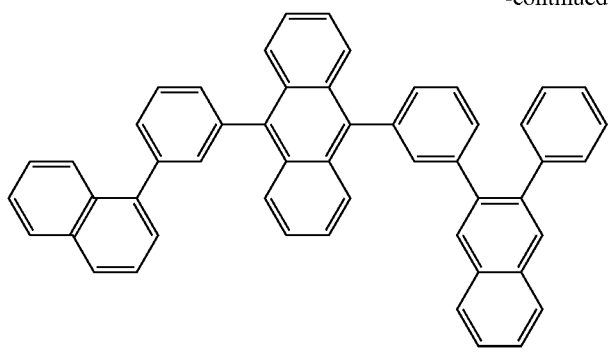
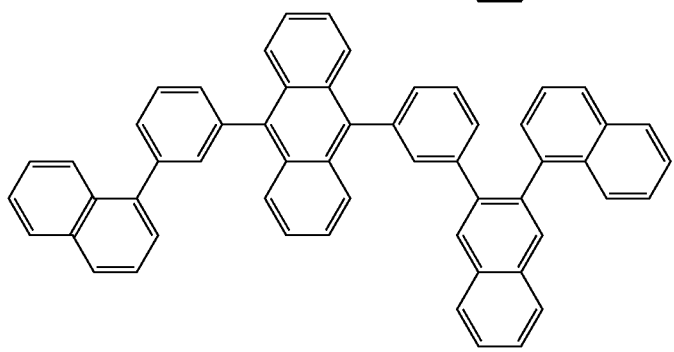
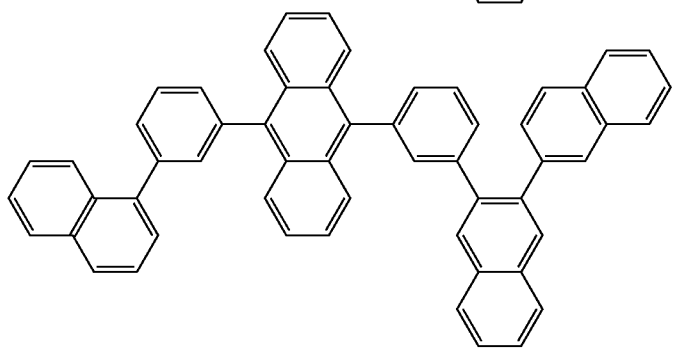
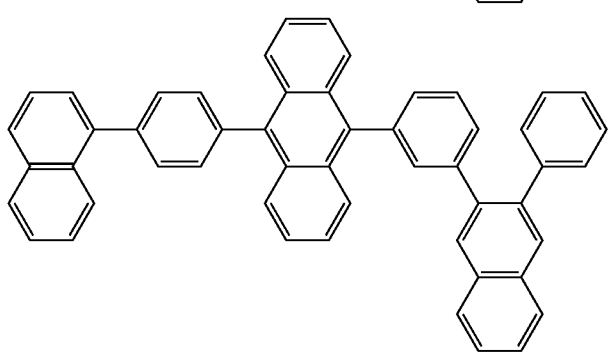
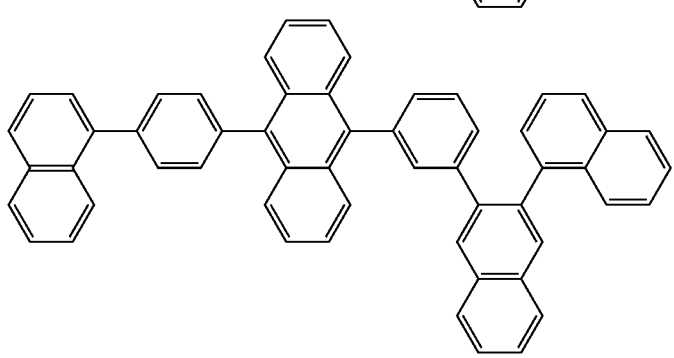

-continued
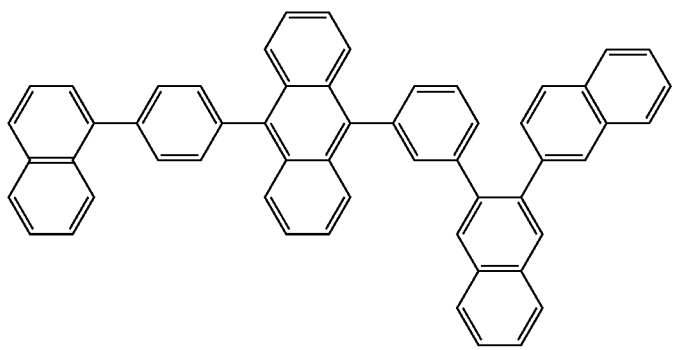
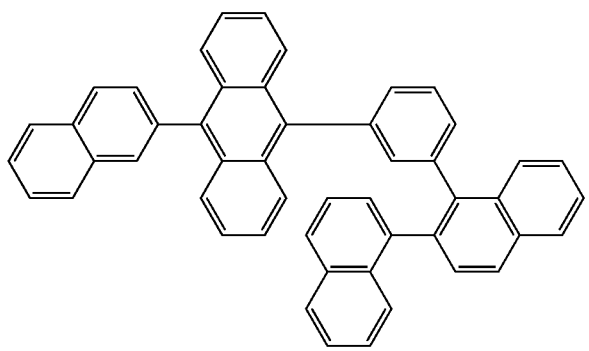
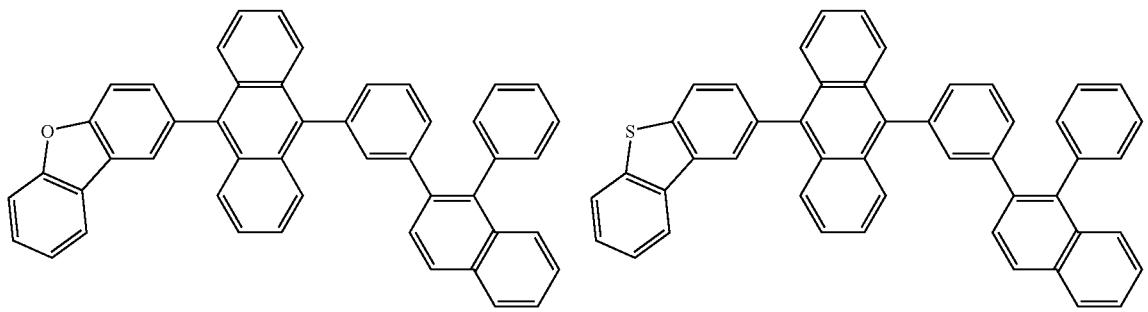
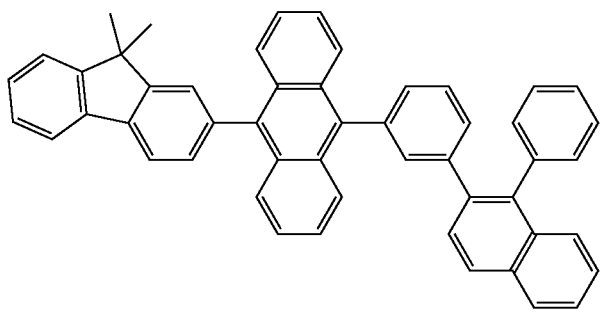
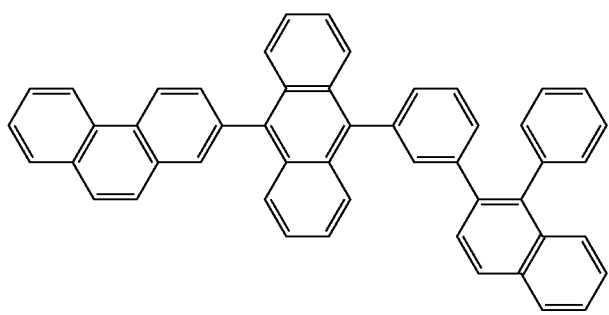

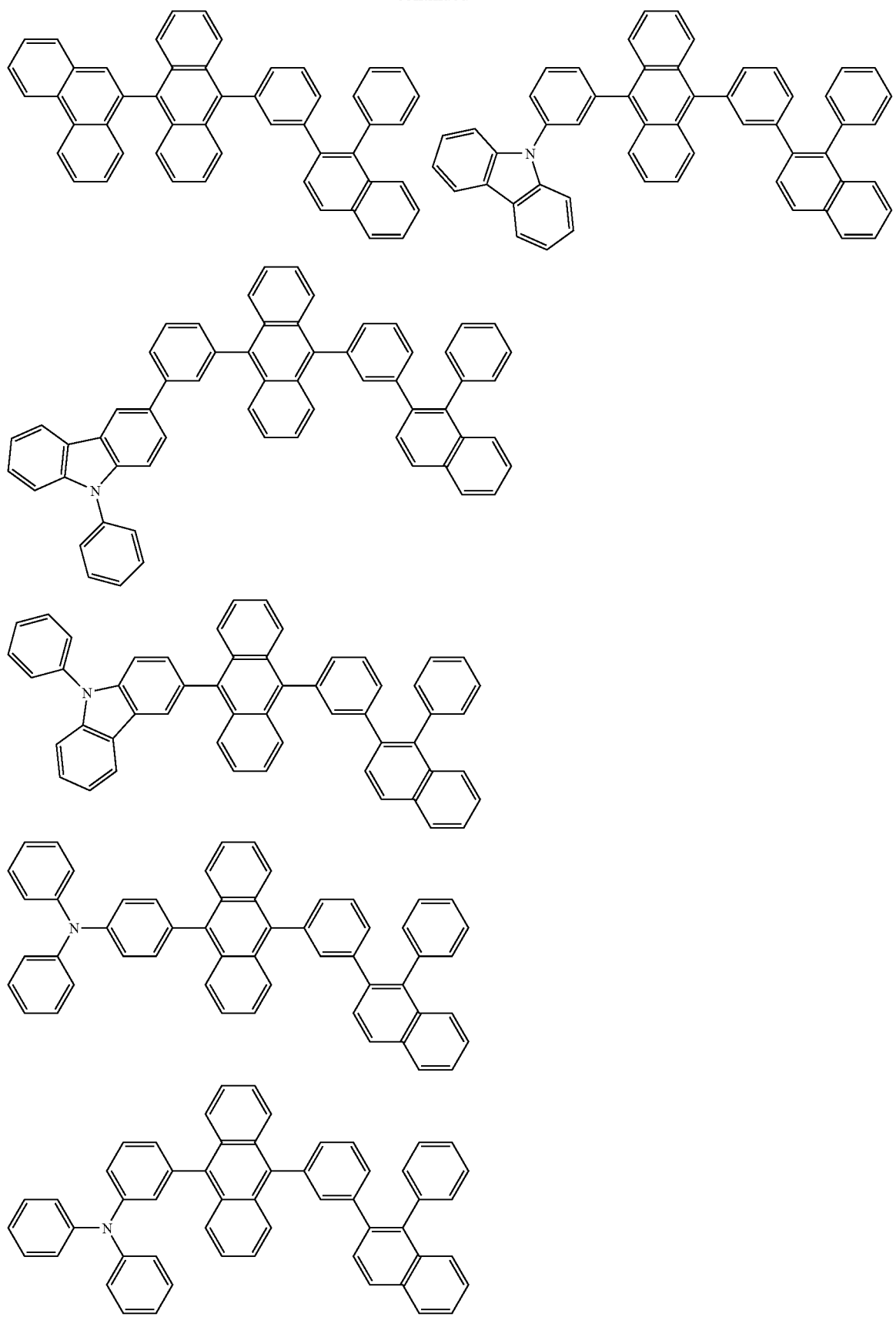

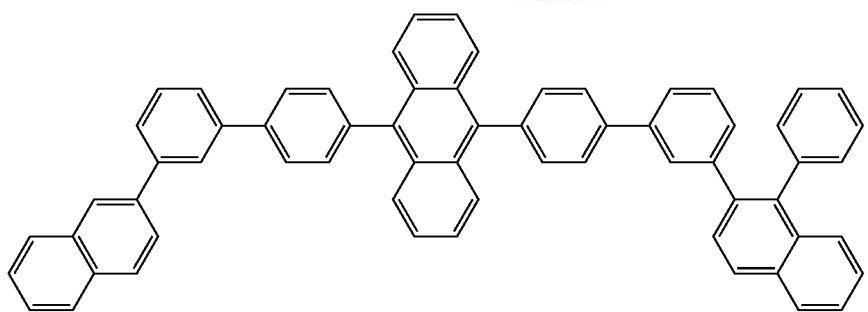
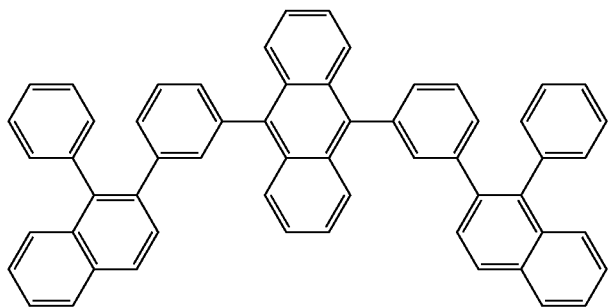
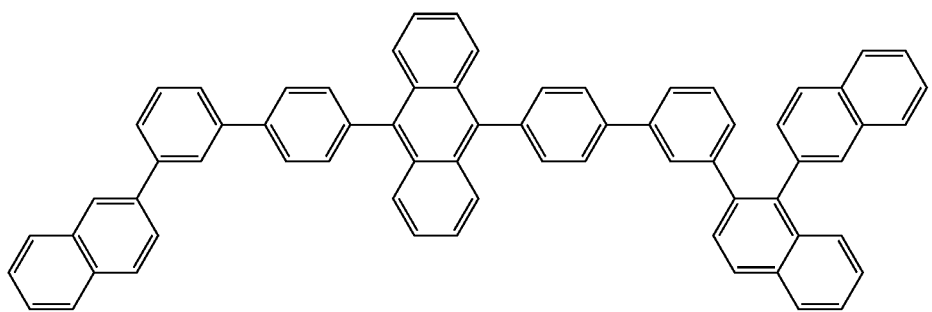
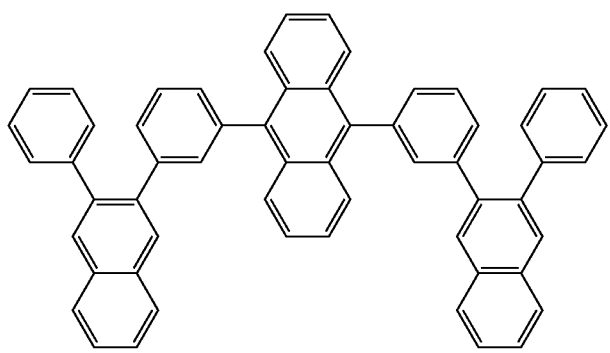
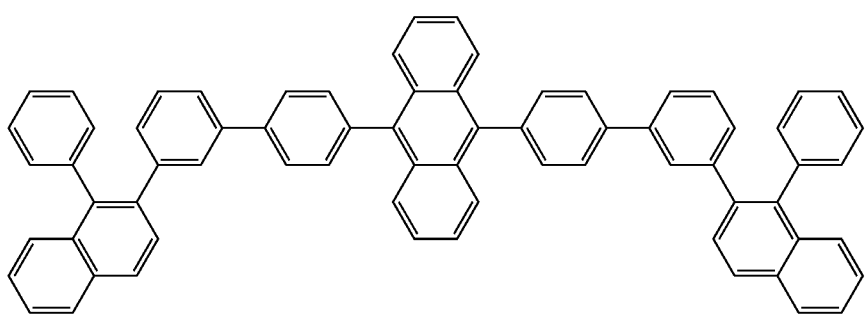

-continued
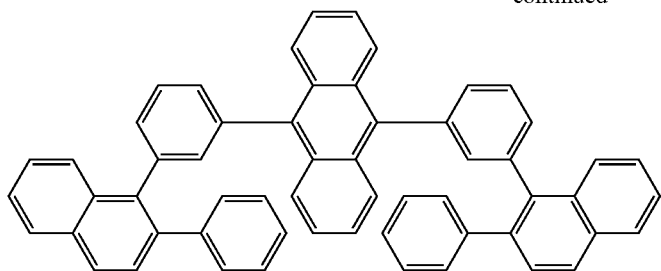
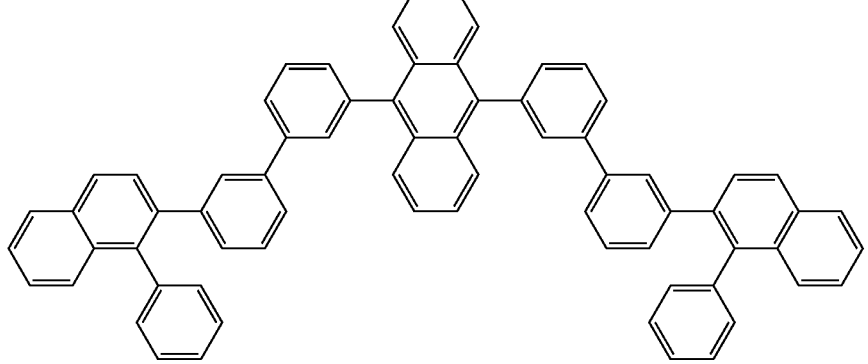
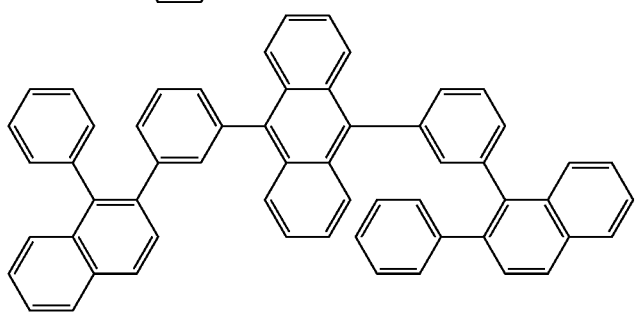
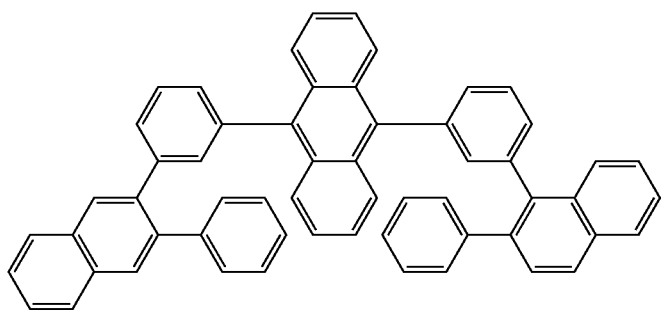
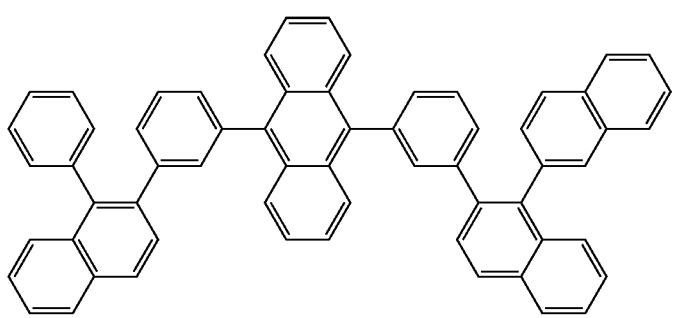

-continued
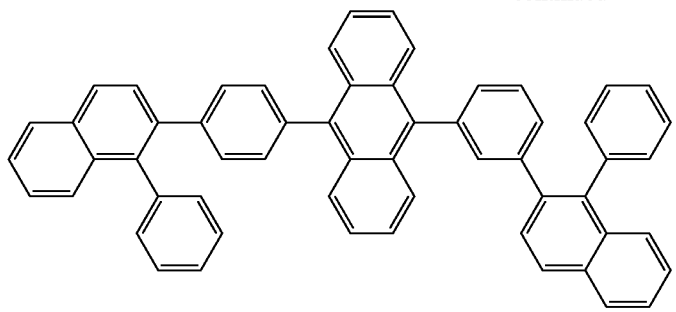

-continued
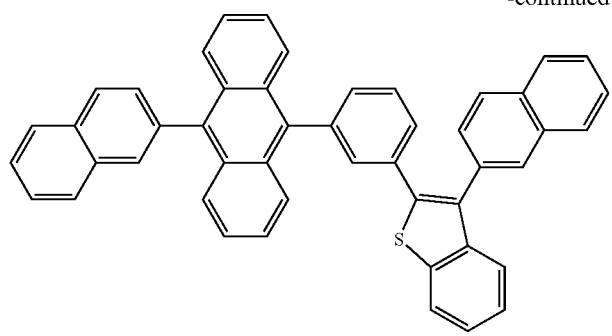
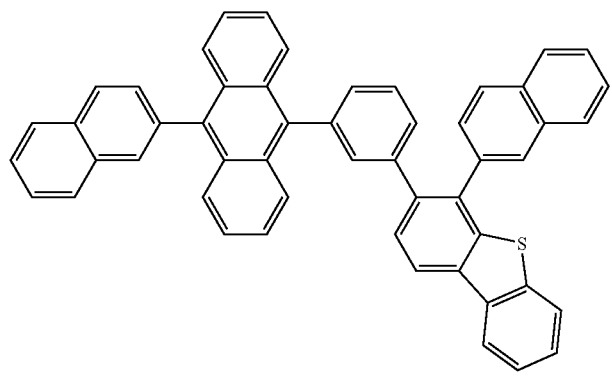
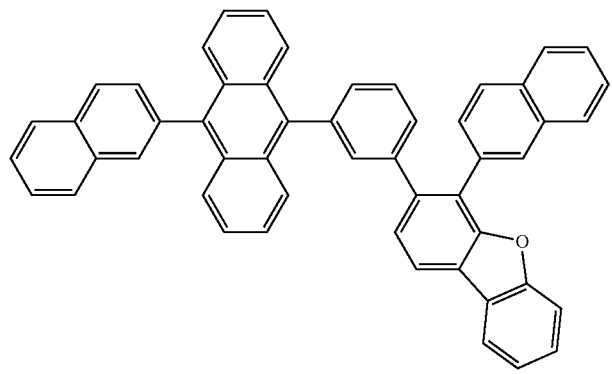
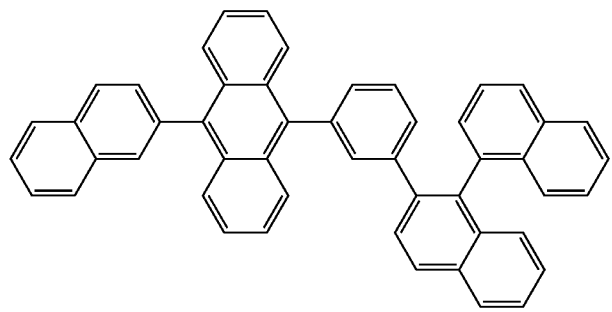
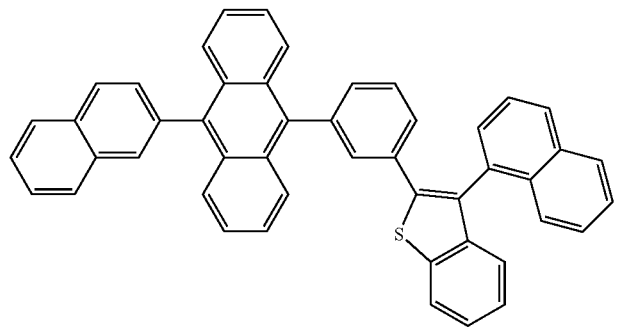

-continued
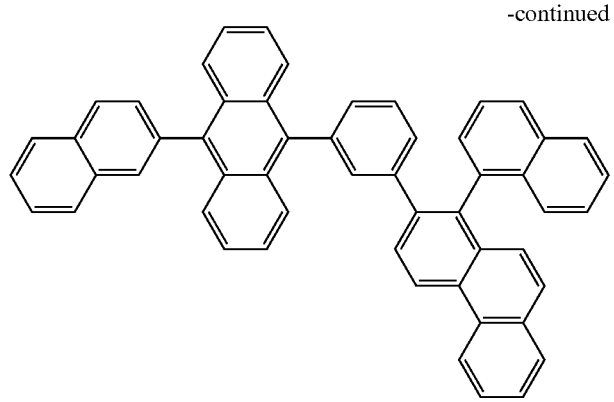
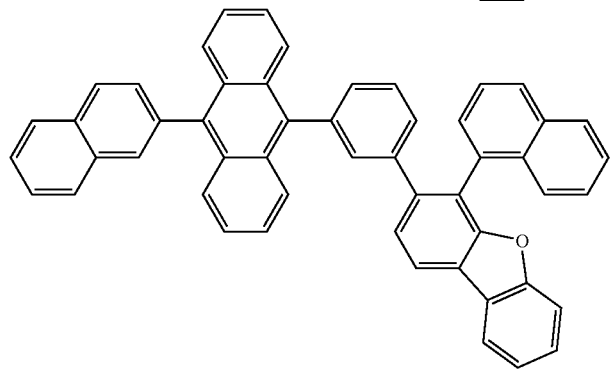
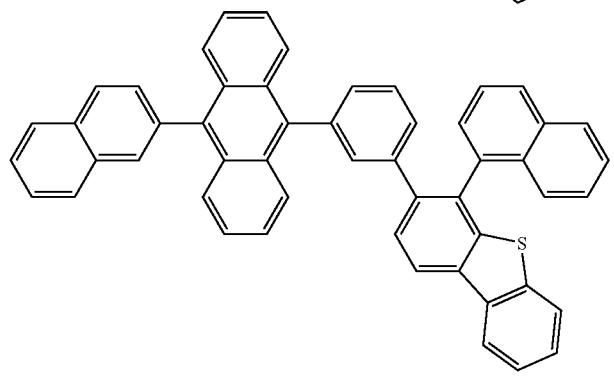
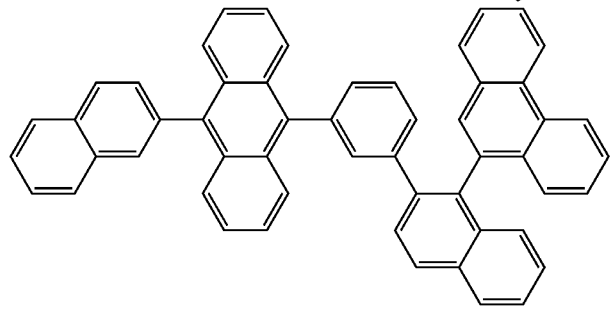
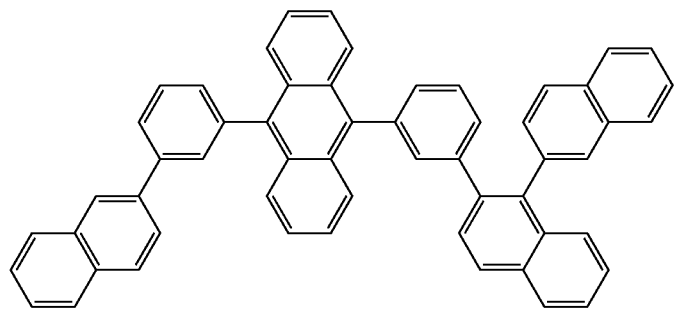

-continued
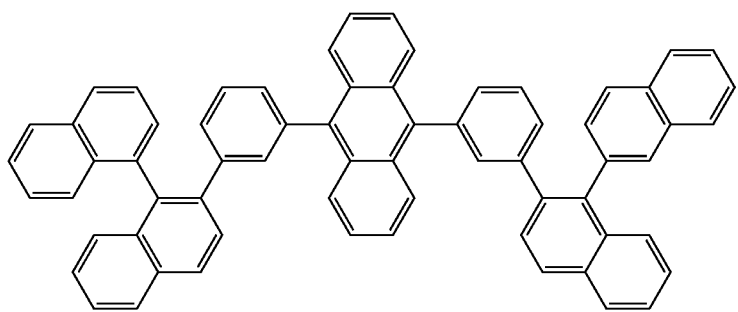
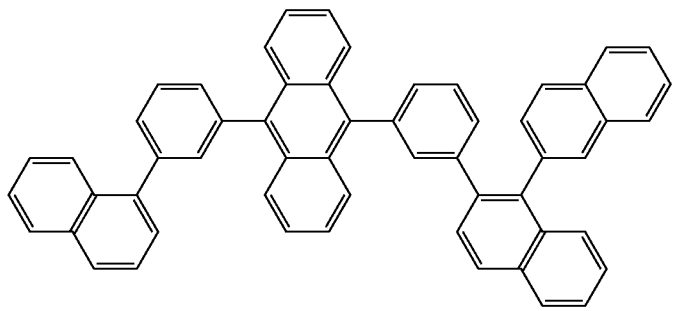
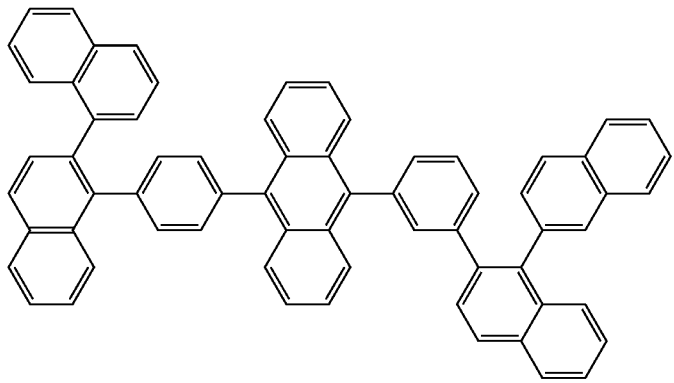
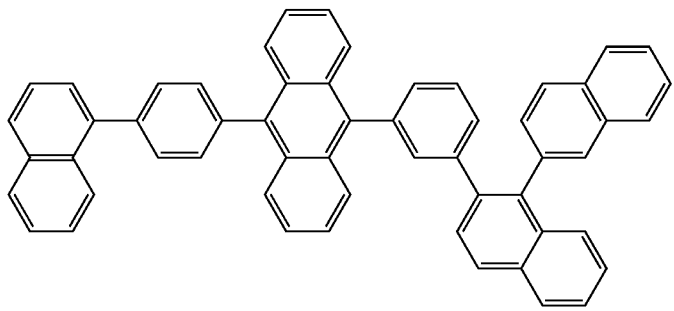
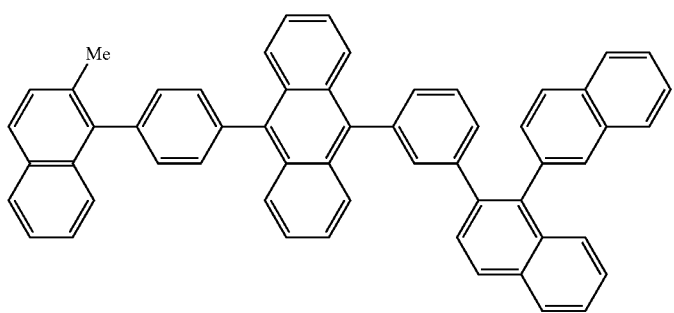

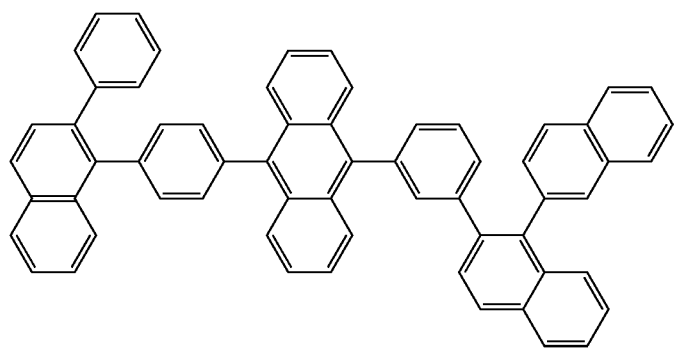
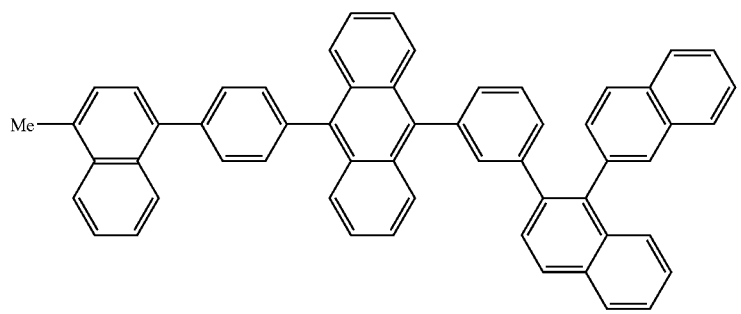
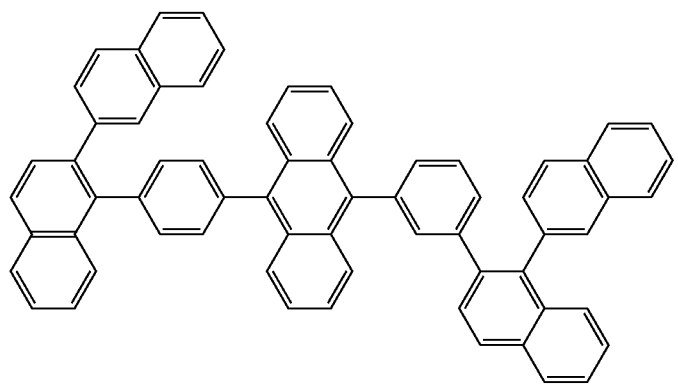
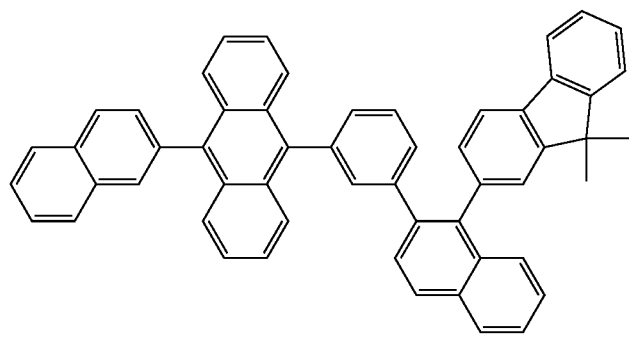
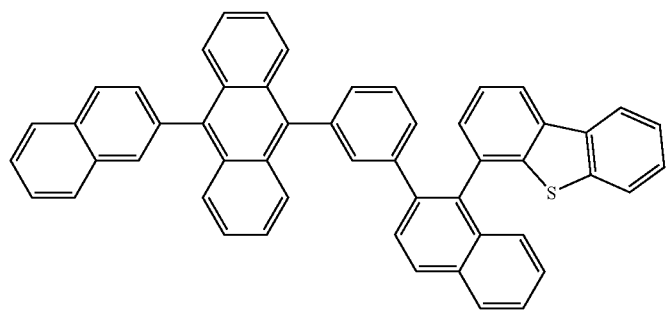

-continued
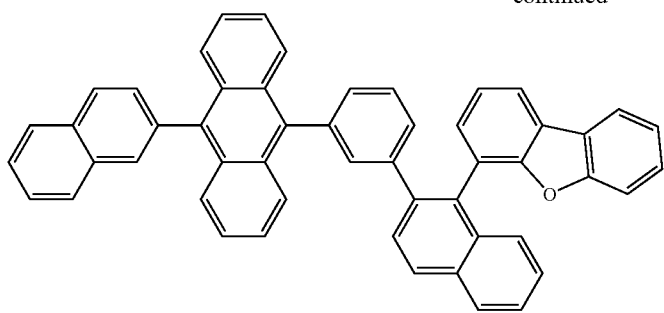
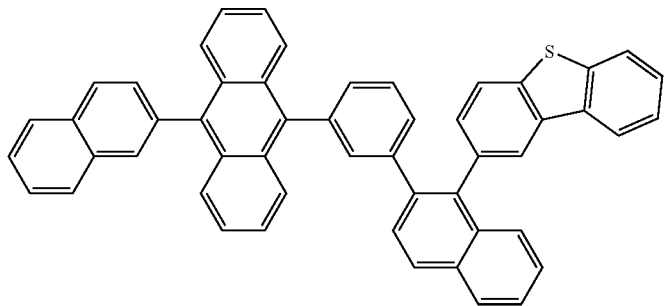
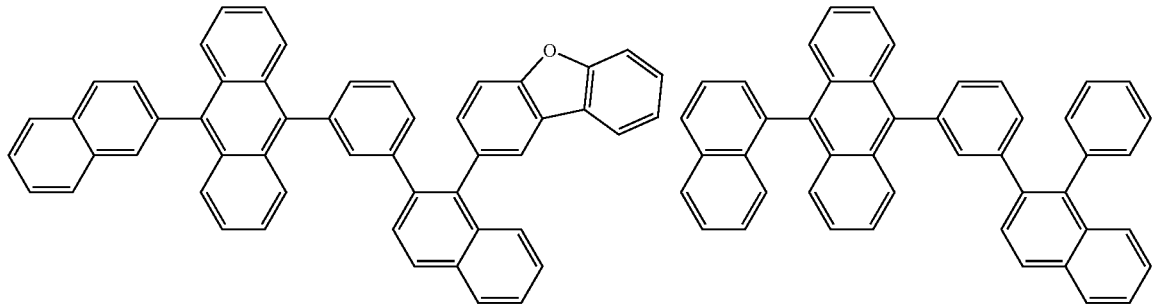
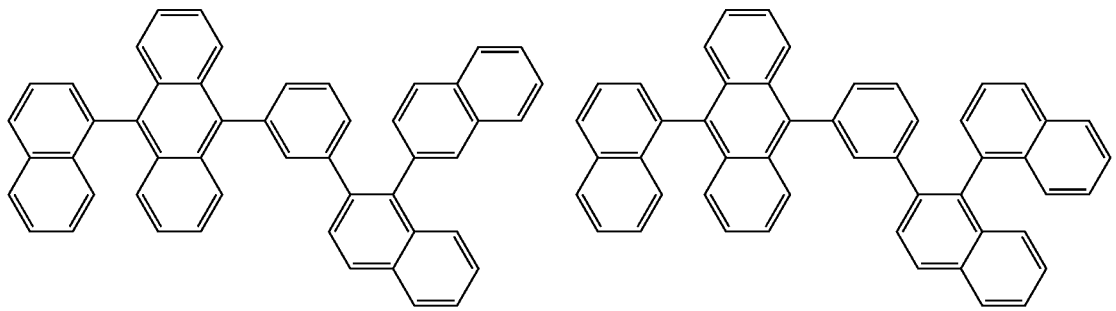
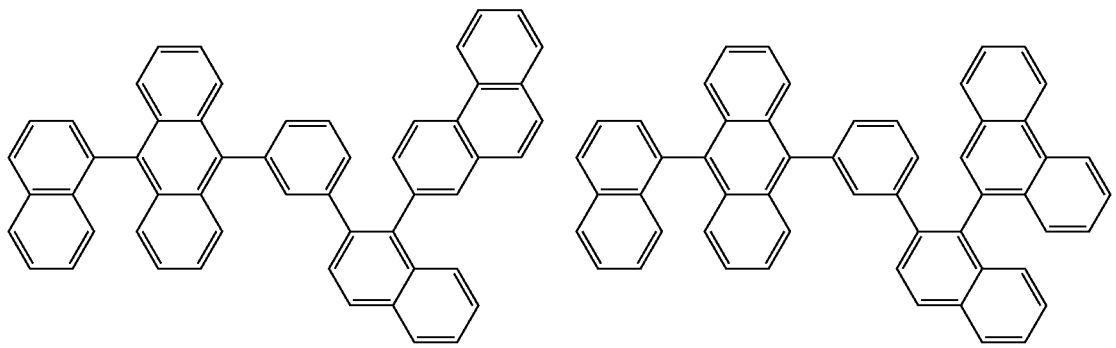

-continued
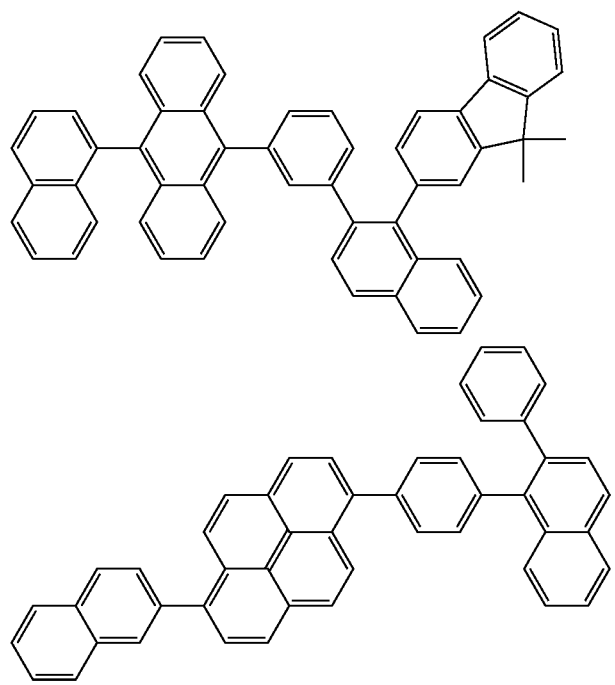
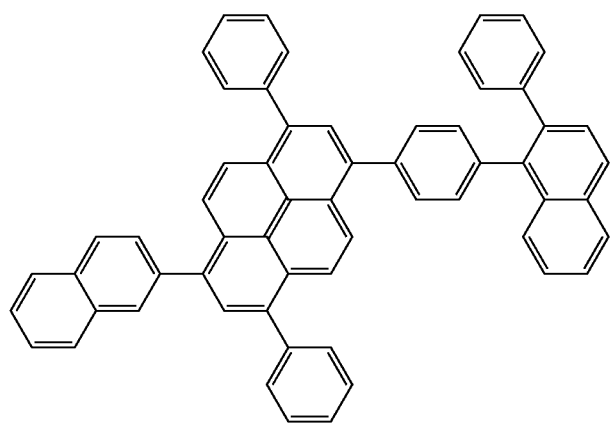
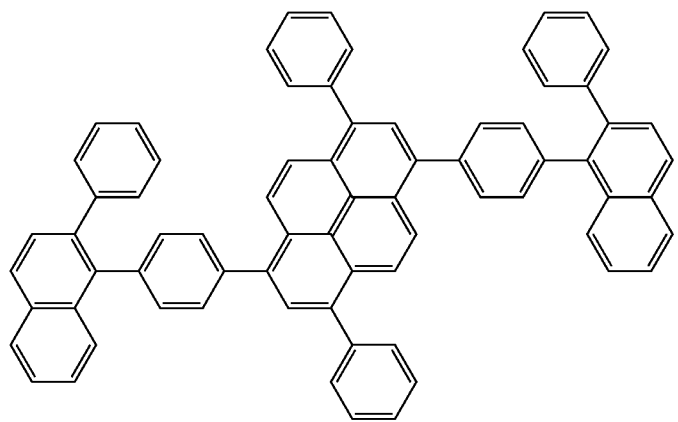

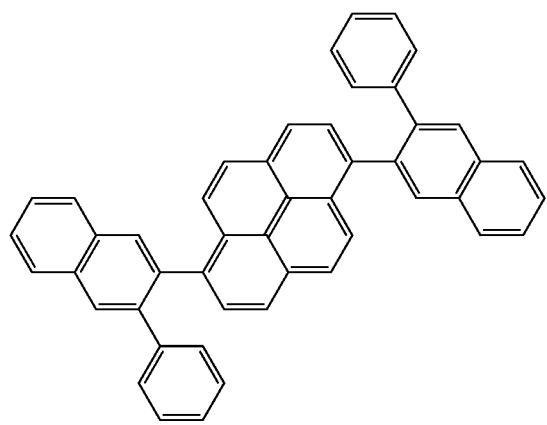
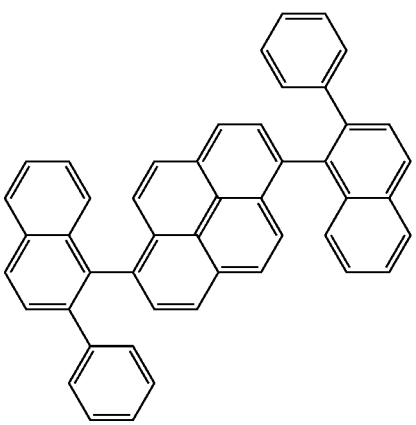
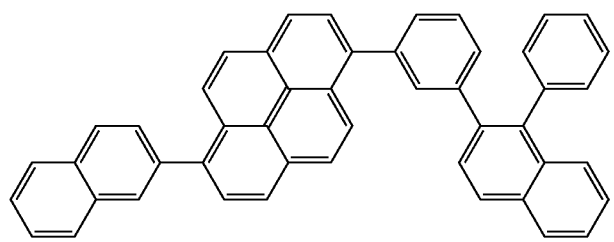
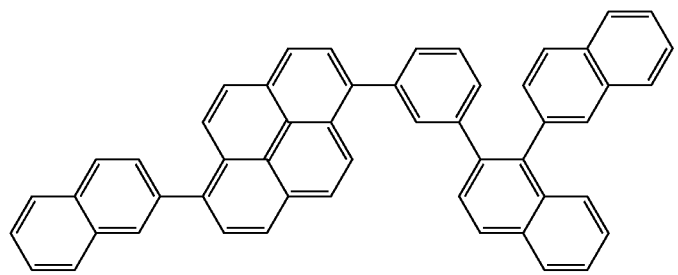
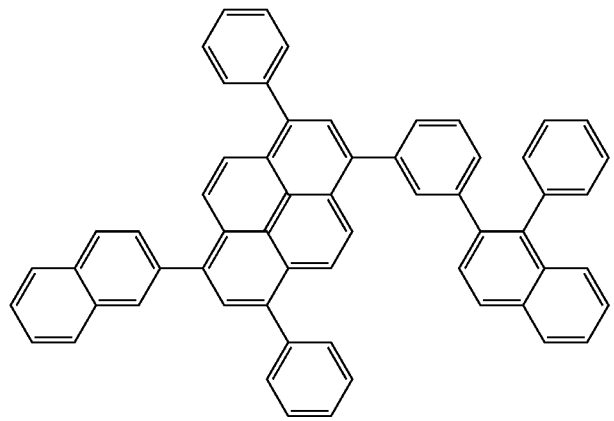
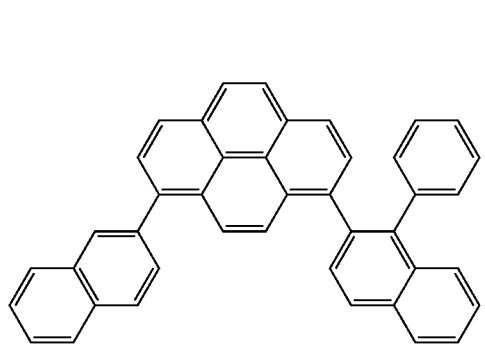
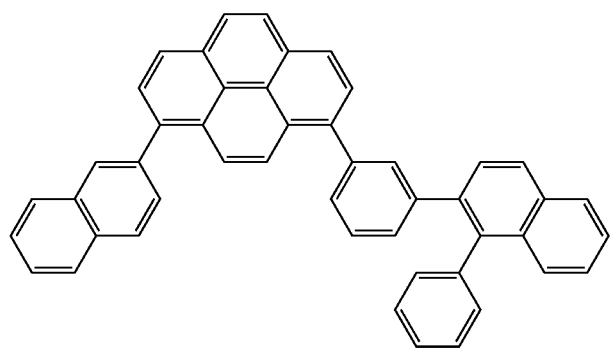

-continued
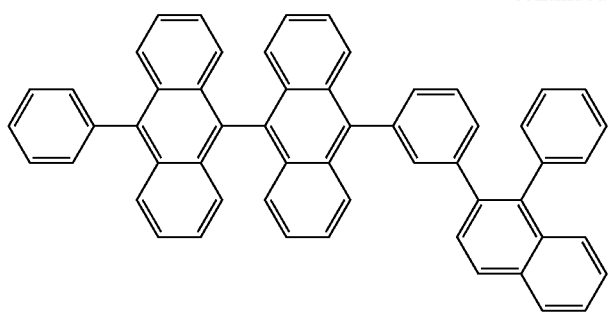
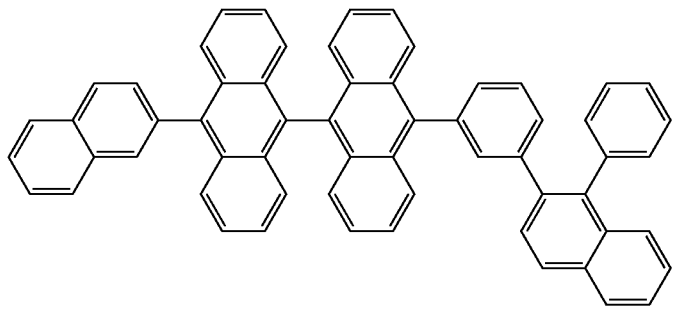
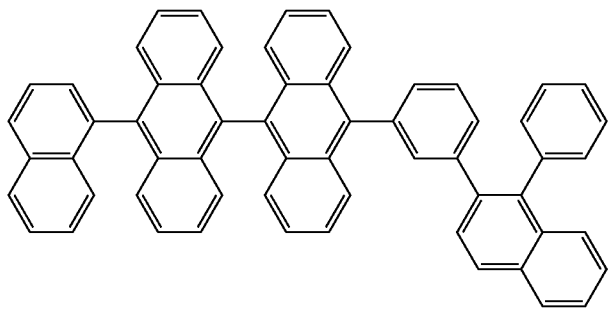
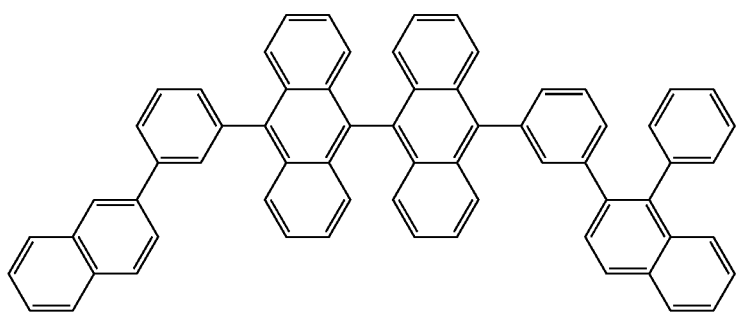
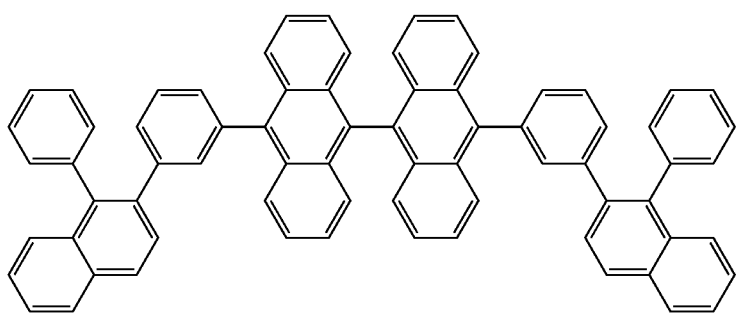

-continued

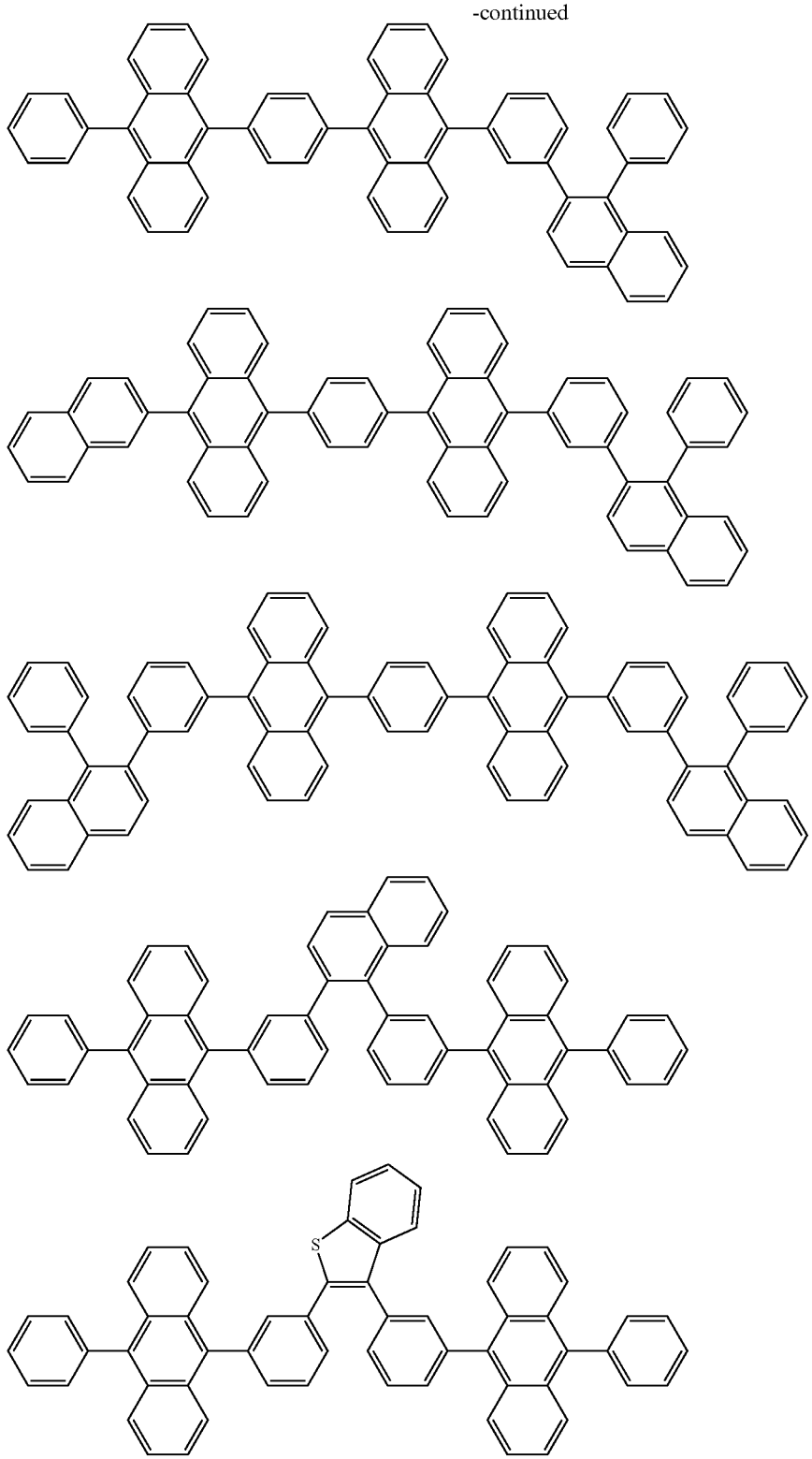

The present invention provides a polymer compound having repeating units at least part of which are structures derived from the polycyclic ring assembly compound in the foregoing description. The polymer compound of the present invention can be synthesized in accordance with the process (polycondensation reaction, coupling reaction, radical reaction, living polymerization, etc.) usually employed for polymer synthesis, and so long as it is convenient in the fabrication of the device, no special restriction is necessary for the structures or so.

The organic EL device of the present invention is composed of one or more organic thin film layers including at least one light emitting layer and interposed between a cathode and an anode, wherein at least one of the organic thin film layers contains the foregoing polycyclic ring assembly compound or the foregoing polymer compound as a light emitting material.

In the organic EL device of the present invention, the light emitting layer preferably contains either the polycyclic ring assembly compound or the above polymer compound as its host material.

The organic EL device of the present invention preferably contains a phosphorescent dopant and/or a fluorescent dopant.

The organic EL device of the present invention preferably contains an arylamine compound and/or a styrylamine compound.

The organic EL device of the present invention preferably contains a metal-complex compound.

Following is a description regarding with a device construction about the organic EL device of the present invention.

Typical examples of the construction in the organic EL device of the present invention are shown below.
(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;
(9) An anode/an insulating layer/a light emitting layer/an insulating layer/a cathode;
(10) An anode/an inorganic semiconductor layer/an insulating layer/a light emitting layer/an insulating layer/a cathode;
(11) An anode/an organic semiconductor layer/an insulating layer/a light emitting layer/an insulating layer/a cathode;
(12) An anode/an insulating layer/a hole injecting layer/a hole transporting layer/a light emitting layer/an insulating layer/a cathode; and
(13) An anode/an insulating layer/a hole injecting layer/a hole transporting layer/a light emitting layer/an electron injecting layer/a cathode.

Among the above constructions, construction (8) is usually preferable though not limited to. Further, in the organic EL device of the present invention, although the polycyclic ring assembly compound represented by the general formula (1) may be used for any organic layer, it is preferable that the polycyclic ring assembly compound is contained in a light emitting region among the above-mentioned elements. It is particularly preferable that the polycyclic ring assembly compound is contained in the light emitting layer. The amount to be contained in the device is selected from 30 to 100% by mole.

In general, the organic EL device is fabricated on a substrate which transmits light. The substrate which transmits light is the substrate which supports the organic EL device. It is preferable that the substrate has a transmittance of light of 50% or higher in the visible region of 400 to 700 nm in the wavelength and further, that a flat and smooth substrate is used.

Preferred examples of the substrate which transmits light include glass plates and polymer plates. Specific examples of the glass plate include the plate formed using soda ash glass, glass containing barium and strontium, lead glass, aluminosilicate glass, borosilicate glass, barium borosilicate glass and quartz. Specific examples of the synthetic resin plate include plate made of polycarbonate resins, acrylic resins, polyethylene telephthalate resins, polyether sulfide resins and polysulfone resins.

The anode has a role of injecting holes into a hole transporting layer or a light emitting layer, and it is effective that the anode has a work function of 4.5 eV or greater. Specific examples of the material for the anode used in the present invention include indium tin oxide (ITO), mixture (IZO) of indium oxide and zinc oxide, mixture (ITCO) of ITO and cerium oxide, mixture (IZCO) of IZOR and cerium oxide, mixture (ICO) of indium oxide and cerium oxide, mixture (AZO) of zinc oxide and aluminum oxide, tin oxide (NESA), gold, silver, platinum, and copper.

The anode can be prepared by forming a thin film of the electrode material described above in accordance with a process such as the vapor deposition process and the sputtering process.

When the light emitted from the light emitting layer is obtained through the anode, it is preferable that the anode has a transmittance of the emitted light greater than 10%. It is also preferable that the sheet resistivity of the anode is several hundreds $\Omega/\square$ or smaller. The thickness of the anode is, in general, selected usually in the range of from 10 nm to 1 µm and preferably in the range of from 10 to 200 nm.

In the organic EL device of the present invention, the light emitting layer has the following functions (1) to (3):
(1) The injecting function: the function of injecting holes from the anode or the hole injecting layer and injecting electrons from the cathode or the electron injecting layer when an electric field is applied;
(2) The transporting function: the function of transporting the injected charges (electrons and holes) by the force of the electric field; and
(3) The light emitting function: the function of providing the field for recombination of electrons and holes and promote the recombination to emit light.

As the process for forming the light emitting layer, a well-known process such as the vapor deposition process, the spin coating process and the LB process can be employed. It is particularly preferable for the light emitting layer to be a molecular deposit film. The molecular deposit film is a thin film formed by the deposition of a material compound in the gas phase or a thin film formed by the solidification of a material compound in a solution or liquid phase. In general, the molecular deposit film can be distinguished from the thin film formed in accordance with the LB process (the molecular accumulation film) based on the differences in the aggregation structure and higher order structures and functional differences caused by these structural differences.

In addition, as disclosed in JP 57-51781A, the light emitting layer can also be formed by dissolving a binder such as a resin and the material compounds into a solvent to prepare a solution, followed by forming a thin film from the prepared solution in accordance with the spin coating process or the like.

In the present invention, any well-known metal complex compound other than the light emitting material consisting of pyrene derivative and the amine compound may be contained in the light emitting layer, or a light emitting layer containing any other well-known light emitting material may be laminated with the light emitting layer, as long as the object of the present invention is not adversely affected.

The metal complex is preferably a metal complex containing at least one metal selected from the group consisting of Ir, Ru, Pd, Pt, Os, and Re. The ligand of the metal complex preferably includes at least one skeleton selected from the group consisting of phenylpyridine skeleton, bipyridyl skeleton, and phenanthroline skeleton. Specific examples of the metal complex include tris(2-phenylpyridin)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethyl platinum porphyrin, octaphenyl platinum porphyrin, octaethyl palladium porphyrin, and octaphenyl palladium porphyrin. However, the metal complex is not limited thereto, and the appropriate complex is preferably selected in terms of a desired luminescent color, a device performance, and a relationship with a host compound.

The phosphorescent dopant is a compound capable of emitting light from the triplet exciton. The phosphorescent dopant is not restricted as long as it emits light from the triplet exciton, and preferably is a metal complex containing at least one metal selected from the group consisting of Ir, Ru, Pd, Pt, Os and Re, more preferably is a porphyrin metal complex or an ortho-metallated metal complex. As the porphyrin metal complex, a porphyrin platinum complex is preferable. The phosphorescent compound may be used singly or in combination of two or more.

There are various ligands to form the ortho-metallated metal complex, and preferred are 2-phenylpyridine derivatives, 7,8-benzoquinoline derivatives, 2-(2-thienyl)pyridine derivatives, 2-(1-naphthyl)pyridine derivatives, and 2-phenylquinoline derivatives. The derivatives may be substituted as occasion demands. In particular, a dopant introduced with a fluorine atom or a trifluoromethyl group is preferable for the blue light emission. In addition, a ligand other than the above ligands such as acetylacetonate and picric acid may be introduced as a co-ligand.

The amount of the phosphorescent dopant in the light emitting layer may be appropriately selected without particular limitation, and for example, it may be from 0.1 to 70% by mass, preferably from 1 to 30% by mass. The emission is faint and the advantage is not demonstrated when the amount is less than 0.1% by mass. The concentration quenching becomes noticeable so that the device performance is deteriorated when the amount exceeds 70% by mass.

Further, the light emitting layer may contain a hole transporting material, a electron transporting material or a polymer binder, if necessary.

The thickness of the light emitting layer is, in general, selected in the range of from 5 to 50 nm, preferably in the range of from 7 to 50 nm and the most preferably in the range of from 10 to 50 nm. It is resulted in difficult to form the light emitting layer and to control chromaticity thereof when the thickness is thinner than 5 nm, and it may be resulted in possibility of elevating driving voltage when it exceeds 50 nm.

The fluorescent dopant is preferably a compound selected from, for example, an amine-based compound, an aromatic compound, a chelate complex such as a tris(8-quinolinolato) aluminum complex, a coumarin derivative, a tetraphenylbutadiene derivative, a bisstyrylarylene derivative, and an oxadiazole derivative in accordance with a requested luminescent color. In particular, examples include an arylamine compound and an aryl diamine compound, and above all, a styryl amine compound, a styryl diamine compound, an aromatic amine compound, and an aromatic diamine compound are further preferable. Moreover, fused polycyclic aromatic compounds (except amine compound) are furthermore preferable. Those fluorescent dopants may be employable singly or in combination of two or more.

Preferred styrylamine compounds and styryldiamine compounds are represented by the following general formula (A):

(A)

where: $Ar^3$ represents a group selected from among a phenyl group, biphenyl group, a terphenylyl group, a stilbene group and a distyrylaryl group; $Ar^4$ and $Ar^5$ each independently represents an aromatic group having 6 to 20 carbon atoms; each of $Ar^3$, $Ar^4$ and $Ar^5$ may be substituted; p represents an integer of 1 to 4, and preferably an integer of 1 or 2; anyone of $Ar^3$ to $Ar^5$ is a group containing a styryl group. It is further preferable that at least one of $Ar^4$ and $Ar^5$ is substituted by the styryl group.

Examples of the aromatic hydrocarbon group having 6 to 20 carbon atoms include a phenyl group, a naphthyl group, an anthranyl group, a phenanthryl group, a terphenyl group, etc.

Preferred aromatic amine compounds and aromatic diamine compounds are represented by the following general formula (B):

(B)

where: $Ar^6$ to $Ar^8$ each independently represents a substituted or unsubstituted aryl group having 5 to 40 ring carbon atoms; q represents an integer of 1 to 4, and preferably an integer of 1 or 2.

Examples of the aryl group having 5 to 40 ring carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzthiophenyl group, an oxadiazolyl group, a diphenylanthranyl group, an indolyl group, a carbazolyl group, a pyridyl group, a benzquinolyl group, a fluoranthenyl group, an acenaphthofluoranthenyl group, a stilbene group, a perilenyl group, a crycenyl group, a picenyl group, a triphenylenyl group, a rubicenyl group, a benzanthracenyl group, a phenylanthranyl group, a bisanthracenyl group, or an aryl group represented by the following general formula (C) or (D); and preferably, a naphthyl group, an anthranyl group, a crycenyl group, a pyrenyl group, or an aryl group represented by the general formula (D).

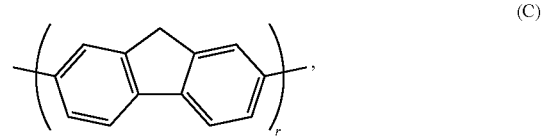

(C)

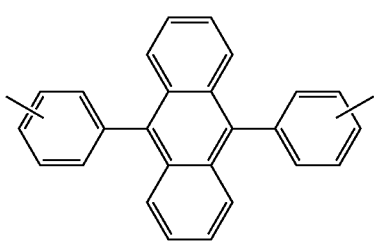

(D)

where: r represents an integer of 1 to 3.

Additionally, preferable examples of the substituent for the above aryl group include an alkyl group having 1 to 6 carbon atoms (an ethyl group, a methyl group, an i-propyl group, an n-propyl group, a s-butyl group, a t-butyl group, a pentyl group, a hexyl group, a cyclopentyl group, a cyclohexyl group, etc.); an alkoxy group having 1 to 6 carbon atoms (an ethoxy group, a methoxy group, an i-propoxy group, a n-propoxy group, an s-butoxy group, a t-butoxy group, a pentoxy group, a hexyloxy group, a cyclopentoxy group, a cyclohexyl oxy group, etc.); an aryl group having 5 to 40 ring carbon atoms; an amino group substituted with an aryl group having 5 to 40 ring carbon atoms; an ester group which has an aryl group having 5 to 40 ring carbon atoms; an ester group which has an alkyl group having 1 to 6 carbon atoms; a cyano group; a nitro group; and a halogen atom, etc.

The hole injecting and transporting layer is a layer which helps the injection of holes into the light emitting layer and transports the holes to the light emitting region. The layer exhibits a great mobility of holes and, in general, has an ionization energy as small as 5.5 eV or smaller. For the hole injecting and transporting layer, a material which transports holes to the light emitting layer at a small strength of the electric field is preferable. A material which exhibits, for example, a mobility of holes of at least $10^{-4}$ cm$^2$/V·sec under an electric field of from $10^4$ to $10^6$ V/cm is preferable.

With regard to the material which may be employed for forming the hole injecting and transporting layer, any material having the above preferable properties is employed without particularly restricted, which is selected from compounds commonly used as a hole transporting material of photoconductive materials and compounds used for forming the hole injecting layer of EL devices. Regarding with the aromatic amine derivative, compounds expressed with the following general formulae are employable.

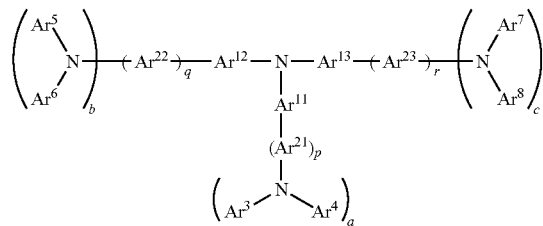

where: $Ar^{11}$ to $Ar^{13}$, $Ar^{21}$ to $Ar^{23}$ and $Ar^3$ to $Ar^8$ each independently represents a substituted or unsubstituted aromatic hydrocarbon group having 6 to 50 ring carbon atoms, or an aromatic heterocyclic ring group having 5 to 50 ring atoms; a to c and p to r each independently represents an integer of 0 to 3; a couple of $Ar^3$ and $Ar^4$, a couple of $Ar^5$ and $Ar^6$, and a couple of $Ar^7$ and $Ar^8$ may bond each other to form a saturated or unsaturated ring structure.

Specific examples of the substituted or unsubstituted aromatic hydrocarbon group having 6 to 50 ring carbon atoms and the substituted or unsubstituted aromatic heterocyclic ring group having 5 to 50 ring atoms include the same as those exemplified above about R' and R".

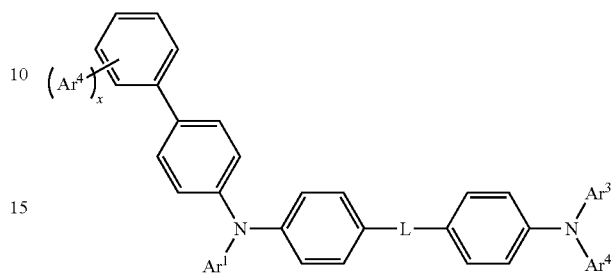

where: $Ar^1$ to $Ar^4$ each independently represents a substituted or unsubstituted aromatic ring group having 6 to 50 ring carbon atoms, or an aromatic heterocyclic ring group having 5 to 50 ring atoms; L represents a bonding group, which is a single bond, a substituted or unsubstituted aromatic hydrocarbon group having 6 to 50 ring carbon atoms, or an aromatic heterocyclic ring group having 5 to 50 ring atoms; x represents an integer of 0 to 5; and also, $Ar^2$ and $Ar^3$ may be bonded with each other to form a saturated or unsaturated ring. Specific examples of the aromatic hydrocarbon group having 6 to 50 ring carbon atoms and the aromatic heterocyclic group having 5 to 50 ring atoms are the same as those described above.

Specific examples include triazole derivatives (refer to U.S. Pat. No. 3,112,197, etc.), oxadiazole derivatives (refer to U.S. Pat. No. 3,189,447, etc.), imidazole derivatives (refer to JP-B 37-16096, etc.), polyarylalkane derivatives (refer to U.S. Pat. Nos. 3,615,402; 3,820,989 and 3,542,544, JP-B 45-555, JP-B 51-10983, JP 51-93224A, JP 55-17105A, JP 56-4148A, JP 55-108667A, JP 55-156953A, JP 56-36656A, etc.), pyrazoline derivatives and pyrazolone derivatives (refer to U.S. Pat. Nos. 3,180,729 and 4,278,746; JP 55-88064A, JP 55-88065A, JP 49-105537A, JP 55-51086A, JP 56-80051A, JP 56-88141A, JP 57-45545A, JP 54-112637A, JP 55-74546A, etc.), phenylenediamine derivatives (refer to U.S. Pat. No. 3,615,404; JP-B 51-10105, JP-B 46-3712, JP-B 47-25336, JP 54-119925A, etc.), arylamine derivatives (refer to U.S. Pat. Nos. 3,567,450; 3,240,597; 3,658,520; 4,232,103; 4,175,961 and 4,012,376; JP-B 49-35702, JP-B 39-27577, JP 55-144250A, JP 56-119132A, JP 56-22437A, German Patent No. 1,110,518, etc.), amino-substituted chalcone derivatives (refer to U.S. Pat. No. 3,526,501, etc.), oxazole derivatives (disclosed in U.S. Pat. No. 3,257,203, etc.), styrylanthracene derivatives (refer to JP 56-46234A, etc.), fluorenone derivatives (refer to JP 54-110837A, etc.), hydrazone derivatives (refer to U.S. Pat. No. 3,717,462, JP 54-59143A, JP 55-52063A, JP 55-52064A, JP 55-46760A, JP 57-11350A, JP 57-148749A, JP 2-311591A, etc.), stilbene derivatives (refer to JP 61-210363A, JP 61-228451A, JP 61-14642A, JP 61-72255A, JP 62-47646A, JP 62-36674A, JP 62-10652A, JP 62-30255A, JP 60-93455A, JP 60-94462A, JP 60-174749A, JP 60-175052A, etc.), silazane derivatives (U.S. Pat. No. 4,950,950), polysilane-based polymer (JP 2-204996A), aniline-based copolymer (JP 2-282263A), an electrically conductive high-molecular oligomer (particularly, thiophene oligomer), etc.

With regard to the material for the hole injecting layer, the above materials are also employable, and porphyrin compounds (disclosed in JP 63-295695A), aromatic tertiary amine compounds and styryl amine compounds (refer to U.S. Pat. No. 4,127,412, JP 53-27033A, JP 54-58445A, JP 55-79450A, JP 55-144250A, JP 56-119132A, JP 61-295558A, JP 61-98353A, JP 63-295695A, etc.) are preferable and the aromatic tertiary amine compounds are particularly preferable.

Further, examples include, 4,4'-bis(N-(1-naphthyl)-N-phenylamino)biphenyl (NPD) which has 2 fused aromatic rings in its molecule described in U.S. Pat. No. 5,061,569 and 4,4',4''-tris(N-(3-methylphenyl)-N-phenylamino)triphenylamine (MTDATA) described in JP 4-308688A which includes three triphenylamine units connected in a star burst configuration.

Besides, a nitrogen-containing compound with heterocyclic ring derivative represented by the following general formula disclosed in Japanese Registered Patent No. 3571977 is also employable.

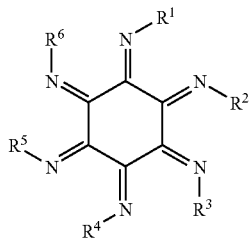

where: $R^1$, $R^2$, $R^3$, $R^4$, $R^5$ and $R^6$ each independently represents any one of a substituted or unsubstituted alkyl group, a substituted or unsubstituted aryl group, a substituted or unsubstituted aralkyl group or a substituted or unsubstituted heterocyclic ring group. However, $R^1$, $R^2$, $R^3$, $R^4$, $R^5$ and $R^6$ may be identical to or different from each other. Further, a couple of $R^1$ and $R^2$, a couple of $R^3$ and $R^4$, a couple of $R^5$ and $R^6$; or a couple of $R^1$ and $R^6$, a couple of $R^2$ and $R^3$, and a couple of $R^4$ and $R^5$ may be bonded with each other to form a fused ring structure.

Still further, a compound represented by the following formula disclosed in U.S. Patent Application Publication No. 2004/0113547 is also employable.

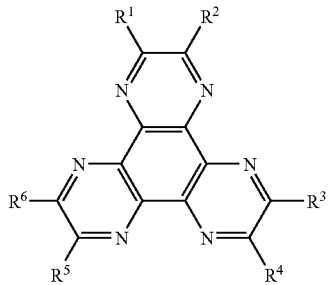

where: $R^1$ to $R^6$ are substituents, and preferably, they each independently represents an electron withdrawing group such as a cyano group, a nitro group, a sulfonyl group, a carbonyl group, a trifluoromethyl group, a halogen atom, etc.

Moreover, an inorganic compound such as a p-type Si and a p-type SiC may be also used as the material for the hole injecting layer.

To form the hole injecting and transporting layer, a thin film may be formed from the above compound in accordance with a well-known process such as the vacuum vapor deposition process, the spin coating process, the casting process and the LB process. Although the thickness of the hole injecting and transporting layer is not particularly limited, the thickness is usually in the range of from 5 nm to 5 μm. The hole injecting and transporting layer may be a single layer made of one or more kinds of materials mentioned above or may be laminated with another hole injecting and transporting layer made of a different material, as long as the hole injecting and transporting layer contains the compound of the present invention in its hole transporting region.

An organic semiconductor layer which preferably has an electric conductance of $10^{10}$ S/cm or greater may be favorably provided to assist the injection of holes or electrons into the light emitting layer. Examples of the materials for the organic semiconductor layer include electrically conductive oligomers such as an oligomer having thiophene and an oligomer having arylamine disclosed in JP 8-193191A; and electrically conductive dendrimers such as a dendrimer having an arylamine dendrimer.

The electron injecting and transporting layer is a layer having a great electron mobility, which assists the injection of electrons into the light emitting layer and transports them to a light emitting region. Among the electron injecting layers, the adhesion improving layer is a layer made of a material exhibiting excellent adhesion to the cathode.

Further, it is known that because the emitted light reflects on the electrode (cathode in this case) in the organic EL device, the light taken out directly through the anode and the light taken out after the reflection on the electrode interfere each other. To utilize the interference effect effectively, the thickness of the electron transporting layer is appropriately selected from several nm to several μm. When the film is thicker, the hole mobility is preferably at least $10^{-5}$ cm$^2$/Vs under an electric field of from $10^4$ to $10^6$ V/cm for avoiding the elevation of driving voltage.

As the material for the electron injecting layer, metal complexes of 8-hydroxyquinoline or derivatives thereof and oxadiazole derivatives are preferable. As the material for the electron injecting layer, metal complexes of 8-hydroxyquinoline or derivatives thereof and oxadiazole derivatives are preferable. Examples of the metal complexes of 8-hydroxyquinoline and derivatives thereof include metal chelate oxinoid compounds including chelates of oxine (in general, 8-quinolinol or 8-hydroxyquinoline), for example, tris(8-quinolinolato)aluminum.

On the other hand, examples of the oxadiazole derivatives include an electron transfer compound represented by the following general formulae:

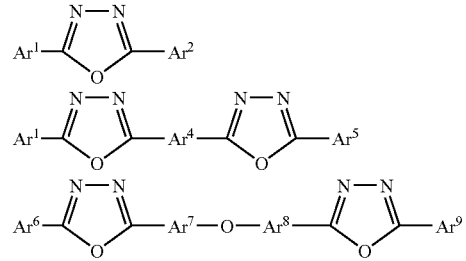

where: $Ar^1$, $Ar^2$, $Ar^3$, $Ar^5$, $Ar^6$ and $Ar^9$ may be identical to or different from each other and each independently represents a substituted or unsubstituted aryl group; further, $Ar^4$, $Ar^7$, $Ar^8$ each independently represents a substituted or unsubstituted arylene group, each of which may be identical to or different from each other respectively.

Examples of the aryl group include a phenyl group, a biphenyl group, an anthranyl group, a perilenyl group and a pyrenyl group. Further, examples of the arylene group include a phenylene group, a naphthylene group, a biphenylene group, an anthranylene group, a perilenylene group, a pyrenylene group, etc. Examples of the substituent include an alkyl group having 1 to 10 carbon atoms, an alkoxy group having 1 to 10 carbon atoms and a cyano group. The electron transfer compound is preferably a thin-film forming compound.

Specific examples of the electron transfer compounds are shown below:

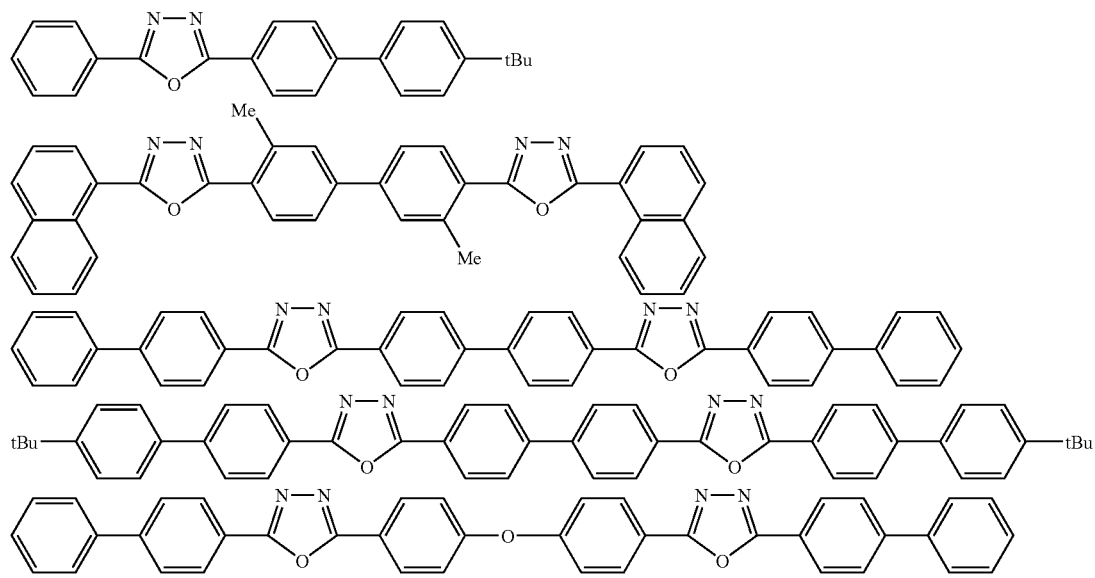

The compounds represented by the following general formulae (E) to (J) may be also used as the material for the electron injecting layer and the electron transporting layer.

A nitrogen-containing heterocyclic derivative represented by the following general formula (E) or (F):

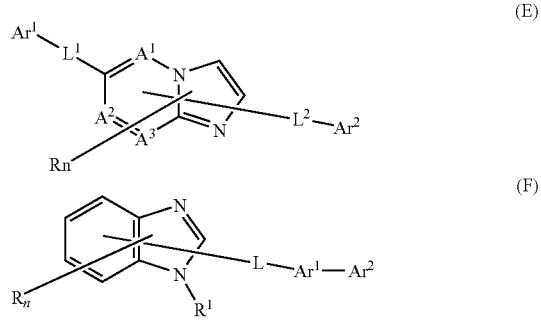

where: $A^1$ to $A^3$ each independently represents a nitrogen atom or a carbon atom; $Ar^1$ represents a substituted or unsubstituted aryl group having 6 to 60 ring carbon atoms or a substituted or unsubstituted heteroaryl group having 3 to 60 ring carbon atoms; $Ar^2$ represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms or those divalent groups; at least one of $Ar^1$ and $Ar^2$ represents a substituted or unsubstituted fused ring group having 10 to 60 ring carbon atoms, a substituted or unsubstituted monohetero fused ring group having 3 to 60 ring carbon atoms; $L^1$, $L^2$ and L each independently represents a single bond, a substituted or unsubstituted arylene group having 6 to 60 ring carbon atoms, a substituted or unsubstituted heteroarylene group having 3 to 60 ring carbon atoms or a substituted or unsubstituted fluorenylene group; R represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms; n represents an integer of 0 to 5; when n is 2 or greater, Rs may be identical to or different from each other and adjacent couple of Rs may be bonded with each other to form a carbocyclic aliphatic ring or a carbocyclic aromatic ring.

A nitrogen-containing heterocyclic derivative represented by the following general formula (G):

where: HAr represents a nitrogen-containing heterocyclic group having 3 to 40 carbon atoms which may be substituted; L represents a single bond, an arylene group having 6 to 60 carbon atoms which may be substituted, a heteroarylene group having 3 to 60 carbon atoms which may be substituted or a fluorenylene group which may be substituted; $Ar^1$ represents a divalent aromatic hydrocarbon group having 6 to 60 carbon atoms which may be substituted; and $Ar^2$ represents an aryl group having 6 to 60 carbon atoms which may be substituted or a heteroaryl group having 3 to 60 carbon atoms which may be substituted.

A silacyclopentadiene derivative represented by the following general formula (H):

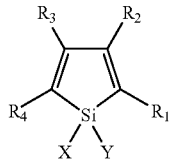
(H)

where: X and Y each independently represents a saturated or unsaturated hydrocarbon group having 1 to 6 carbon atoms, an alkoxy group, an alkenyloxy group, an alkynyloxy group, a hydroxy group, a substituted or unsubstituted aryl group, or a substituted or unsubstituted hetero ring, or a structure in which X and Y are bonded with each other to form a saturated or unsaturated ring; $R^1$ to $R^4$ each independently represents a hydrogen atom, a halogen atom, a substituted or unsubstituted alkyl group having 1 to 6 carbon atoms, an alkoxy group, an aryloxy group, a perfluoroalkyl group, a perfluoro alkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a hetero ring group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or a structure in which substituted or unsubstituted fused rings are formed when they become adjacent.

A borane derivative represented by the following general formula (I):

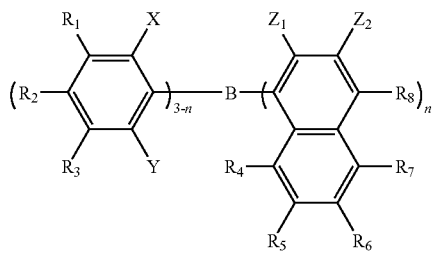
(I)

where: $R_1$ to $R_8$ and $Z_2$ each independently represents a hydrogen atom, a saturated or unsaturated hydrocarbon group, an aromatic hydrocarbon group, a hetero ring group, a substituted amino group, a substituted boryl group, an alkoxy group or an aryloxy group; X, Y and $Z_1$ each independently represents a saturated or unsaturated hydrocarbon group, an aromatic group, a hetero ring group, substituted amino group, an alkoxy group or an aryloxy group; substituents of $Z_1$ and $Z_2$ may be bonded with each other to form a fused ring; n represents an integer of 1 to 3; and when n is 2 or greater, $Z_1$'s may be different from each other, with the proviso that a case where n is 1, X, Y and $R_2$ are methyl groups and $R_8$ is a hydrogen atom or a substituted boryl group and a case where n is 3 and $Z_1$ is a methyl group are excluded.

(J)

where: $Q^1$ and $Q^2$ each independently represents a ligand represented by the following general formula (K), L represents a halogen atom, a substituted or unsubstituted alkyl group, a substituted or unsubstituted cycloalkyl group, a substituted or unsubstituted aryl group, a substituted or unsubstituted heterocyclic group, —$OR^1$ (wherein $R^1$ represents a hydrogen atom, a substituted or unsubstituted alkyl group, a substituted or unsubstituted cycloalkyl group, a substituted or unsubstituted aryl group, a substituted or unsubstituted heterocyclic group), or a ligand represented by —O—Ga-$Q^3$($Q^4$) (wherein $Q^3$ and $Q^4$ are the same as $Q^1$ and $Q^2$).

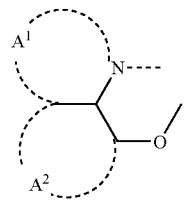
(K)

where: $A^1$ and $A^2$ each represents a fused six-membered aryl ring structure which may be substituted.

The metal complex strongly characterizes n-type semiconductor and has a large capability of the electron injection. Since the generation energy for forming the metal complex is small, the bonding between the metal and the ligand is strong, to increase the fluorescence quantum efficiency of light emitting materials Specific examples of the substituents of rings $A^1$ and $A^2$ each forming the ligand in the general formula (K) include a halogen atom such as a chlorine atom, a bromine atom, an iodine atom and a fluorine atom; substituted or unsubstituted alkyl group such as a methyl group, an ethyl group, a propyl group, a butyl group, an s-butyl group, a t-butyl group, a pentyl group, a hexyl group, a heptyl group, an octyl group, a stearyl group, a trichloromethyl group, etc.; substituted or unsubstituted aryl group such as a phenyl group, a naphthyl group, 3-methylphenyl group, 3-methoxyphenyl group, 3-fluorophenyl group, 3-trichloromethylphenyl group, 3-trifluoromethylphenyl group, 3-nitrophenyl group, etc.; substituted or unsubstituted alkoxy group such as a methoxy group, an n-butoxy group, a t-butoxy group, a trichloromethoxy group, a trifluoroethoxy group, a pentafluoropropoxy group, 2,2,3,3-tetrafluoropropoxy group, 1,1,1,3,3,3-hexafluoro-2-propoxy group, 6-(perfluoroethyl)hexyloxy group, etc.; a substituted or unsubstituted aryloxy group such as a phenoxy group, a p-nitrophenoxy group, a p-t-butylphenoxy group, 3-fluorophenoxy group, a pentafluorophenyl group, 3-trifluoromethylphenoxy group, etc.; a substituted or unsubstituted alkylthio group such as a methylthio group, an ethylthio group, a t-butylthio group, a hexylthio group, an octylthio group, a trifluoromethylthio group, etc.; a substituted or unsubstituted arylthio group such as a phenylthio group, a p-nitrophenylthio group, a p-t-butylphenylthio group, 3-fluorophenylthio group, a pentafluorophenylthio group, 3-trifluoromethylphenylthio group, etc.; mono- or di-substituted amino groups such as a cyano group, a nitro group, an amino group, a methylamino group, a diethylamino group, an ethylamino group, a diethylamino group, a dipropylamino group, a dibutyl amino group, a diphenylamino group, etc.; an acylamino groups such as bis(acetoxymethyl)amino group, bis(acetoxyethyl)amino group, bis(acetoxypropyl)amino group, bis(acetoxybutyl)amino group, etc.; a carbamoyl group such as a hydroxy group, a siloxy group, an acyl group, a methylcarbamoyl group, a dimethylcarbamoyl group, an ethylcarbamoyl group, a diethylcarbamoyl group, a propylcarbamoyl group, a butyl carbamoyl group, a phenylcarbamoyl group, etc.; a cycloalkyl group such as a carboxylic acid group, a sulfonic acid group, an imido group, a cyclopentane group, a cyclohexyl group, etc.; aryl group such as a phenyl group, a naphthyl group, a biphenyl group, an anthranyl group, a phenanthryl group, a fluorenyl group, a pyrenyl group, etc.; a heterocyclic group such as a pyridinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a triazinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzimidazolyl group, a pranyl group, etc. The above substituents may be bonded with each other to form a six-membered aryl ring or hetero ring.

A preferred embodiment of the organic EL device of the present invention contains a reductive dopant in an electron transporting region or an interfacial region between a cathode and an organic compound layer. The reductive dopant is defined as the substance capable of reducing an electron transporting compound. Accordingly, various compounds having a reducing property may be used, and examples of the reductive dopant include at least one compound selected from alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals, and organic complexes of rare earth metals.

More specifically, at least one alkali metal selected from the group consisting of Na (the work function: 2.36 eV), K (the work function: 2.28 eV), Rb (the work function: 2.16 eV) and Cs (the work function: 1.95 eV) and at least one alkaline earth metal selected from the group consisting of Ca (the work function: 2.9 eV), Sr (the work function: 2.0 to 2.5 eV) and Ba (the work function: 2.52 eV), are preferable. Substances having a work function of 2.9 eV or smaller are preferable. Among the above substances, at least one alkali metal selected from the group consisting of K, Rb and Cs is more preferable, Rb and Cs are still more preferable, and Cs is most preferable as the reducing dopant. Since those alkali metals have a particularly high reducing capability, the luminance is improved and the lifetime is prolonged by the addition thereof into an electron injection region in a relatively small amount. A combination of two or more alkali metals is also preferably used as the reductive dopant having a work function of 2.9 eV or smaller. A combination containing Cs such as Cs and Na, Cs and K, Cs and Rb and Cs, Na and K is particularly preferred. By containing Cs in combination, the reducing capability is effectively performed, and the luminance is enhanced and the lifetime is prolonged in the organic EL device by the addition into the electron injection region.

In the present invention, an electron injecting layer made of an electrically insulating material or a semiconductor may be further disposed between the cathode and the organic layer. The electron injecting layer enables to effectively prevent a leak of electric current and to improve the electron injection property. As the electrically insulating material, at least one metal compound selected from the group consisting of chalcogenides of alkali metals, chalcogenides of alkaline earth metals, halides of alkali metals and halides of alkaline earth metals is preferable. When the electron injecting layer is made of these alkali metal chalcogenide or so, the electron injection property is further improved. Preferable examples of the chalcogenide of an alkali metal include $Li_2O$, $K_2O$, $Na_2S$, $Na_2Se$ and $Na_2O$. Preferable examples of the chalcogenide of an alkaline earth metal include CaO, BaO, SrO, BeO, BaS and CaSe. Moreover, examples of the halide of desirable alkali metal include such as LiF, NaF, KF, CsF, LiCl, KCl, NaCl, etc. Furthermore, preferable examples of the halide of an alkaline earth metal include fluoride such as $CaF_2$, $BaF_2$, $SrF_2$, $MgF_2$ and $BeF_2$ and halides other than the fluorides. Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron transporting layer forms a crystallite or amorphous insulating thin film. When the electron transporting layer is constituted with the above insulating thin film, a more uniform thin film can be formed and defective pixels such as dark spots can be decreased. Examples of the inorganic compound include chalcogenides of alkali metals, chalcogenides of alkaline earth metals, halides of alkali metals and halides of alkaline earth metals which are described above.

For the cathode, a material such as a metal, an alloy, an electrically conductive compound, or a mixture of those materials which has a small work function (4 eV or smaller) is used as an electrode material. Examples of the electrode substance include sodium, sodium-potassium alloy, magnesium, lithium, cesium, magnesium-silver alloy, aluminum/aluminum oxide, $Al/Li_2O$, Al/LiO, Al/LiF, aluminum-lithium alloy, indium, rare earth metal, etc.

The cathode is prepared by forming a thin film of the electrode material described above in accordance with a process such as the vapor deposition process and the sputtering process.

When the light emitted from the light emitting layer is taken out of the cathode, it is preferable that the cathode has a transmittance of greater than 10% to the emitted light. It is also preferable that the sheet resistivity of the cathode is several hundreds $\Omega/\square$ or smaller and the thickness of the cathode is, in general, from 10 nm to 1 μm and preferably from 50 to 200 nm.

In general, an organic EL device tends to form defects in pixels due to leak and short circuit since an electric field is applied to ultra-thin films. To prevent the defects, an electrically insulating thin film layer may be inserted between the pair of electrodes.

Examples of the material for the electrically insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be employed.

In order to prepare the organic EL device of the present invention, the anode, the light emitting layer, the hole injecting layer and the electron injecting layer are formed in accordance with the foregoing process using the foregoing materials, and the cathode is formed in the last step. Alternatively, each layer may be formed in a reverse order from the cathode to the anode.

Hereinafter, an embodiment of the process for preparing an organic EL device having a construction in which an anode, a hole injecting layer, a light emitting layer, an electron injecting layer, and a cathode are disposed successively on a substrate which transmits light will be described.

First, on a suitable substrate which transmits light, a thin film of an anode substance is formed into the anode so as to have a film thickness of 1 μm or thinner, preferably from 10 nm to 200 nm in accordance with a vapor deposition process, a sputtering process, etc. Then, a hole injecting layer is formed on the anode. The hole injecting layer can be formed in accordance with the vacuum vapor deposition process, the spin coating process, the casting process or the LB process, as described above. The vacuum vapor deposition process is preferable because a uniform film can be easily obtained and pinhole is little formed. When the hole injecting layer is formed in accordance with the vacuum vapor deposition process, the conditions are preferably selected from the following ranges: temperature of deposition source: 50 to 450° C.; degree of vacuum: $10^{-7}$ to $10^{-3}$ Torr; vapor deposition rate: 0.01 to 50 nm/s; temperature of substrate: −50 to 300° C.; and film thickness: 5 nm to 5 μm; although depending on the employed compound (material for hole injecting layer), the crystal structure and the recombination structure.

Then, a light emitting layer is formed on the hole injecting layer. The light emitting layer is formed by depositing a thin film of the organic light emitting material in accordance with the vacuum vapor deposition process, the sputtering process, the spin coating process or the casting process. The vacuum vapor deposition process is preferable because a uniform film can be easily obtained and pinhole is little formed. When the light emitting layer is formed in accordance with the vacuum vapor deposition process, the conditions of the vacuum vapor deposition can be selected in the same ranges as in the deposition of the hole injecting layer, although depending on the compound to be used. With regard to the film thickness, it is preferable to be within the range of from 10 to 40 nm.

Next, the electron injecting layer is formed on the light emitting layer. Similarly to the formation of the hole injecting layer and light emitting layer, the electron injecting layer is preferably formed in accordance with the vacuum vapor deposition process, because a uniform film is required. The conditions of the vacuum vapor deposition can be selected from the same ranges as in the formation of the hole injecting layer and the light emitting layer.

Finally, the cathode is formed on the electron injecting layer, to obtain an organic EL device. The cathode is made of a metal and can be formed in accordance with the vacuum vapor deposition process or the sputtering process. However, the vacuum vapor deposition process is preferably employed in order to prevent the underlying organic layers from being damaged during the formation of the film.

In the above fabrication of the organic EL device, the layers from the anode to the cathode are successively formed preferably in a single evacuation operation.

The process for forming the layers in the organic EL device of the present invention is not particularly limited. A conventional process such as the vacuum vapor deposition process and the spin coating process or so can be employed. The organic thin film layer containing the compound of the formula (1) included in the organic EL device of the present invention can be formed in accordance with the vacuum vapor deposition process, the molecular beam epitaxy process (the MBE process) or a known method of coating a solution of the compound such as the dipping process, the spin coating process, the casting process, the bar coating process and the roller coating process.

In the case of generally called as a coating process, i.e., in the case of a process for forming each layers in the organic EL device employing a solution containing the organic EL material, it is possible to prepare and use a homogeneous solution employing, depending on the purpose, a good solvent for the organic EL material with regard to the solvent. Also, it is possible to prepare and use a dispersed solution employing a poor solvent or a mixed solvent of the good solvent and the poor solvent.

The solution containing the organic EL material of the present invention contains the polycyclic ring assembly compound of the present invention or the polymer compound of the present invention.

Regarding with the solvent to be employed, there is no restriction as long as it is generally available, and it is appropriate to select in view of viscosity and solubility together with process compatibility.

Examples of a frequently probable good solvent include aromatic base solvent, halogen-based solvent, ether-based solvent, etc., and examples of a frequently probable poor solvent include alcohol-based solvent, ketone-based solvent, paraffin-based solvent or alkylbenzene derivatives having 4 or more carbon atoms, etc.

Specific examples are as follows. Specific examples of the frequently probable good solvent include toluene, xylene and mesitylene which are aromatic base solvent; chlorobenzene which is halogen-based solvent; diphenylether which is ether-based solvent, etc. Specific examples of the frequently probable poor solvent include straight chain or branched alcohol having 1 to 20 carbon atoms being the alcohol-based solvent such as methanol, ethanol, propanol, butanol, pentanol, hexanol, heptanol, octanol, nonanol, decanol, etc.; and as benzyl alcohol derivatives, hydroxyalkylbenzene derivatives and alkylbenzene derivatives, straight chain or branched butylbenzene, dodecylbenzene, tetralin, cyclohexylbenzene, etc.

Regarding with the use amount of the solvent, it can be appropriately adjusted considering about the amount, the kind, the thickness of the organic thin film layer, etc., concerning with the polycyclic ring assembly compound or the polymer compound.

The organic EL device of the present invention may be fabricated by forming at least one layer of the organic thin film layers using the foregoing solution for the organic EL material of the present invention.

Although the thickness of each layer in the organic thin film layer in the organic EL device of the present invention is not particularly limited, a thickness in the range of several nanometers to 1 μm is preferable usually in order to avoid defects such as pin holes, and to improve the efficiency.

The organic EL device emits light when a direct voltage of 5 to 40 V is applied with the anode being + terminal and the cathode being − terminal. In the reverse polarity, no electric current flows and no light is emitted upon the application of voltage. When an alternating voltage is applied, the uniform light emission is observed only in the polarity where the anode is + and the cathode is −. The wave shape of alternating voltage is not limited.

EXAMPLES

In the following, examples of the organic EL device in the present invention will be described, however, the examples should not be construed as limiting the invention. Additionally, evaluation for an organic EL device obtained with each example is as follows.

(1) Initial performance: A predetermined voltage was applied to the organic EL device, and a current value at the time of the application was measured. An emission luminance value and CIE 1931 chromaticity coordinates were measured by a luminance meter (Spectroradiometer CS-1000, manufactured by Konica Minolta Sensing, Inc.) simultaneously with the measurement of the current value, followed by evaluation.

(2) Lifetime: The organic EL device was driven at a constant current and a specified initial luminance. The device was evaluated for its lifetime on the basis of the half time period of the luminance and changes of chromaticity.

Synthesis Example 1

A host material H-1 was synthesized in accordance with the following scheme.

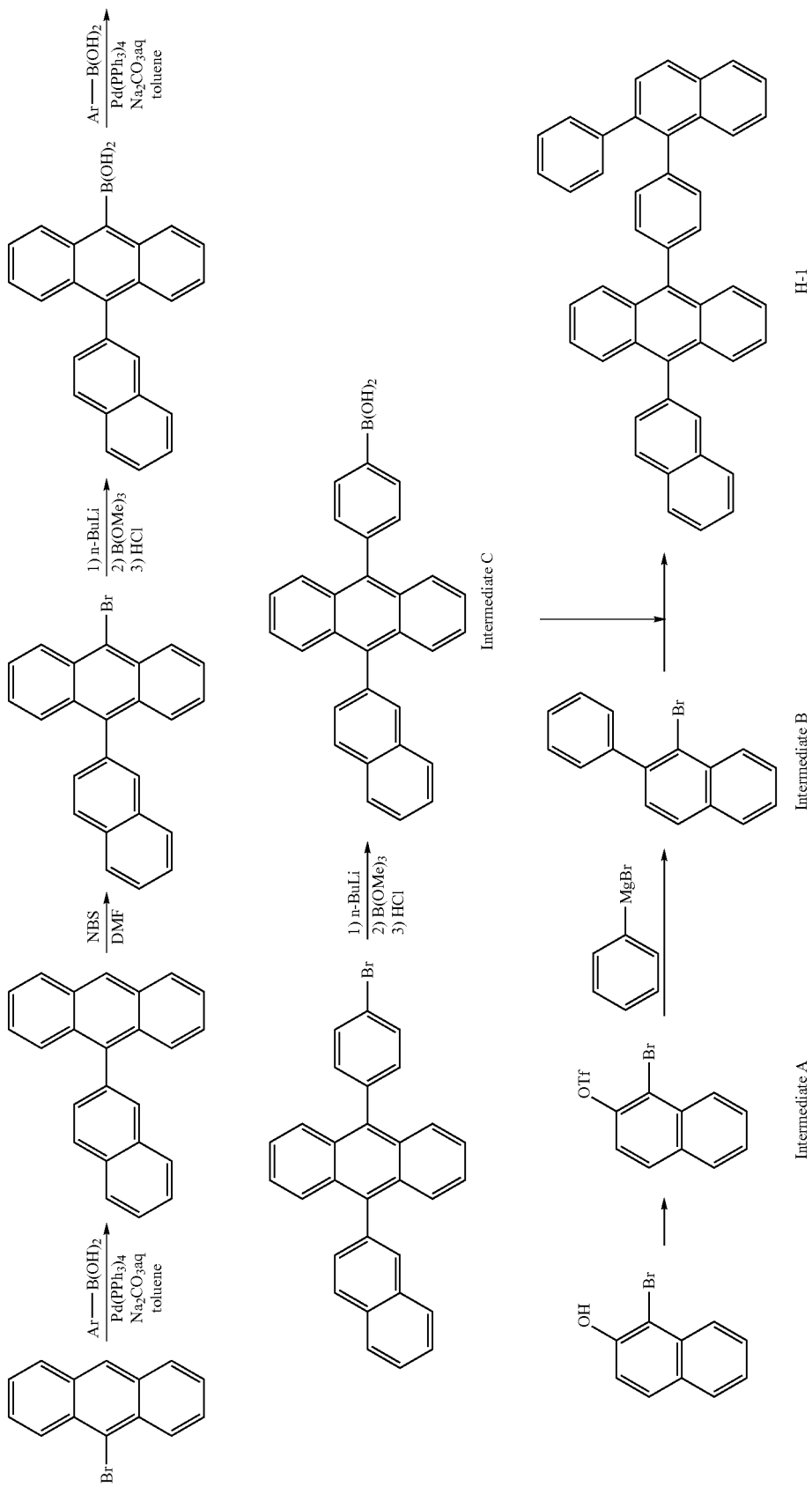

[Synthesis of Intermediate A]

Under an atmospheric argon gas, 2 L of methylene chloride was added into 260.5 g (1.17 mol) of 1-bromonaphthol and the resultant mixture solution was dissolved, followed by adding 129.1 g (1.28 mol) of diisopropylamine. Subsequently, cooling down to −5° C., 363.2 g (1.28 mol) of trifluoromethanesulfonic anhydride was dropped down, and after elevating the temperature up to the room temperature, the resultant mixture solution was stirred and allowed to react for 1 hour. Then, adding 0.8 L of 5% sodium hydrogen carbonate aqueous solution, discontinued to allow the resultant mixture solution to react, and extracted through methylene chloride/ion-exchange water, followed by washing an organic layer through 0.7 N hydrochloric acid aqueous solution and the ion-exchange water. Subsequently, drying the organic layer over magnesium sulfate, the solvent was distillated under reduced pressure to obtain 369 g (89% yield, 98% purity) of Intermediate A.

[Synthesis of Intermediate B]

Under an atmospheric argon gas, adding 0.5 L of ether onto 47.6 g (1.96 mol) of magnesium, and while conducting temperature control at about 35° C., a solution of bromobenzene 294.2 g (1.87 mol)/ether (0.6 L) was dropped down and the resultant mixture solution was stirred for 1 hour to prepare Grignard reagent.

Then, under an atmospheric argon gas, 345.7 g (0.97 mol) of Intermediate A, 87.7 g (1.01 mol) of lithium bromide, 8.8 g (14.9 mol) of $PdCl_2$ (dppp) (dppp: diphenylphosphino propane ligand) and 2.3 L of ether were added. Subsequently, cooling down to −10° C., the above-mentioned Grignard reagent was dropped, followed by stirring overnight. On the next day, 2.0 L of 0.2 N hydrochloric acid aqueous solution was dropped down while conducting temperature control at 0° C., and the reaction was discontinued. Then, the precipitate was separated by filtration, and the organic layer was washed through 0.2 N hydrochloric acid aqueous solutions and the ion-exchange water. Subsequently, after condensing the organic layer, it was subjected to silica gel processes with hexane, and by further re-crystallizing with hexane, white crystals were obtained. The resultant white crystal was dried to obtain 175.9 g (54.7% yield, 99% purity) of Intermediate B. Intermediate C was synthesized in accordance with a known approach as the above-mentioned scheme. Also, the host material H-1 was synthesized in accordance with a known approach (Suzuki Coupling Reaction).

Synthesis Examples 2 to 3

Host materials H-2 and H-3 were synthesized in accordance with the same scheme as Synthesis Example 1.

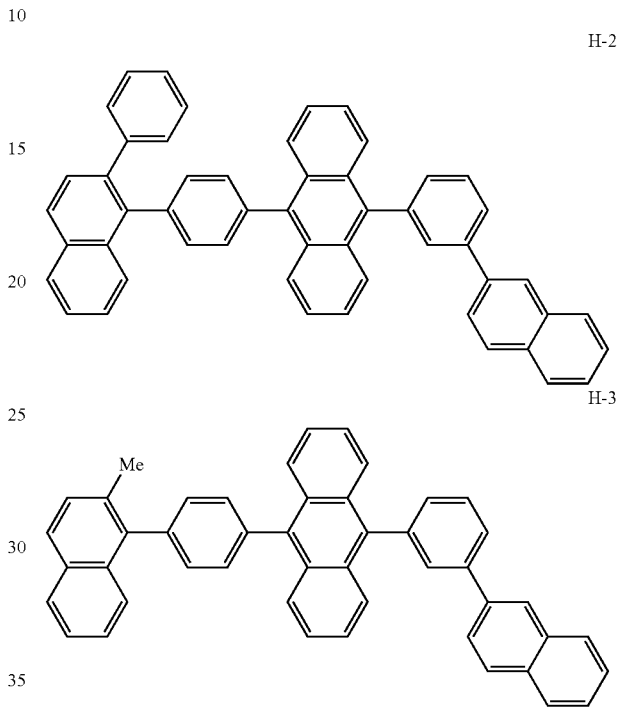

Synthesis Example 4

A host material H-4 was synthesized in accordance with the following scheme.

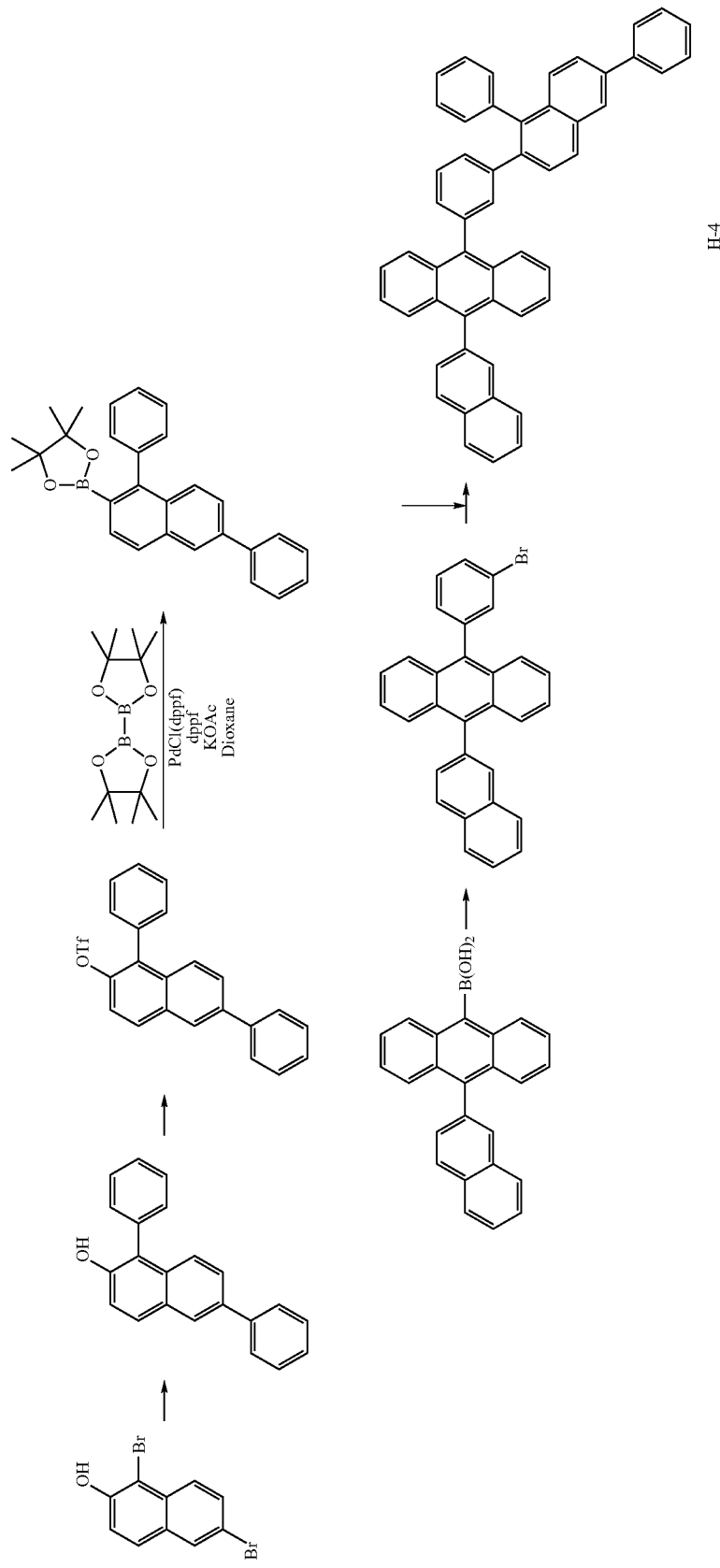

Synthesis Example 5

A host material H-5 was synthesized in accordance with the following scheme.

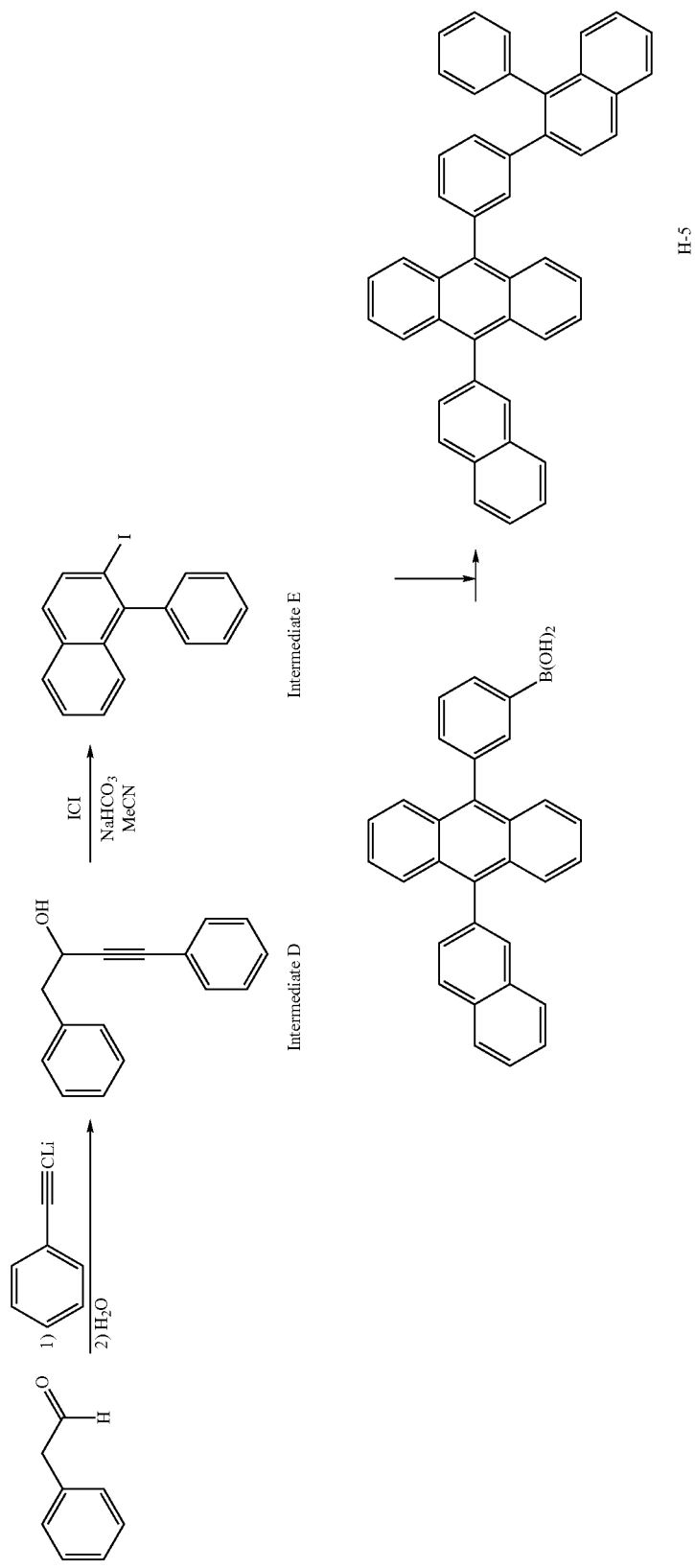

Additionally, Intermediate E was synthesized in accordance with the description in the literature J. Org. Chem., 71 (1), 237 (2006).

[Synthesis of Intermediate D]

Under an atmospheric argon gas, adding 4 L of dehydrated tetrahydrofuran (THF) to 465 g (4.55 mol) of ethyl benzene, the resultant mixture solution was cooled down to 0° C. or lower. Subsequently, dropping 2.9 L of 1.6 M n-butyllithium into the solution, it was stirred at 0° C. or lower for 4 hours. Then, after dropping 323 g (2.69 mol) of phenylacetaldehyde/2 L of dehydrated THF, the resultant mixture solution was stirred and allowed to react at the room temperature for 15 hours. Subsequently, adding 1 L of ion-exchange water and 2 L of ethyl acetate, an aimed substance was extracted, and by condensing the organic layer, 652 g of a crude product was obtained. Next, the crude product was purified through a column chromatography (silica gel: 5 kg, ethyl acetate/hexane=1/5) treatment, and the resultant solution was condensed and dried to obtain 447 g (74% yield, 91.1% purity) of Intermediate D.

[Synthesis of Intermediate E]

Under an atmospheric argon gas, 447 g (2.01 mol) of Intermediate E, 338 g (4.02 mol) of sodium hydrogen carbonate, and 6 L of acetonitrile were blended. Then, dropping 653 g (4.02 mol) of iodine monochloride (ICl)/1 L of acetonitrile, the resultant mixture solution was stirred for 30 minutes. Subsequently, adding 1 L of saturated sodium thiosulfate and 3 L of ethyl acetate, the resultant mixture solution was stirred and extracted. The organic layer was washed through water, and condensed to obtain 480 g of a crude product. Next, the crude product was purified through a column chromatography (silica gel: 5 kg, hexane-toluene/hexane=1/4) treatment, and after condensing the resultant solution, it was re-precipitated among methanol. The resultant solid was dried to obtain 396 g (59% yield, 99.4% purity) of Intermediate E. The host material H-5 was synthesized in accordance with a known approach (Suzuki Coupling Reaction).

Synthesis Examples 6 to 8

Host materials H-6, H-7 and H-8 were synthesized in accordance with the same scheme as Synthesis Example 5.

H-6

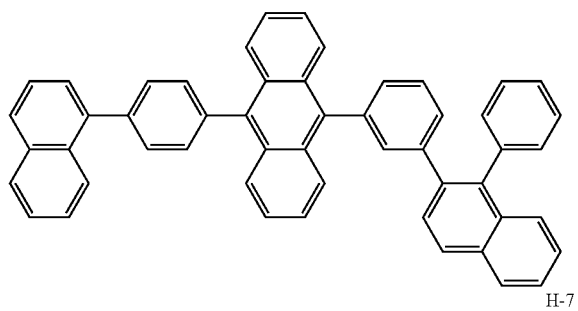

H-7

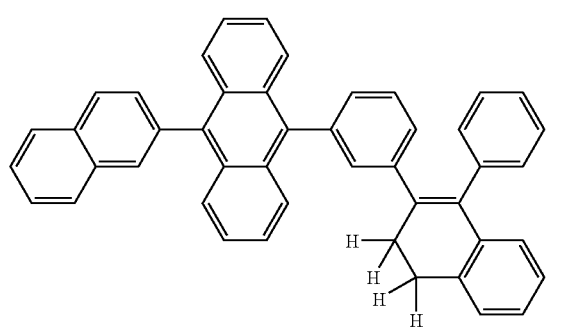

-continued

H-8

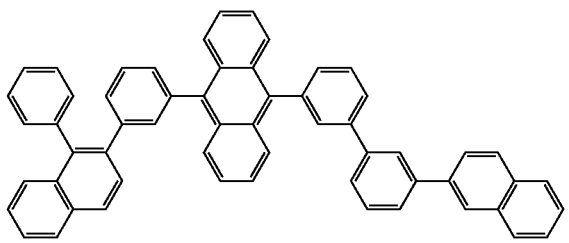

Synthesis Example 9

A host material H-9 was synthesized in accordance with the following scheme.

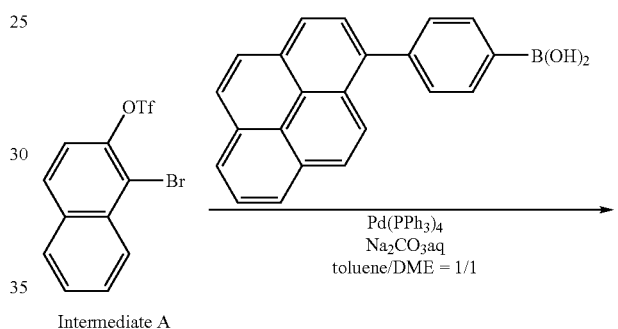

Intermediate A

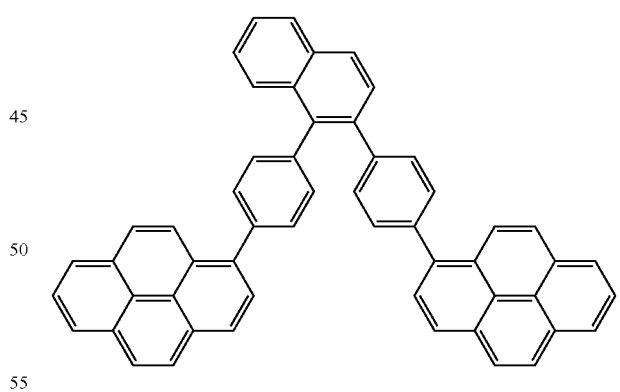

H-9

In the above-mentioned scheme, Pd(PPh$_3$)$_4$ means tetrakis (triphenylphosphine) palladium, Na$_2$CO$_3$aq means sodium carbonate aqueous solution, toluene/DME means toluene/dimethoxyethane respectively.

Synthesis Example 10

A host material H-10 was synthesized in accordance with the following scheme.

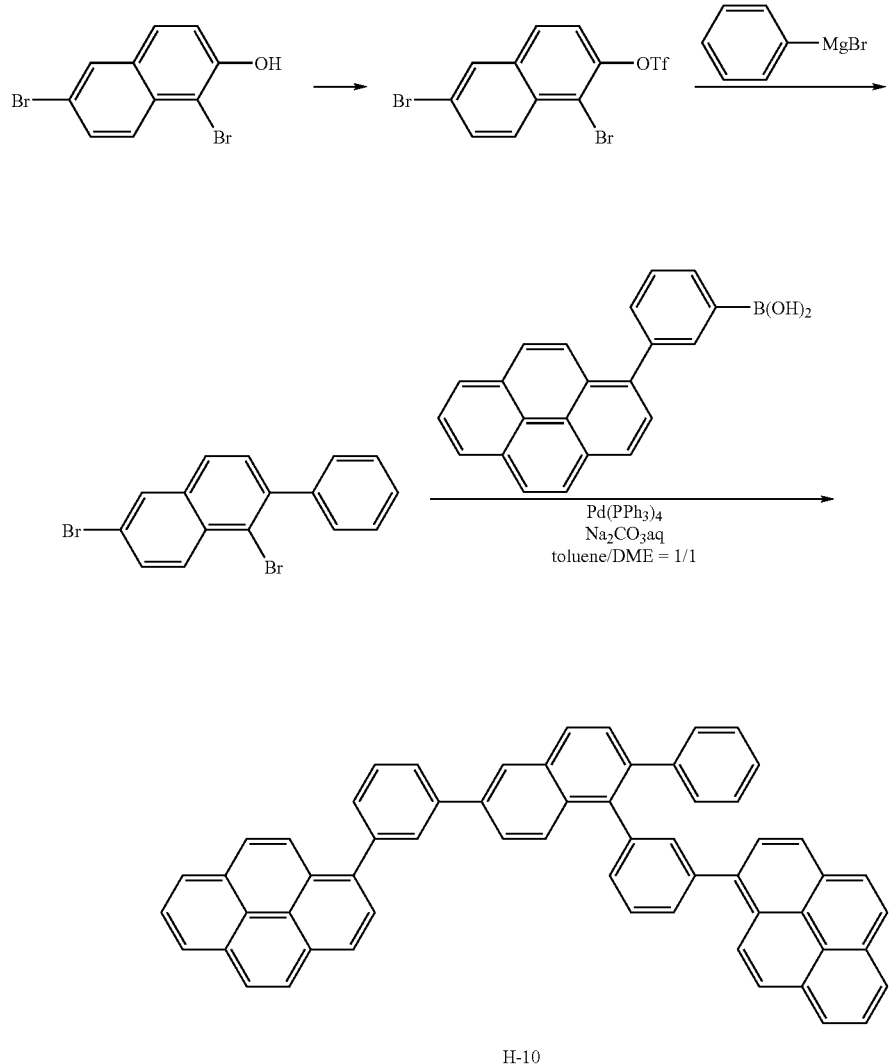

H-10

Example 1

A 130 nm-thick transparent electrode made of indium tin oxide was formed on a glass substrate having a size of 25 mm×75 mm×1.1 mm. The glass substrate was subjected to ultraviolet radiation and ozone radiation, and after it was cleaned, the substrate was mounted on a vacuum vapor deposition device.

First, N,N'-bis(N,N'-diphenyl-4-aminophenyl)-N,N-diphenyl-4,4'-diamino-1,1'-bipenyl film (hereinafter referred to as "TPD232 film") was vapor deposited into a film having a thickness of 60 nm as a hole injecting layer. N,N,N',N'-tetra(4-biphenyl)-diaminobiphenylene layer (hereinafter referred to as "TBDB layer") was vapor deposited into a film having a thickness of 20 nm as a hole transporting layer on the TPD232 film. Subsequently, the following compounds (H-1) and (D-1) were simultaneously deposited in such a manner that a weight ratio between (H-1) and (D-1) would be 40:2, to form a light emitting layer with a thickness of 40 nm.

Next, tris(8-hydroxyquinolinato)aluminum was vapor deposited on the light emitting layer to form an electron injecting layer having a thickness of 20 nm. Subsequently, lithium fluoride was vapor deposited up to 0.3 nm in thickness and then, aluminum was vapor deposited up to 150 nm in thickness. The aluminum/lithium fluoride functions as a cathode. An organic EL device was fabricated in the manner described above.

The device fabricated above was examined by feeding electric current. Blue light was emitted at a luminance of 650 $cd/m^2$ under a voltage of 6.2 V and a current density of 10 $mA/cm^2$.

Further, driving with a constant direct electric current continuously starting from an initial luminance of 1,000 $cd/m^2$, a half lifetime of luminance was evaluated as 17,800 hours. The results of the evaluation about the devices are summarized in Table 1.

H-1

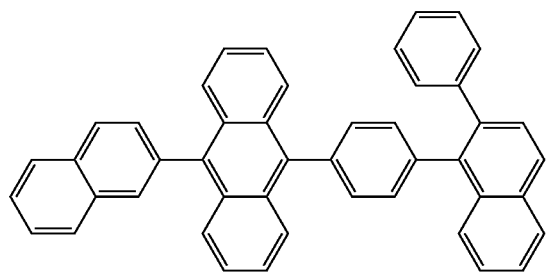

Alq

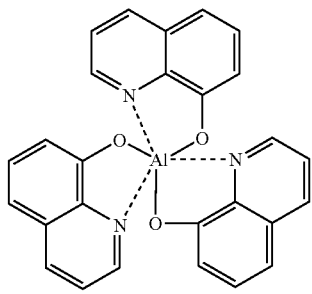

D-1

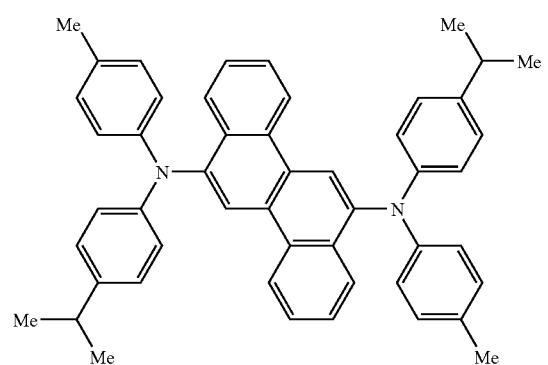

Examples 2 to 8

Organic EL devices were fabricated in the same manner as in Example 1 except that the light emitting materials described in Table 1 were used instead of the host material (H-1) of the light emitting layer in Example 1.

The results of the evaluation about the devices are summarized in Table 1.

Comparative Examples 1 and 2

Organic EL devices were fabricated in the same manner as in Example 1 except that the following comparative compounds (h-1) and (h-2) were used respectively instead of the host material (H-1) of the light emitting layer in Example 1.

TPD232

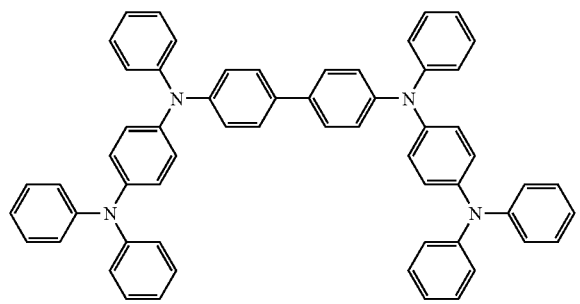

h-1

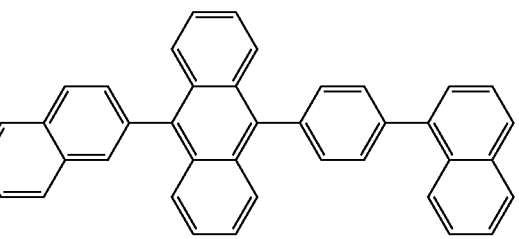

TPDB

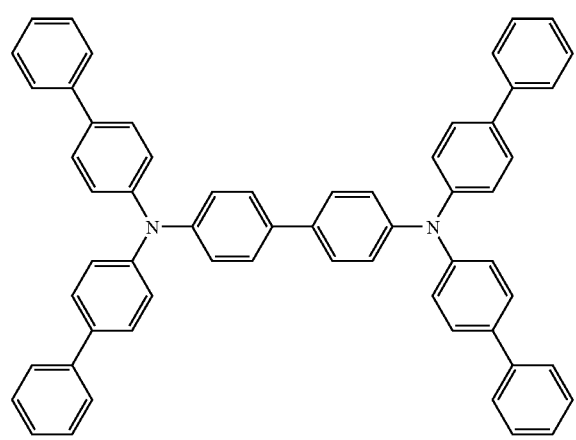

h-2

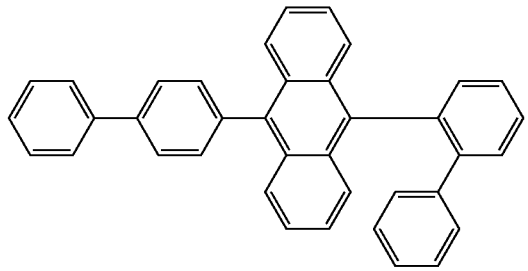

The results of the evaluation about the devices are summarized in Table 1.

TABLE 1

|  | Light emitting material | | Chromaticity | Current efficiency | Luminescence half life (hours) |
| --- | --- | --- | --- | --- | --- |
|  | Host material | Dopant | (CIEx, CIEy) | (cd/A) | Initial: 1000 cd/m$^2$ |
| Example 1 | H-1 | D-1 | (0.136, 0.137) | 7.26 | 8300 |
| Example 2 | H-2 | D-1 | (0.136, 0.138) | 7.16 | 8930 |
| Example 3 | H-3 | D-1 | (0.136, 0.135) | 7.36 | 8500 |
| Example 4 | H-4 | D-1 | (0.136, 0.134) | 7.46 | 9100 |
| Example 5 | H-5 | D-1 | (0.136, 0.137) | 7.13 | 8900 |
| Example 6 | H-6 | D-1 | (0.136, 0.138) | 7.09 | 8830 |
| Example 7 | H-7 | D-1 | (0.136, 0.134) | 6.80 | 7930 |
| Example 8 | H-8 | D-1 | (0.136, 0.136) | 7.27 | 8380 |
| Comparative Example 1 | h-1 | D-1 | (0.138, 0.158) | 5.70 | 3980 |
| Comparative Example 2 | h-2 | D-1 | (0.139, 0.148) | 5.63 | 1880 |

Since all the chromaticity's (CIEy values) of Examples in Table 1 are smaller in comparison with the values of Comparative Examples, it is found that employing the host materials having specific flexible partial structure, i.e., a structure containing an aromatic ring in which adjacent carbon atoms are substituted by another aromatic ring group and aliphatic group or an aromatic ring group elevates color purity, and makes higher luminescent efficiency and longer lifetimes to be compatible altogether.

Example 9

An organic EL device was fabricated in the same manner as in Example 1 except that the dopant material (D-1) of the light emitting layer in Example 1 was replaced to (D-2).

The results of the evaluation about the devices are summarized in Table 2.

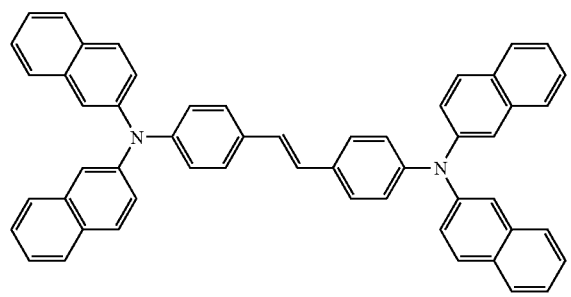

D-2

Comparative Example 3

An organic EL device was fabricated in the same manner as in Comparative Example 1 except that the dopant material (D-1) of the light emitting layer in Comparative Example 1 was replaced to (D-2).

The results of the evaluation about the devices are summarized in Table 2.

TABLE 2

|  | Light emitting material | | Chromaticity | Current efficiency | Luminescence half life (hours) |
| --- | --- | --- | --- | --- | --- |
|  | Host material | Dopant | (CIEx, CIEy) | (cd/A) | Initial: 1000 cd/m$^2$ |
| Example 9 | H-1 | D-1 | (0.146, 0.157) | 7.56 | 7790 |
| Comparative Example 3 | h-1 | D-2 | (0.157, 0.178) | 6.58 | 3600 |

From Table 2, despite the employment of the styryl diamine-based dopant material such as (D-2), it is found that a combination with the host materials having specific flexible partial structure, i.e., a structure containing an aromatic ring in which adjacent carbon atoms are substituted by another aromatic ring group and aliphatic group or an aromatic ring group elevates color purity, and makes higher luminescent efficiency and longer lifetimes to be compatible altogether.

Examples 10 and 11

Organic EL devices were fabricated in the same manner as in Example 1 except that the light emitting materials described in Table 3 were used instead of the host material (H-1) of the light emitting layer in Example 1.

The results of the evaluation about the devices are summarized in Table 3.

Comparative Example 3

Organic EL devices were fabricated in the same manner as in Example 1 except that the following comparative compound (h-3) was used respectively instead of the host material (H-1) in Example 1.

The results of the evaluation about the devices are summarized in Table 3.

TABLE 3

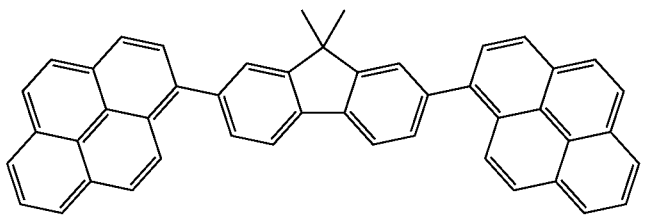 [SMILES: CC1(C)c2cc(-c3ccc4ccc5cccc6ccc3c4c56)ccc2-c2ccc(-c3ccc4ccc5cccc6ccc3c4c56)cc21]

h-3

| | Light emitting material | | Chromaticity | Current efficiency | Luminescence half life (hours) |
|---|---|---|---|---|---|
| | Host material | Dopant | (CIEx, CIEy) | (cd/A) | Initial: 1000 cd/m² |
| Example 10 | H-9 | D-1 | (0.148, 0.180) | 7.86 | 8790 |
| Example 11 | H-10 | D-1 | (0.150, 0.184) | 7.53 | 8930 |
| Comparative Example 3 | h-3 | D-1 | (0.150, 0.216) | 5.83 | 3820 |

From Table 3, concerning not only the anthracene-based hosts in Table 1 or Table 2 but also a pyrene based host material, it is found that a combination with the host materials having specific flexible partial structure, i.e., a structure containing an aromatic ring in which adjacent carbon atoms are substituted by another aromatic ring group and aliphatic group or an aromatic ring group elevates color purity, and makes higher luminescent efficiency and longer lifetimes to be compatible altogether.

Example 12

An organic EL device was fabricated in the same manner as in Example 10 except that the dopant material (D-1) of the light emitting layer in Example 10 was replaced to (D-2).

The results of the evaluation about the devices are summarized in Table 4.

Comparative Example 4

An organic EL device was fabricated in the same manner as in Comparative Example 3 except that the dopant material (D-1) of the light emitting layer in Comparative Example 3 was replaced to (D-2).

The results of the evaluation about the devices are summarized in Table 4.

From Table 4, despite the employment of the styryl diamine-based dopant material such as (D-2), it is found that a combination with the host materials having specific flexible partial structure, i.e., a structure containing an aromatic ring in which adjacent carbon atoms are substituted by another aromatic ring group and aliphatic group or an aromatic ring group elevates color purity, and makes higher luminescent efficiency and longer lifetimes to be compatible altogether.

Examples 13 and 14

Organic EL devices were fabricated in the same manner as in Example 1, except that the dopant material (D-1) of the light emitting layer in Example 1 was replaced to (D-3), and that the following compounds (H-11) and (H-12) were used instead of the host material (H-1).

The results of the evaluation about the devices are summarized in Table 5.

TABLE 4

| | Light emitting material | | Chromaticity | Current efficiency | Luminescence half life (hours) |
|---|---|---|---|---|---|
| | Host material | Dopant | (CIEx, CIEy) | (cd/A) | Initial: 1000 cd/m² |
| Example 12 | H-9 | D-2 | (0.159, 0.183) | 7.03 | 7290 |
| Comparative Example 4 | h-3 | D-2 | (0.161, 0.204) | 5.84 | 3690 |

Examples 15 to 17

Organic EL devices were fabricated in the same manners as in Example 1, except that the dopant material (D-1) of the light emitting layer in Example 1 was replaced to the following (D-4) to (D-6), and that the material (H-5) was used instead of the host material (H-1).

The results of the evaluation about the devices are summarized in Table 6.

Examples 18 to 20

Organic EL devices were fabricated in the same manners as in Example 1, except that the dopant material (D-1) of the light emitting layer in Example 1 was replaced to the following (D-4) to (D-6), and that the material (H-12) was used instead of the host material (HA.

The results of the evaluation about the devices are summarized in Table 6.

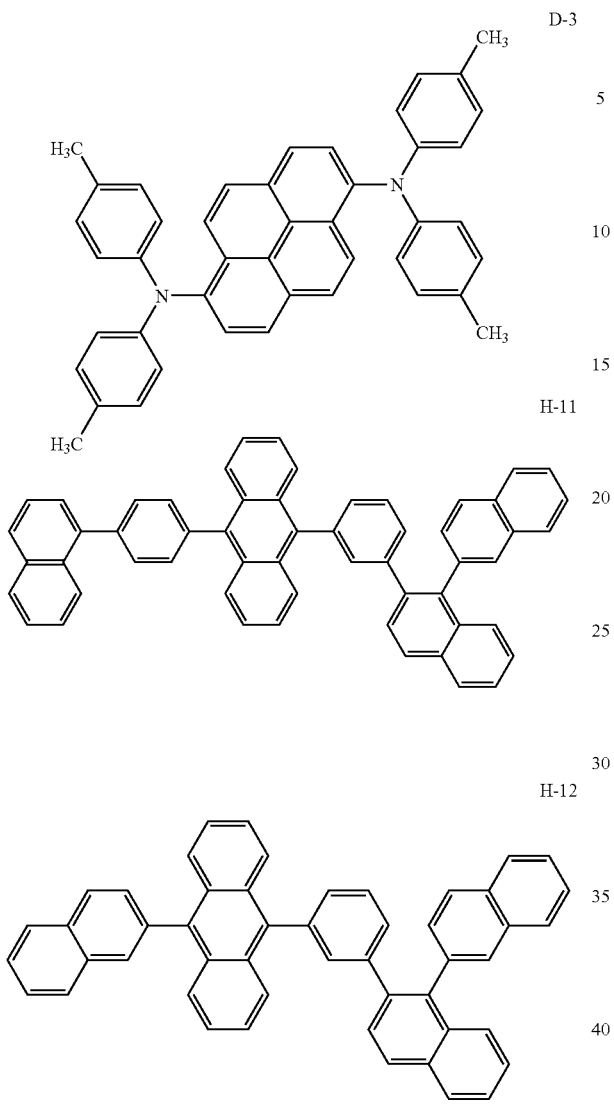

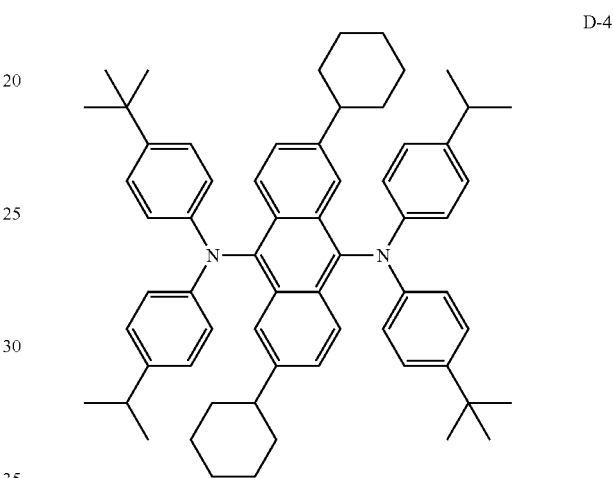

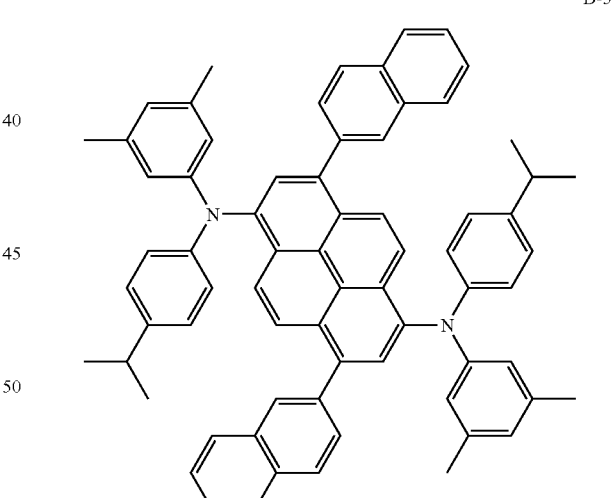

Comparative Example 6

An organic EL device was fabricated in the same manner as in Example 1, except that the dopant material (D-1) of the light emitting layer in Example 1 was replaced to (D-3), and that the material (h-2) was used instead of the host material (H-1).

The results of the evaluation about the devices are summarized in Table 5.

TABLE 5

| | Light emitting material | | Chromaticity | Current efficiency | Luminescence half life (hours) |
| --- | --- | --- | --- | --- | --- |
| | Host material | Dopant | (CIEx, CIEy) | (cd/A) | Initial: 1000 cd/m$^2$ |
| Example 13 | H-11 | D-3 | (0.159, 0.179) | 7.33 | 9290 |
| Example 14 | H-12 | D-3 | (0.159, 0.182) | 7.15 | 8890 |
| Comparative Example 6 | h-2 | D-3 | (0.161, 0.214) | 5.74 | 3390 |

-continued

D-6

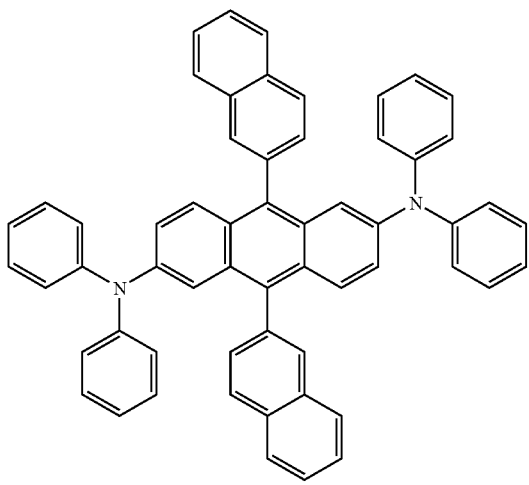

Comparative Examples 7 and 8

Organic EL devices were fabricated in the same manner as in Example 1, except that the dopant material (D-1) of the light emitting layer in Example 1 was replaced to (D-6), and that the materials (h-1) and (h-2) were used respectively instead of the host material (H-1).

The results of the evaluation about the devices are summarized in Table 6.

TABLE 6

| | Light emitting material | | Chromaticity | Current efficiency | Luminescence half life (hours) |
| --- | --- | --- | --- | --- | --- |
| | Host material | Dopant | (CIEx, CIEy) | (cd/A) | Initial: 1000 cd/m$^2$ |
| Example 15 | H-5 | D-4 | (0.333, 0.620) | 25.62 | 10200 |
| Example 16 | H-5 | D-5 | (0.280, 0.642) | 22.13 | 11800 |
| Example 17 | H-5 | D-6 | (0.319, 0.638) | 23.89 | 10300 |
| Example 18 | H-12 | D-4 | (0.334, 0.624) | 24.50 | 11500 |
| Example 19 | H-12 | D-5 | (0.285, 0.650) | 22.52 | 12300 |
| Example 20 | H-12 | D-6 | (0.321, 0.640) | 23.30 | 10500 |
| Comparative Example 7 | h-1 | D-6 | (0.319, 0.639) | 18.99 | 5800 |
| Comparative Example 8 | h-2 | D-6 | (0.313, 0.640) | 19.53 | 3300 |

Comparing Examples and Comparative Examples, it is found that employing the light emitting material for the organic EL device having specific flexible partial structure, i.e., a structure containing an aromatic ring in which adjacent carbon atoms are substituted by another aromatic ring group and aliphatic group or an aromatic ring group improves color purity of blue or green, and at the same time, enables to obtain a light emitting device with higher luminescent efficiency and longer lifetimes.

INDUSTRIAL APPLICABILITY

As described above in detail, an employment of the light emitting material for the organic EL device having specific flexible partial structure, i.e., a structure containing an aromatic ring in which adjacent carbon atoms are substituted by another aromatic ring group and aliphatic group or an aromatic ring group or the polymer compound constituted of repeating units at least part of which are structures derived from the polycyclic ring assembly compound improves color purity of blue or green, and at the same time, enables to obtain the organic EL device being excellent in heat resistance, with a high color purity, with a long lifetime, and with higher luminescent efficiency. Further, it is possible to produce the organic EL device easily and with relatively reasonable expense. Furthermore, the organic EL device of the present invention can be also fabricated using the solution of the organic EL material containing the foregoing polycyclic ring assembly compound or the forgoing polymer compound The organic EL device of the present invention can find use in applications including: a flat luminous body such as a flat panel display of a wall hanging television; a light source for the backlight, meters, or the like of a copying machine, a printer, or a liquid crystal display; a display panel; and a signal lamp.

The invention claimed is:

1. An organic electroluminescence device, comprising one or more organic thin film layers including at least one light emitting layer interposed between a cathode and an anode, wherein at least one of the organic thin film layers comprises a polycyclic ring assembly compound represented by formula (1) as a light emitting material:

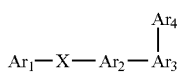

wherein
Ar$_1$ represents a hydrogen atom, a substituted or unsubstituted aromatic ring group having 6 to 50 ring carbon atoms, or a substituted or unsubstituted aromatic heterocyclic ring group having 5 to 50 ring atoms;
wherein the substituent of the aromatic ring group and the aromatic heterocyclic ring group is selected from the group consisting of an alkyl group having 1 to 8 carbon atoms, a silyl group having 3 to 24 carbon atoms, an alkoxy group having 1 to 8 carbon atoms, a fluorine atom, a diphenylamino group, a dibenzofuranyl group, and a dibenzothiophenyl group;

X represents a substituted or unsubstituted 9,10-anthracenediyl group; and

—Ar$_2$—Ar$_3$—Ar$_4$ is represented by one of formulae (4) to (6):

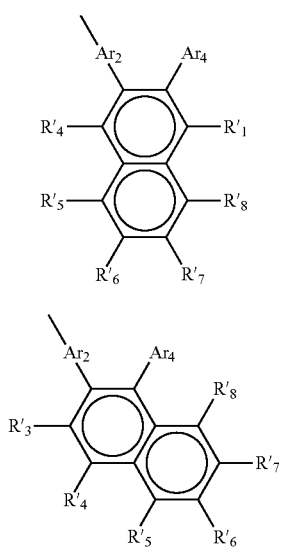

(4)

(5)

wherein

Ar$_2$ represents a phenylene group;

Ar$_4$ represents a methyl group, a phenyl group, a 1-naphthyl group, a 2-naphthyl group, a 2-biphenylyl group, a 3-biphenylyl group, or a 4-biphenylyl group; and R'$_1$ and R'$_3$ to R'$_8$ each independently represents a hydrogen atom or a phenyl group.

2. The organic electroluminescence device according to claim 1, wherein the light emitting layer comprises the polycyclic ring assembly compound as its host material.

3. The organic electroluminescence device according to claim 2, which comprises at least one of a styrylamine compound and an aromatic amine compound.

4. The organic electroluminescence device according to claim 1, wherein:

Ar$_1$ represents a substituted or unsubstituted aromatic ring group having 6 to 50 ring carbon atoms;

X represents a substituted or unsubstituted 9,10-anthracenediyl group;

Ar$_2$ represents a substituted or unsubstituted divalent aromatic ring group having 6 to 50 ring carbon atoms;

Ar$_3$ represents a substituted or unsubstituted divalent fused aromatic ring group having 10 to 50 ring carbon atoms; and Ar$_4$ represents a substituted or unsubstituted aromatic ring group having 6 to 50 ring carbon atoms or a substituted or unsubstituted alkyl group having 1 to 50 carbon atoms.

5. The organic electroluminescence device according to claim 1, wherein the polycyclic ring assembly compound is represented by formula (18):

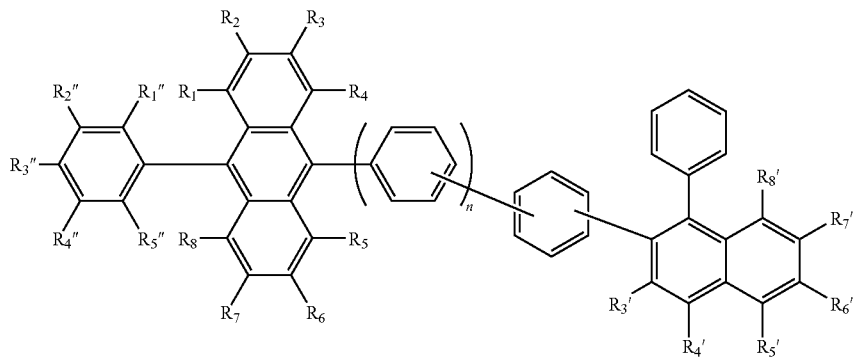

(18)

-continued

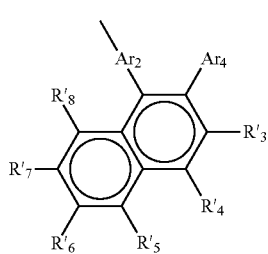

(6)

wherein R$_1$ to R$_8$ are all hydrogen atoms; R$_3$' to R$_8$' each independently represents a hydrogen atom or a phenyl group; R$_1$" to R$_5$" each independently represents a hydrogen atom or a substituent selected from the group consisting of a methyl group, a trimethylsilyl group, a methoxy group, a fluorine atom, a diphenylamino group, a dibenzofuranyl group, and a dibenzothiophenyl group; and n represents 0.

6. The organic electroluminescence device according to claim 1, wherein the polycyclic ring assembly compound is represented by formula (19):

(19)

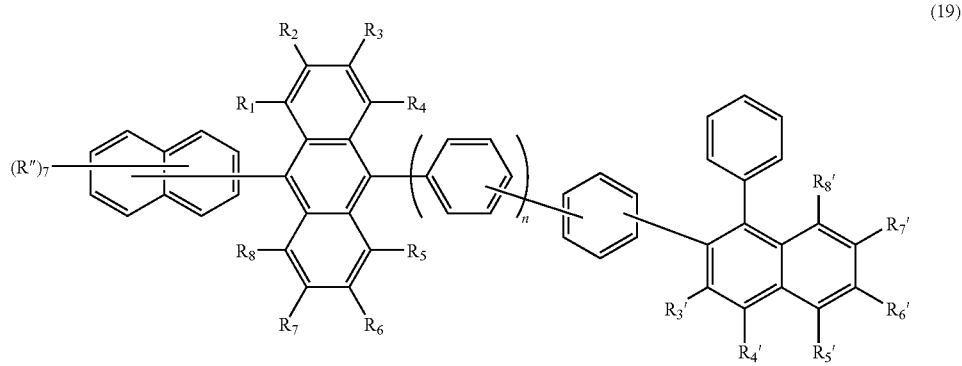

wherein $R_1$ to $R_8$ are all hydrogen atoms; $R_3'$ to $R_8'$ each independently represents a hydrogen atom or a phenyl group; seven R"s each independently represents a hydrogen atom or a substituent selected from the group consisting of a methyl group, a trimethylsilyl group, a methoxy group, a fluorine atom, a diphenylamino group, a dibenzofuranyl group, and a dibenzothiophenyl group; and n represents 0.

7. The organic electroluminescence device according to claim 1, wherein the polycyclic ring assembly compound is represented by formula (20):

(20)

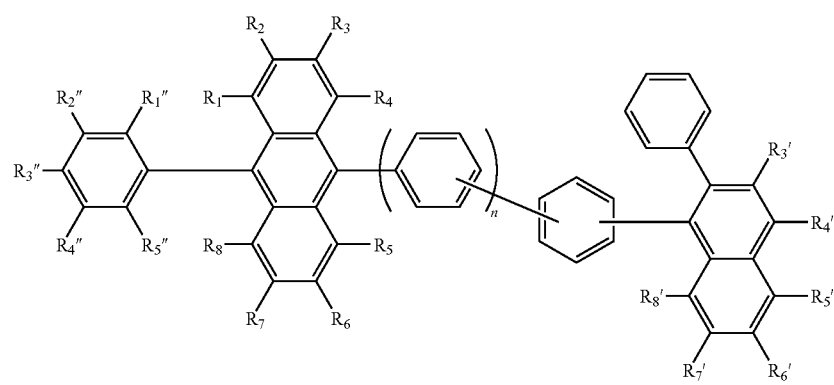

wherein $R_1$ to $R_8$ are all hydrogen atoms; $R_3'$ to $R_8'$ each independently represents a hydrogen atom or a phenyl group; $R_1''$ to $R_5''$ each independently represents a hydrogen atom or a substituent selected from the group consisting of a methyl group, a trimethylsilyl group, a methoxy group, a fluorine atom, a diphenylamino group, a dibenzofuranyl group, and a dibenzothiophenyl group; and n represents 0.

8. The organic electroluminescence device according to claim 1, wherein the polycyclic ring assembly compound is represented by formula (21):

(21)

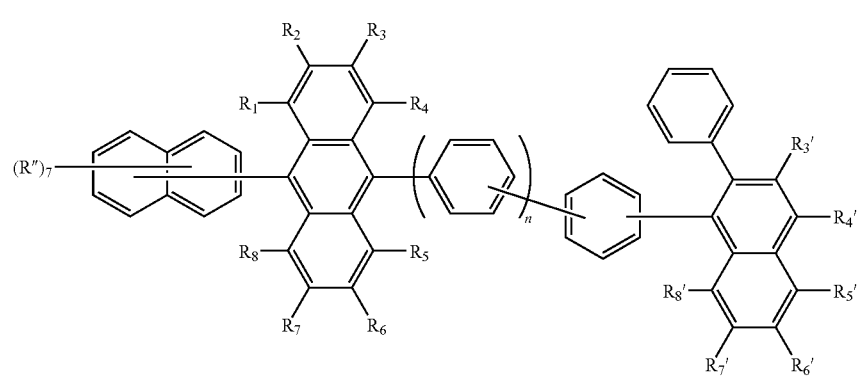

wherein $R_1$ to $R_8$ are all hydrogen atoms; $R_3'$ to $R_8'$ each independently represents a hydrogen atom or a phenyl group; seven R"s each independently represents a hydrogen atom or a substituent selected from the group consisting of a methyl group, a trimethylsilyl group, a methoxy group, a fluorine atom, a diphenylamino group, a dibenzofuranyl group, and a dibenzothiophenyl group; and n represents 0.

9. The organic electroluminescence device according to claim 1, wherein the polycyclic ring assembly compound is represented by formula (22):

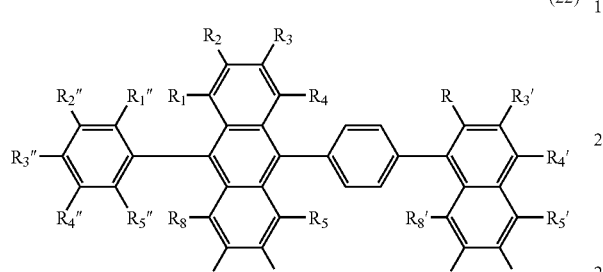

(22)

wherein R represents a methyl group; $R_1$ to $R_8$ are all hydrogen atoms; $R_3'$ to $R_8'$ each independently represents a hydrogen atom or a phenyl group; and $R_1''$ to $R_5''$ each independently represents a hydrogen atom or a substituent selected from the group consisting of a methyl group, a trimethylsilyl group, a methoxy group, a fluorine atom, a diphenylamino group, a dibenzofuranyl group, and a dibenzothiophenyl group.

10. The organic electroluminescence device according to claim 1, wherein $R'_1$ and $R'_3$ to $R'_8$ are all hydrogen atoms.

11. The organic electroluminescence device according to claim 10, wherein $Ar_1$ represents an unsubstituted aromatic ring group having 6 to 50 ring carbon atoms or an unsubstituted aromatic heterocyclic ring group having 5 to 50 ring atoms, and X represents an unsubstituted 9,10-anthracenediyl group.

12. The organic electroluminescence device according to claim 5, wherein $R_3'$ to $R_8$ and $R_1''$ to $R_5''$ are all hydrogen atoms.

13. The organic electroluminescence device according to claim 6, wherein $R_3'$ to $R_8$ and seven R"s are all hydrogen atoms.

14. The organic electroluminescence device according to claim 7, wherein $R_3'$ to $R_8'$ and $R_1''$ to $R_5''$ are all hydrogen atoms.

15. The organic electroluminescence device according to claim 8, wherein $R_3'$ to $R_8'$ and seven R"s are all hydrogen atoms.

16. The organic electroluminescence device according to claim 9, wherein $R_3'$ to $R_8'$ and $R_1''$ to $R_5''$ are all hydrogen atoms.

17. The organic electroluminescence device according to claim 1, wherein the polycyclic ring assembly compound is selected from the following compounds:

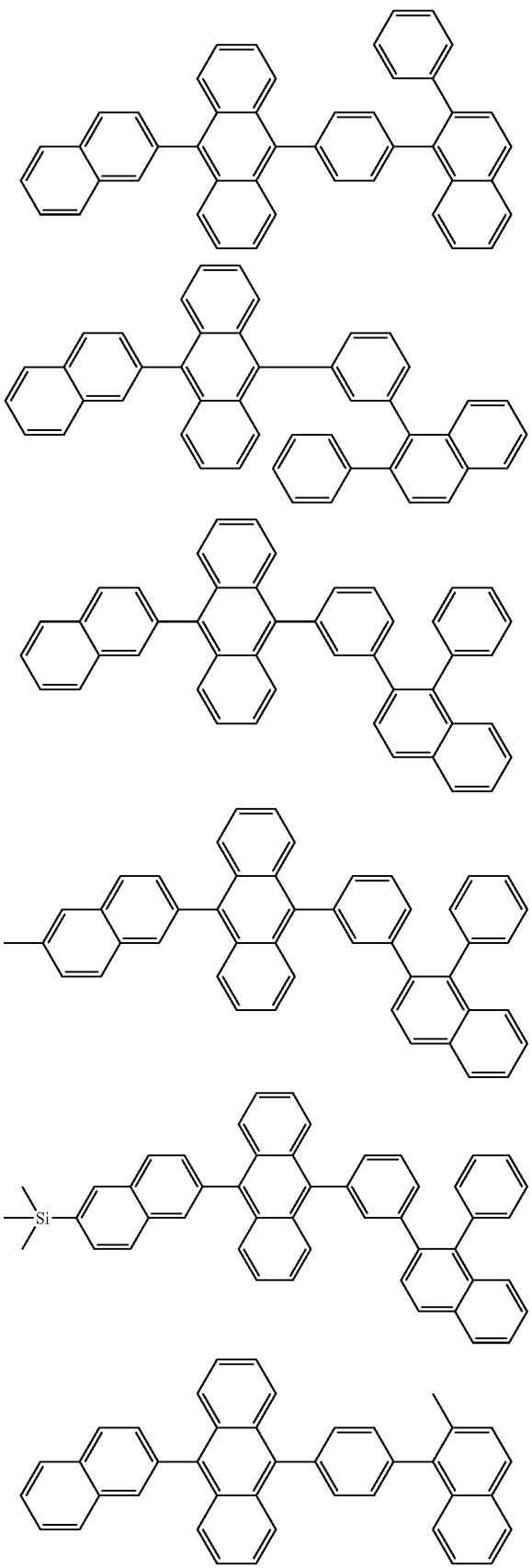

127
-continued
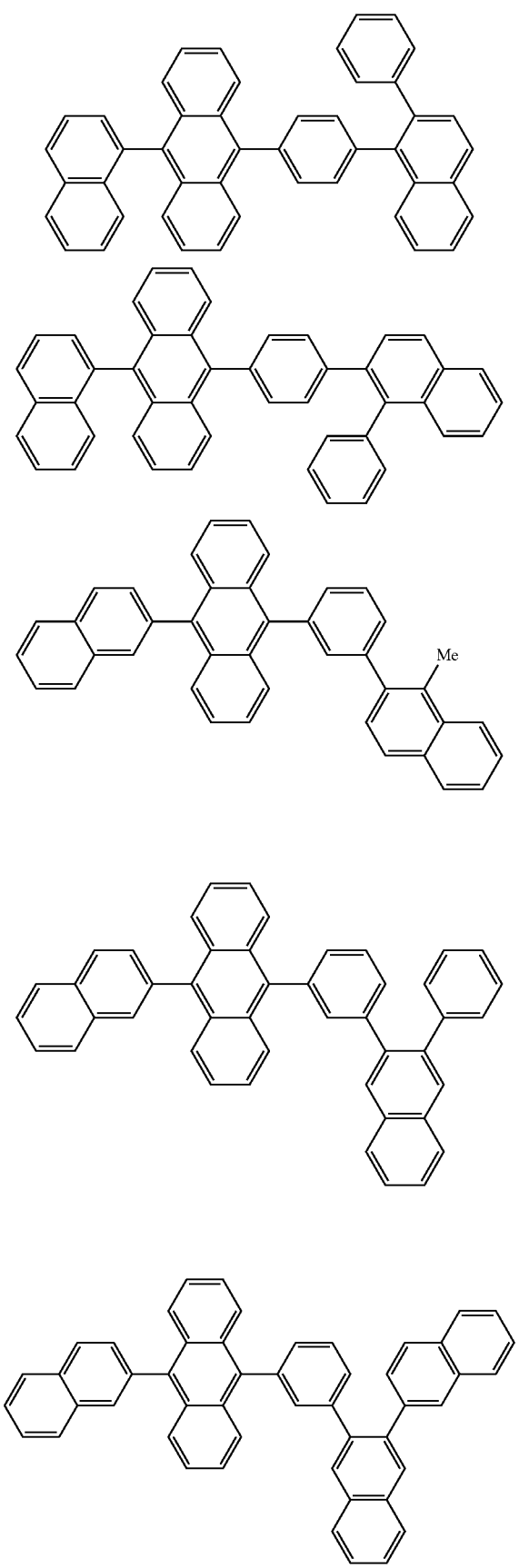
128
-continued
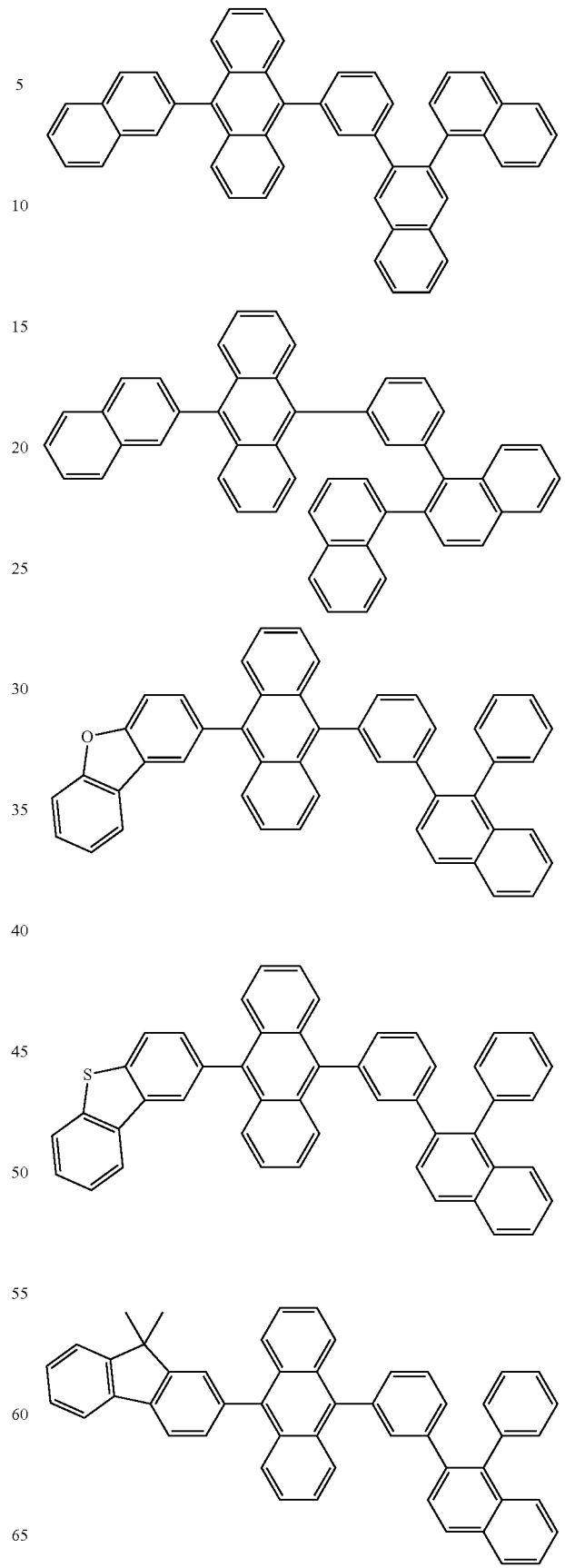

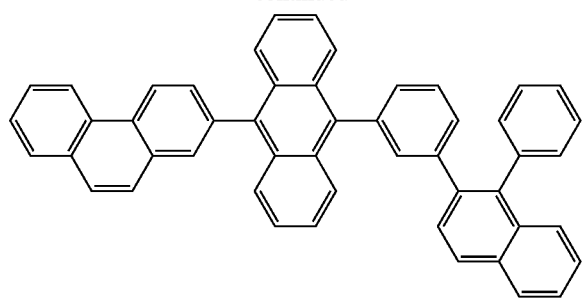
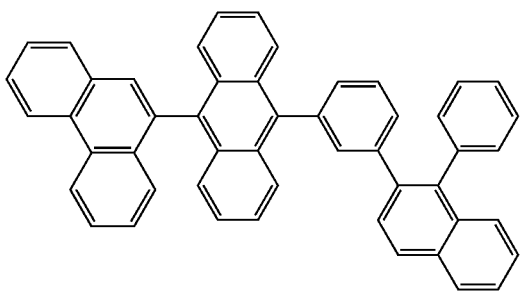
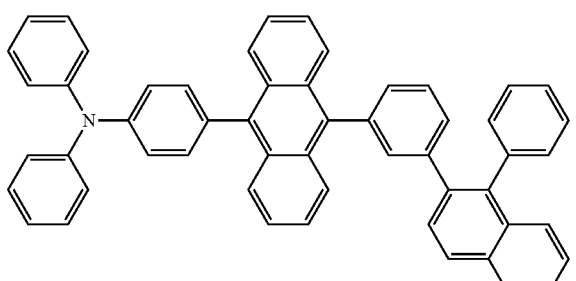
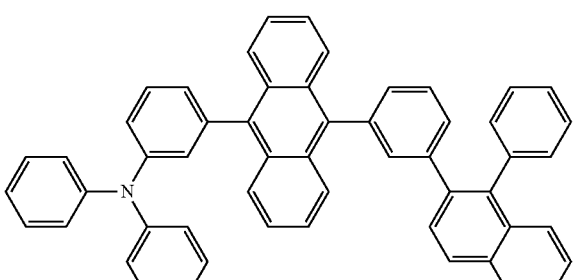
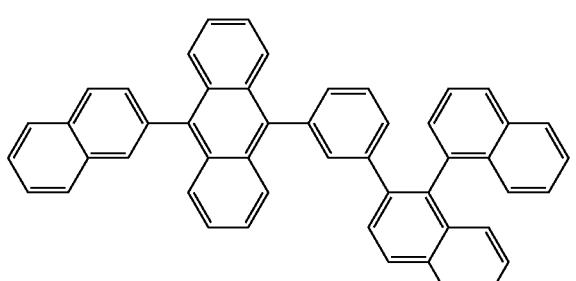
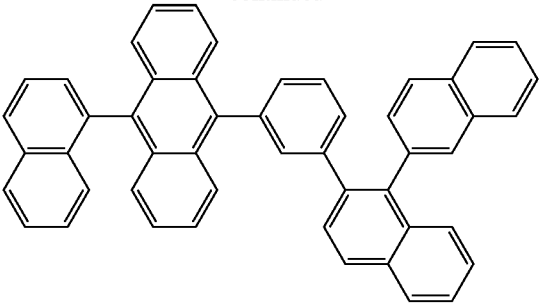
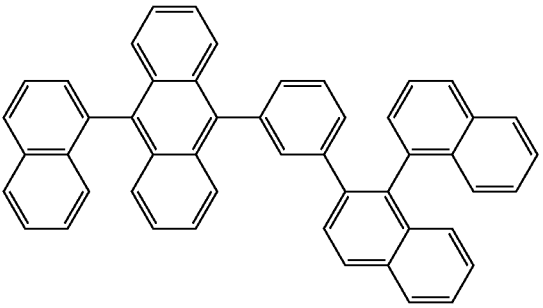
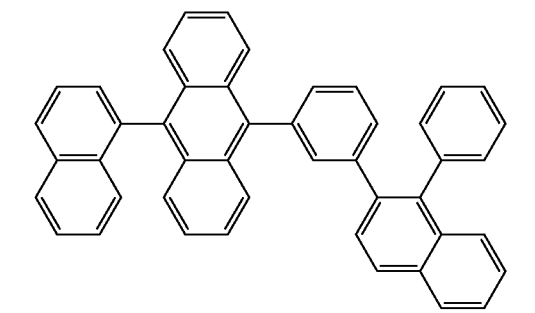
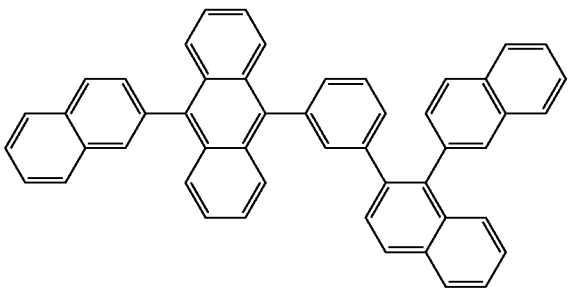
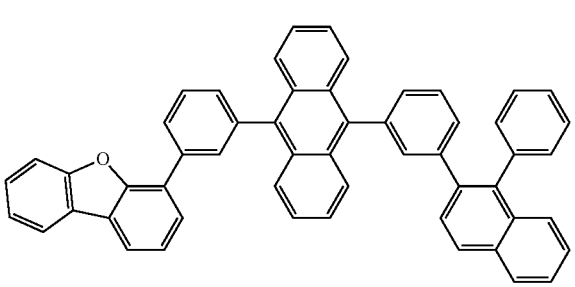

131
-continued
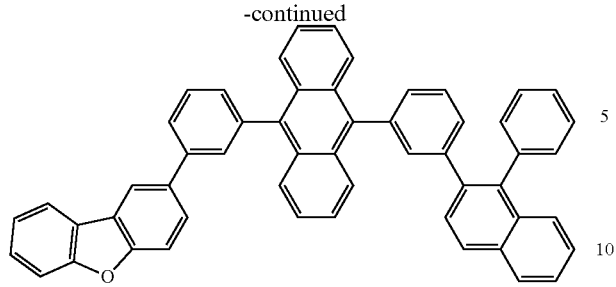
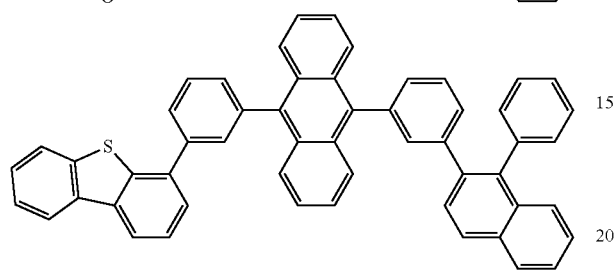
132
-continued
and
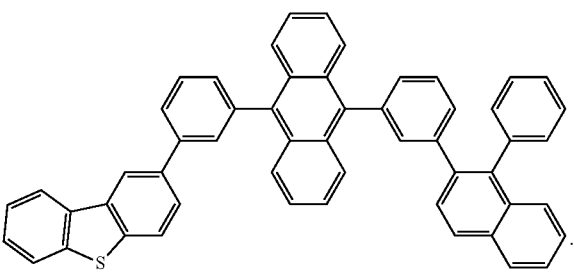
* * * * *